US012583926B2

(12) United States Patent
Wang et al.

(10) Patent No.: US 12,583,926 B2
(45) Date of Patent: Mar. 24, 2026

(54) CD47/PD-L1-TARGETING PROTEIN COMPLEX AND METHODS OF USE THEREOF

(71) Applicant: FBD Biologics Limited, Kowloon (HK)

(72) Inventors: Jiin-Tarng Wang, Taichung City (TW); Han-Fang Teng, New Taipei City (TW); Yun-Chih Cheng, Taipei (TW); Pan-Hsien Kuo, Taoyuan City (TW); Chieh-Hsin Ho, Taipei (TW); Wei-Tse Sun, Taipei (TW); Chia-Zhen Wu, Taipei (TW); Tsai-Kuei Shen, Taipei (TW); Chi-Ling Tseng, Taipei City (TW); Zong Sean Juo, New Taipei City (TW)

(73) Assignee: FBD Biologics Limited, Tsim Sha Tsui (HK)

( * ) Notice: Subject to any disclaimer, the term of this patent is extended or adjusted under 35 U.S.C. 154(b) by 0 days.

(21) Appl. No.: 18/770,712

(22) Filed: Jul. 12, 2024

(65) Prior Publication Data

US 2024/0400691 A1 Dec. 5, 2024

Related U.S. Application Data

(63) Continuation of application No. PCT/CN2024/096554, filed on May 31, 2024.

(60) Provisional application No. 63/470,003, filed on May 31, 2023.

(51) Int. Cl.
| | |
|---|---|
| *C07K 16/28* | (2006.01) |
| *A61P 35/00* | (2006.01) |
| *C07K 14/705* | (2006.01) |
| *C07K 14/71* | (2006.01) |
| *A61K 38/00* | (2006.01) |
| *A61K 39/00* | (2006.01) |

(52) U.S. Cl.
CPC .......... *C07K 16/2827* (2013.01); *A61P 35/00* (2018.01); *C07K 14/70503* (2013.01); *C07K 14/71* (2013.01); *C07K 16/2803* (2013.01); *A61K 38/00* (2013.01); *A61K 2039/505* (2013.01); *C07K 2317/569* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 8,728,474 B2 | 5/2014 | Honjo et al. |
| 9,834,606 B2 | 12/2017 | Li et al. |
| 9,944,911 B2 | 4/2018 | Ring et al. |
| 9,969,789 B2 | 5/2018 | Uger et al. |
| 10,259,859 B2 | 4/2019 | Pons et al. |
| 10,696,730 B2 | 6/2020 | Pons et al. |
| 10,800,821 B2 | 10/2020 | Tian et al. |
| 10,906,954 B2 | 2/2021 | Uger et al. |
| 11,208,459 B2 | 12/2021 | Pons et al. |
| 11,208,481 B2 | 12/2021 | Ring et al. |
| 2006/0115832 A1 | 6/2006 | Hoon et al. |
| 2006/0275844 A1 | 12/2006 | Linke et al. |
| 2008/0280297 A1 | 11/2008 | Dalla-Favera et al. |
| 2011/0190157 A1 | 8/2011 | Kipps et al. |
| 2012/0178111 A1 | 7/2012 | Diamandis et al. |
| 2013/0017199 A1 | 1/2013 | Langermann |
| 2015/0071905 A1 | 3/2015 | Ring et al. |
| 2015/0329616 A1 | 11/2015 | Uger et al. |
| 2016/0177276 A1 | 6/2016 | Lo |
| 2017/0247454 A1 | 8/2017 | Benz et al. |
| 2017/0247476 A1 | 8/2017 | Yan et al. |
| 2019/0144549 A1 | 5/2019 | Fox et al. |
| 2020/0087377 A1 | 3/2020 | Yue |
| 2020/0157180 A1 | 5/2020 | Gu |
| 2021/0101982 A1 | 4/2021 | Kwan |
| 2021/0179716 A1 | 6/2021 | Riggers et al. |
| 2021/0230277 A1 | 7/2021 | Liu et al. |
| 2023/0083670 A1 | 3/2023 | Tian et al. |
| 2024/0083960 A1 | 3/2024 | Wang et al. |
| 2024/0228584 A1 | 7/2024 | Jiin-Tarng et al. |
| 2024/0360219 A1 | 10/2024 | Wang et al. |

FOREIGN PATENT DOCUMENTS

| | | |
|---|---|---|
| AU | 2013362789 B2 | 3/2018 |
| AU | 2016210755 B2 | 5/2021 |
| CN | 104136037 B | 2/2018 |
| CN | 108350048 A | 7/2018 |

(Continued)

OTHER PUBLICATIONS

Chen et al., Generation and analysis of random point mutations in an antibody CDR2 sequence: many mutated antibodies lose their ability to bind antigen; 1992, J. Experimental Medicine, 176:855-866. (Year: 1992).*

MacCallum et al., Antibody-antigen interactions: contact analysis and binding site topography, 1996, J. Mol. Biol., 262: 732-745. (Year: 1996).*

Lee et al., Novel structural determinants on SIRPa that mediate binding to CD47; 2007, J. Immunology, 179(11): 7741-7750. (Year: 2007).*

Liu et al., Dual targeting of innate and adaptive checkpoints on tumor cells limits immune evasion; 2018, Cell Reports, 24: 2101-2111. (Year: 2018).*

Qu et al., Targeting CD47/SIRPa as a therapeutic strategy, where we are and where we are headed; 2022; Biomarker Research, 10:20 1-18. (Year: 2022).*

(Continued)

*Primary Examiner* — Nelson B Moseley, II
*Assistant Examiner* — James Ryland Melchior
(74) *Attorney, Agent, or Firm* — Fish & Richardson P.C.

(57) ABSTRACT

This disclosure relates to protein complexes targeting CD47, PD-L1, and/or TGFβ, and methods of use thereof. In one aspect, the protein complexes include a CD47-binding domain having all or a portion of the SIRPα extracellular region; a PD-L1-binding domains having a VHH that binds to PD-L1; and optionally a TGFβ-binding domain having all or a portion of the TGFBRII extracellular region.

13 Claims, 35 Drawing Sheets

Specification includes a Sequence Listing.

(56) References Cited

FOREIGN PATENT DOCUMENTS

| CN | 106146670 B | 1/2019 | |
| CN | 105073780 B | 4/2019 | |
| CN | 112940134 A | 6/2021 | |
| CN | 113004414 A | 6/2021 | |
| CN | 113968903 A | 1/2022 | |
| CN | 114375310 A | 4/2022 | |
| CN | 115397853 A | 11/2022 | |
| CN | 117597141 A | 2/2024 | |
| EP | 3287470 A1 | 2/2018 | |
| EP | 3331902 | 6/2018 | |
| EP | 2931752 B1 | 8/2019 | |
| EP | 2804617 B1 | 6/2020 | |
| EP | 3128005 B1 | 4/2021 | |
| EP | 3575326 B1 | 4/2022 | |
| WO | WO 2008/077546 | 7/2008 | |
| WO | WO 2008/157367 | 12/2008 | |
| WO | WO-2011109789 A2 * | 9/2011 | A61K 31/704 |
| WO | WO 2013/109752 | 7/2013 | |
| WO | WO 2014/094122 | 6/2014 | |
| WO | WO 2015/027082 | 2/2015 | |
| WO | WO 2016/023040 | 2/2016 | |
| WO | WO 2016/169261 A1 | 10/2016 | |
| WO | WO 2017/027422 | 2/2017 | |
| WO | WO-2017027422 A1 * | 2/2017 | A61K 38/00 |
| WO | WO 2018/094173 | 5/2018 | |
| WO | WO 2019/084692 A1 | 5/2019 | |
| WO | WO-2019096121 A1 * | 5/2019 | A61K 39/3955 |
| WO | WO 2020/233539 A1 | 11/2020 | |
| WO | WO 2021/005599 | 1/2021 | |
| WO | WO 2021/041886 | 3/2021 | |
| WO | WO 2021/081258 | 4/2021 | |
| WO | WO 2021/185337 A1 | 9/2021 | |
| WO | WO 2022/063316 | 3/2022 | |
| WO | WO 2022/177394 A1 | 8/2022 | |
| WO | WO 2023/140950 A1 | 7/2023 | |
| WO | WO-2024140998 A2 * | 7/2024 | A61P 35/00 |
| WO | WO-2024193635 A1 * | 9/2024 | C07K 14/70503 |

OTHER PUBLICATIONS

Baxevanis, "Antibody-based cancer therapy," Expert Opinion on Drug Discovery, Apr. 2008, 3(4):441-52.
Bierie et al., "TGFβ: the molecular Jekyll and Hyde of cancer," Nature Reviews Cancer, Jul. 2006, 6(7):506-20.
Chowdhury et al., "Epigenetic targeting of transforming growth factor β receptor II and implications for cancer therapy," Molecular and Cellular Pharmacology, Jan. 2009, 1(1):57, 19 pages.
De Crescenzo, "Three key residues underlie the differential affinity of the TGFβ isoforms for the TGFβ type II receptor," Journal of Molecular Biology, Jan. 2006, 355(1):47-62.
Dhanda et al., "Development of a strategy and computational application to select candidate protein analogues with reduced HLA binding and immunogenicity," Immunology, Jan. 2018, 153(1):118-32.
EP Extended European Search Report in European Appln. No. 24150099.0, mailed on Jun. 6, 2024, 8 pages.
Gatti-Mays et al., "M7824: a promising new strategy to combat cancer immune evasion," Oncoscience, Nov. 2018, 5(11-12):269-70.
GenBank Acession No. NP_542970.1, "tyrosine-protein phosphatase non-receptor type substrate 1 isoform 1 precursor [Homo sapiens]," dated Dec. 13, 2020, 6 pages.
Ha et al., "Immunoglobulin Fc heterodimer platform technology: from design to applications in therapeutic antibodies and proteins," Frontiers in Immunology, Oct. 2016, 7:394, 16 pages.
Han et al., "PD-1/PD-L1 pathway: current researches in cancer," American Journal of Cancer Research, 2020 10(3):727-42.
Hirano et al., "Blockade of B7-H1 and PD-1 by monoclonal antibodies potentiates cancer therapeutic immunity," Cancer Research, Feb. 2005, 65(3):1089-96.

Huang (Computation and Structural Biotechnology Journal, vol. 19, p. 5494-5503, 2021) (Year: 2021).
Huang et al. "Regulation of CD47 expression in cancer cells," Translational Oncology, Dec. 2020, 13(12): 100862, 7 pages.
Jiang et al., "Targeting CD47 for cancer immunotherapy," Journal of Hematology & Oncology, Dec. 2021, 14(1), 18 pages.
Kim et al, "Novel therapies emerging in oncology to target the TGF-β pathway," Journal of Hematology & Oncology, Dec. 2021, 14, 20 pages.
Kwok et al., "Pembrolizumab (keytruda)," Human Vaccines & Immunotherapeutics, Nov. 2016, 12(11):2777-89.
Lei et al., "Resistance mechanisms of anti-PD1/PDL1 therapy in solid tumors," Frontiers in Cell and Developmental Biology, Jul. 2020, 8:672.
Lind et al, "Dual targeting of TGF-β and PD-L1 via a bifunctional anti-PD-L1/TGF-βRII agent: status of preclinical and clinical advances," Journal for Immunotherapy of Cancer, Feb. 2020, 8(1), 10 pages.
Liu et al. "PD-1/PD-L1 checkpoint inhibitors in tumor immunotherapy," Frontiers in Pharmacology, Sep. 2021, 12, 8 pages.
NCBI Accession No. AAH26692.1, "SIRPA protein [Homo sapiens]," Jun. 6, 2006, 4 pages.
NCBI Accession No. NP_003233.4, "TGF-beta receptor type-2 isoform B precursor [Homo sapiens]," Dec. 27, 2021, 4 pages.
NCBI Accession No. NP_005009.2, "programmed cell death protein 1 precursor [Homo sapiens], " Jan. 2, 2022, 5 pages.
PCT International Preliminary Report on Patentability in International Appln. No. PCT/US2022/053125, mailed on Mar. 16, 2024, 12 pages.
PCT International Search Report and Written Opinion in International Appln. No. PCT/CN2023/140179, mailed on Jan. 24, 2024, 14 pages.
PCT International Search Report and Written Opinion in International Appln. No. PCT/US2022/052373, mailed on Jun. 15, 2023, 15 pages.
Powles et al., "MPDL3280A (anti-PD-L1) treatment leads to clinical activity in metastatic bladder cancer," Nature, Nov. 2014, 515(7528): 558-562.
Raedler et al., "Keytruda (pembrolizumab): first PD-1 inhibitor approved for previously treated unresectable or metastatic melanoma," American Health & Drug Benefits, Mar. 2015, 8(Spec Feature):96, 5 pages.
Seiffert et al., "Signal-regulatory protein α (SIRPα) but not SIRPβ is involved in T-cell activation, binds to CD47 with high affinity, and is expressed on immature CD34+ CD38– hematopoietic cells," Blood, The Journal of the American Society of Hematology, May 2001, 97(9):2741-9.
Shimabukuro-Vornhagen et al., "Cytokine release syndrome," Journal for Immunotherapy of Cancer, Dec. 2018, 6:56, 14 pages.
Sikic et al., "First-in-human, first-in-class phase I trial of the anti-CD47 antibody Hu5F9-G4 in patients with advanced cancers," Journal of Clinical Oncology, Apr. 2019, 37(12):946, 11 pages.
Topalian et al., "Safety, activity, and immune correlates of anti-PD-1 antibody in cancer," New England Journal of Medicine, Jun. 2012, 366(26):2443-54.
UniProt ID No. P37173, "TGF-beta receptor type-2," Oct. 17, 2006, 20 pages.
UniProt ID No. P78324, "Tyrosine-protein phosphatase non-receptor type substrate 1," Mar. 28, 2003, 13 pages.
Wang et al., "HCB101: A safe and effective ligand trap therapeutic targeting the CD47-SIRPa signaling pathway for cancer treatment," Abstract, Journal of Immunotherapy, Nov. 2022, 10(2):A1-595, 1 page.
Weiskopf et al., "Engineered SIRPα variants as immunotherapeutic adjuvants to anticancer antibodies," Science. Jul. 2013, 341(6141):88, 13 pages.
Xue et al., "Transforming growth factor-β: a multifunctional regulator of cancer immunity," Cancers, Oct. 2020, 12(11):3099, 32 pages.
Yanagita et al. "Anti-SIRPα antibodies as a potential new tool for cancer immunotherapy," JCI Insight, Jan. 2017, 2(1), 16 pages.
PCT International Preliminary Report on Patentability in International Appln. No. PCT/US2022/052373, mailed on Jul. 4, 2024, 10 pages.

(56)        References Cited

OTHER PUBLICATIONS

PCT International Preliminary Report on Patentability in International Appln. No. PCT/US2022/053125, mailed on Aug. 2, 2024, 8 pages.
Brinkmann et al., "The making of bispecific antibodies," Mabs, Feb. 2017, 9(2):182-212.
Gulley et al., "Dual inhibition of TGF-β and PD-L1: a novel approach to cancer treatment," Molecular Oncology, Jun. 2022, 16(11):2117-34.
Ke et al., "HX009, a novel BsAb dual targeting PD1 x CD47, demonstrates potent anti-lymphoma activity in preclinical models," Scientific Reports, Apr. 2023, 13(1):5419, 12 pages.
Liu et al., "Elimination of tumor by CD47/PD-L1 dual-targeting fusion protein that engages innate and adaptive immune responses," Mabs, Feb. 2018, 10(2) 315-24.
PCT International Search Report and Written Opinion in International Appln. No. PCT/CN2024/096554, mailed on Sep. 5, 2024, 16 pages.

Pettinato, "Introduction to antibody-drug conjugates. Antibodies," Oct. 2021, 10(4):42, 11 pages.
Wang et al., "Tumor-selective blockade of CD47 signaling with a CD47/PD-L1 bispecific antibody for enhanced anti-tumor activity and limited toxicity, " Cancer Immunology, Immunotherapy, Feb. 2021, 70:365-76.
EP Partial Supplementary European Search Report in European Appln. No. 22912284.1, mailed on Mar. 31, 2025, 21 pages.
EP Office Action in European Appln. No. 24150099.0, mailed on Dec. 17, 2017, 8 pages.
Uniprot ID No. A0A6P8PA34, "Serine/threonine-protein kinase receptor," Dec. 14, 2022, 7 pages.
PCT International Preliminary Report on Patentability in International Appln. No. PCT/CN2023/140179, mailed on Jul. 3, 2025, 8 pages.
PCT International Preliminary Report on Patentability in International Appln. No. PCT/CN2024/096554, mailed on Dec. 2, 2025, 9 pages.
EP Extended European Search Report in European Appln. No. 24737660.1, mailed on Feb. 10, 2026, 10 pages.

* cited by examiner

| | SPT_G4_v5 | SPT_G1_v5 | PST_G1_v5 | SP_G4_v5 | SP_G1_v5 | PS_G1_v5 | anti-PD-L1 VHH 2H4 |
|---|---|---|---|---|---|---|---|
| EC50 (nM) | 0.36 | 1.57 | 0.32 | 0.48 | 0.31 | 0.28 | 0.22 |
| R square | 1.00 | 1.00 | 1.00 | 1.00 | 1.00 | 1.00 | 1.00 |

(A)

(B)

(C)

(D)

(E)

(F)

(G)

(H)

(I)

(J)

(K)

| | SPT_G4_v5 | SPT_G1_v5 | PST_G1_v5 | SP_G4_v5 | SP_G1_v5 | PS_G1_v5 | HCB101 | Hu5F9-G4 |
|---|---|---|---|---|---|---|---|---|
| IC50 (nM) | 1.139 | 1.18 | 1.281 | 0.9994 | 0.694 | 1.201 | 0.9589 | 0.963 |
| R square | 0.9946 | 0.9962 | 0.9933 | 0.9887 | 0.9821 | 0.9952 | 0.9895 | 0.9964 |

FIG. 12

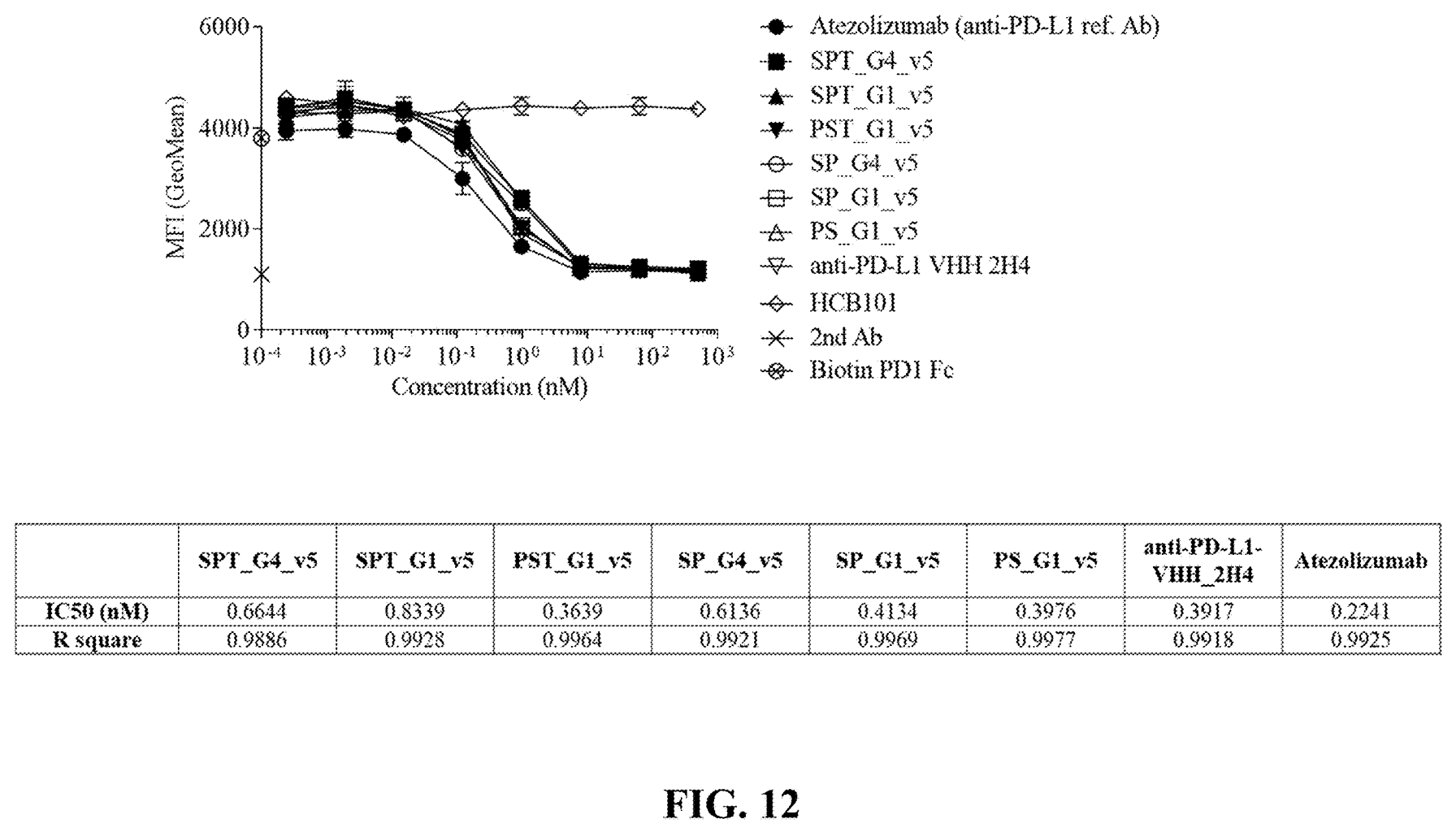

| | SPT_G4_v5 | SPT_G1_v5 | PST_G1_v5 | SP_G4_v5 | SP_G1_v5 | PS_G1_v5 | anti-PD-L1-VHH_2H4 | Atezolizumab |
|---|---|---|---|---|---|---|---|---|
| IC50 (nM) | 0.6644 | 0.8339 | 0.3639 | 0.6136 | 0.4134 | 0.3976 | 0.3917 | 0.2241 |
| R square | 0.9886 | 0.9928 | 0.9964 | 0.9921 | 0.9969 | 0.9977 | 0.9918 | 0.9925 |

FIG. 16

Kabat CDR for anti-PD-L1 VHH 2H4

| VHH CDR1 | SEQ ID NO: | VHH CDR2 | SEQ ID NO: | VHH CDR3 | SEQ ID NO: |
|---|---|---|---|---|---|
| SYAMG | 26 | AIRWNGISTFYADSVKG | 27 | AQTIVTVPENYHFDY | 28 |

Chothia CDR for anti-PD-L1 VHH 2H4

| VHH CDR1 | SEQ ID NO: | VHH CDR2 | SEQ ID NO: | VHH CDR3 | SEQ ID NO: |
|---|---|---|---|---|---|
| GGPFMSY | 29 | RWNGIS | 30 | AQTIVTVPENYHFDY | 31 |

FIG. 17

Amino acid sequence of SPT_G4_v5 (SEQ ID NO: 1)
EEELQVIQPDKSVSVAAGESAILTCTVTSLYPVGPIQWFRGAGPARELIYNQKRQTFPRVTTVSESTKRF
NMDFSISISNITPADAGTYYCVKFRKGSPDTEFKSGAGTELSVRAKPSGSGGSGGSGGSGGSGGSGQVQL
VESGGGVVQPGRSLRLSCAASGGPFMSYAMGWFRQAPGKEREFVAAIRWNGISTFYADSVKGRFTISRDN
SKNTLYLQMNSLRAEDTAVYYCAAAQTIVTVPENYHFDYWGQGTQVTVSSESKYGPPCPPCPAPEFLGGP
SVFLFPPKPKDTLMISRTPEVTCVVVDVSQEDPEVQFNWYVDGVEVHNAKTKPREEQFNSTYRVVSVLTV
LHQDWLNGKEYKCKVSNKGLPSSIEKTISKAKGQPREPQVYTLPPSQEEMTKNQVSLTCLVKGFYPSDIA
VEWESNGQPENNYKTTPPVLDSDGSFFLYSRLTVDKSRWQEGNVFSCSVMHEALHNHYTQKSLSLSLGA**G
GGGSGGGGSGGGGSGGGGSG**IPPHVQKSVNNDMIVTDNNGAVKFPQLCKFCDVRFSTCDNQKSCMSNCEI
TSICEKPQEVCVAVWRKNDENITLETVCHDPKLPYHDFILEDAASPKCIMKEKKKPGETFFMCSCSSEEC
NDNIIFSEEYNTSNPD

Amino acid sequence of SPT_G1_v5 (SEQ ID NO: 2)
EEELQVIQPDKSVSVAAGESAILTCTVTSLYPVGPIQWFRGAGPARELIYNQKRQTFPRVTTVSESTKRF
NMDFSISISNITPADAGTYYCVKFRKGSPDTEFKSGAGTELSVRAKPSGSGGSGGSGGSGGSGGSGQVQL
VESGGGVVQPGRSLRLSCAASGGPFMSYAMGWFRQAPGKEREFVAAIRWNGISTFYADSVKGRFTISRDN
SKNTLYLQMNSLRAEDTAVYYCAAAQTIVTVPENYHFDYWGQGTQVTVSSEPKSSDKTHTCPPCPAPELL
GGPSVFLFPPKPKDTLMISRTPEVTCVVVDVSHEDPEVKFNWYVDGVEVHNAKTKPREEQYNSTYRVVSV
LTVLHQDWLNGKEYKCKVSNKALPAPIEKTISKAKGQPREPQVYTLPPSRDELTKNQVSLTCLVKGFYPS
DIAVEWESNGQPENNYKTTPPVLDSDGSFFLYSKLTVDKSRWQQGNVFSCSVMHEALHNHYTQKSLSLSP
GAGGGGSGGGGSGGGGSGGGGSGIPPHVQKSVNNDMIVTDNNGAVKFPQLCKFCDVRFSTCDNQKSCMSN
CEITSICEKPQEVCVAVWRKNDENITLETVCHDPKLPYHDFILEDAASPKCIMKEKKKPGETFFMCSCSS
EECNDNIIFSEEYNTSNPD

Amino acid sequence of PST_G1_v5 (SEQ ID NO: 3)
QVQLVESGGGVVQPGRSLRLSCAASGGPFMSYAMGWFRQAPGKEREFVAAIRWNGISTFYADSVKGRFTI
SRDNSKNTLYLQMNSLRAEDTAVYYCAAAQTIVTVPENYHFDYWGQGTQVTVSS**GSGGSGGSGGSGGSGG
SG**EEELQVIQPDKSVSVAAGESAILTCTVTSLYPVGPIQWFRGAGPARELIYNQKRQTFPRVTTVSESTK
RFNMDFSISISNITPADAGTYYCVKFRKGSPDTEFKSGAGTELSVRAKPSEPKSSDKTHTCPPCPAPELL
GGPSVFLFPPKPKDTLMISRTPEVTCVVVDVSHEDPEVKFNWYVDGVEVHNAKTKPREEQYNSTYRVVSV
LTVLHQDWLNGKEYKCKVSNKALPAPIEKTISKAKGQPREPQVYTLPPSRDELTKNQVSLTCLVKGFYPS
DIAVEWESNGQPENNYKTTPPVLDSDGSFFLYSKLTVDKSRWQQGNVFSCSVMHEALHNHYTQKSLSLSP
GAGGGGSGGGGSGGGGSGGGGSGIPPHVQKSVNNDMIVTDNNGAVKFPQLCKFCDVRFSTCDNQKSCMSN
CEITSICEKPQEVCVAVWRKNDENITLETVCHDPKLPYHDFILEDAASPKCIMKEKKKPGETFFMCSCSS
EECNDNIIFSEEYNTSNPD

Amino acid sequence of SP_G4_v5 (SEQ ID NO: 4)
EEELQVIQPDKSVSVAAGESAILTCTVTSLYPVGPIQWFRGAGPARELIYNQKRQTFPRVTTVSESTKRF
NMDFSISISNITPADAGTYYCVKFRKGSPDTEFKSGAGTELSVRAKPSGSGGSGGSGGSGGSGGSGQVQL
VESGGGVVQPGRSLRLSCAASGGPFMSYAMGWFRQAPGKEREFVAAIRWNGISTFYADSVKGRFTISRDN
SKNTLYLQMNSLRAEDTAVYYCAAAQTIVTVPENYHFDYWGQGTQVTVSSESKYGPPCPPCPAPEFLGGP
SVFLFPPKPKDTLMISRTPEVTCVVVDVSQEDPEVQFNWYVDGVEVHNAKTKPREEQFNSTYRVVSVLTV
LHQDWLNGKEYKCKVSNKGLPSSIEKTISKAKGQPREPQVYTLPPSQEEMTKNQVSLTCLVKGFYPSDIA
VEWESNGQPENNYKTTPPVLDSDGSFFLYSRLTVDKSRWQEGNVFSCSVMHEALHNHYTQKSLSLSLGK

Amino acid sequence of SP_G1_v5 (SEQ ID NO: 5)
EEELQVIQPDKSVSVAAGESAILTCTVTSLYPVGPIQWFRGAGPARELIYNQKRQTFPRVTTVSESTKRF
NMDFSISISNITPADAGTYYCVKFRKGSPDTEFKSGAGTELSVRAKPSGSGGSGGSGGSGGSGGSGQVQL
VESGGGVVQPGRSLRLSCAASGGPFMSYAMGWFRQAPGKEREFVAAIRWNGISTFYADSVKGRFTISRDN

FIG. 17 Cont.

SKNTLYLQMNSLRAEDTAVYYCAAAQTIVTVPENYHFDYWGQGTQVTVSSEPKSSDKTHTCPPCPAPELL
GGPSVFLFPPKPKDTLMISRTPEVTCVVVDVSHEDPEVKFNWYVDGVEVHNAKTKPREEQYNSTYRVVSV
LTVLHQDWLNGKEYKCKVSNKALPAPIEKTISKAKGQPREPQVYTLPPSRDELTKNQVSLTCLVKGFYPS
DIAVEWESNGQPENNYKTTPPVLDSDGSFFLYSKLTVDKSRWQQGNVFSCSVMHEALHNHYTQKSLSLSP
GK

Amino acid sequence of PS_G1_v5 (SEQ ID NO: 6)
QVQLVESGGGVVQPGRSLRLSCAASGGPFMSYAMGWFRQAPGKEREFVAAIRWNGISTFYADSVKGRFTI
SRDNSKNTLYLQMNSLRAEDTAVYYCAAAQTIVTVPENYHFDYWGQGTQVTVSSGSGGSGGSGGSGGSGG
SGEEELQVIQPDKSVSVAAGESAILTCTVTSLYPVGPIQWFRGAGPARELIYNQKRQTFPRVTTVSESTK
RFNMDFSISISNITPADAGTYYCVKFRKGSPDTEFKSGAGTELSVRAKPSEPKSSDKTHTCPPCPAPELL
GGPSVFLFPPKPKDTLMISRTPEVTCVVVDVSHEDPEVKFNWYVDGVEVHNAKTKPREEQYNSTYRVVSV
LTVLHQDWLNGKEYKCKVSNKALPAPIEKTISKAKGQPREPQVYTLPPSRDELTKNQVSLTCLVKGFYPS
DIAVEWESNGQPENNYKTTPPVLDSDGSFFLYSKLTVDKSRWQQGNVFSCSVMHEALHNHYTQKSLSLSP
GK

SIRPα_mt10 (no Fc region)(SEQ ID NO: 7)
EEELQVIQPDKSVSVAAGESAILTCTVTSLYPVGPIQWFRGAGPARELIYNQKRQTFPRVTTVSESTKRF
NMDFSISISNITPADAGTYYCVKFRKGSPDTEFKSGAGTELSVRAKPS

Anti-PD-L1 VHH 2H4 (no Fc region)(SEQ ID NO: 8)
QVQLVESGGGVVQPGRSLRLSCAASGGPFMSYAMGWFRQAPGKEREFVAAIRWNGISTFYADSVKGRFTI
SRDNSKNTLYLQMNSLRAEDTAVYYCAAAQTIVTVPENYHFDYWGQGTQVTVSS

TGFβRII_mt4 (no Fc region)(SEQ ID NO: 9)
IPPHVQKSVNNDMIVTDNNGAVKFPQLCKFCDVRFSTCDNQKSCMSNCEITSICEKPQEVCVAVWRKNDE
NITLETVCHDPKLPYHDFILEDAASPKCIMKEKKKPGETFFMCSCSSEECNDNIIFSEEYNTSNPD

Human IgG4 Fc region (S228P) containing Hinge region (SEQ ID NO: 10)
ESKYGPPCPPCPAPEFLGGPSVFLFPPKPKDTLMISRTPEVTCVVVDVSQEDPEVQFNWYVDGVEVHNAK
TKPREEQFNSTYRVVSVLTVLHQDWLNGKEYKCKVSNKGLPSSIEKTISKAKGQPREPQVYTLPPSQEEM
TKNQVSLTCLVKGFYPSDIAVEWESNGQPENNYKTTPPVLDSDGSFFLYSRLTVDKSRWQEGNVFSCSVM
HEALHNHYTQKSLSLSLG

Human IgG1 Fc region containing Hinge region (SEQ ID NO: 11)
EPKSSDKTHTCPPCPAPELLGGPSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIEKTISKAKGQPREPQVYTLPPSR
DELTKNQVSLTCLVKGFYPSDIAVEWESNGQPENNYKTTPPVLDSDGSFFLYSKLTVDKSRWQQGNVFSC
SVMHEALHNHYTQKSLSLSPG

Linker peptide (GSG)₆ (SEQ ID NO: 12)
GSGGSGGSGGSGGSGGSG

Linker peptide (G4S)₄G (SEQ ID NO: 13)
GGGGSGGGGSGGGGSGGGGSG

Human IgG4 hinge region (S228P) (SEQ ID NO: 14)
ESKYGPPCPPCP

Human IgG4 Fc region (SEQ ID NO: 15)
APEFLGGPSVFLFPPKPKDTLMISRTPEVTCVVVDVSQEDPEVQFNWYVDGVEVHNAKTKPREEQFNSTY
RVVSVLTVLHQDWLNGKEYKCKVSNKGLPSSIEKTISKAKGQPREPQVYTLPPSQEEMTKNQVSLTCLVK

FIG. 17 Cont.

GFYPSDIAVEWESNGQPENNYKTTPPVLDSDGSFFLYSRLTVDKSRWQEGNVFSCSVMHEALHNHYTQKS
LSLSLG

Human IgG1 hinge region (S228P) (SEQ ID NO: 16)
EPKSSDKTHTCPPCP

Human IgG1 Fc region (SEQ ID NO: 17)
APELLGGPSVFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSRDELTKNQVSLTCLVK
GFYPSDIAVEWESNGQPENNYKTTPPVLDSDGSFFLYSKLTVDKSRWQQGNVFSCSVMHEALHNHYTQKS
LSLSPG

Linker peptide 1 (SEQ ID NO: 18)
GGGGS

Linker peptide 2 (SEQ ID NO: 19)
GSGGSG

HCB101 (SEQ ID NO: 20)
EEELQVIQPDKSVSVAAGESAILTCTVTSLYPVGPIQWFRGAGPARELIYNQKRQTFPRVTTVSESTKRF
NMDFSISISNITPADAGTYYCVKFRKGSPDTEFKSGAGTELSVRAKPSESKYGPPCPPCPAPEFLGGPSV
FLFPPKPKDTLMISRTPEVTCVVVDVSQEDPEVQFNWYVDGVEVHNAKTKPREEQFNSTYRVVSVLTVLH
QDWLNGKEYKCKVSNKGLPSSIEKTISKAKGQPREPQVYTLPPSQEEMTKNQVSLTCLVKGFYPSDIAVE
WESNGQPENNYKTTPPVLDSDGSFFLYSRLTVDKSRWQEGNVFSCSVMHEALHNHYTQKSLSLSLGK

G4_TGFβRII_mt4 (SEQ ID NO: 21)
ESKYGPPCPPCPAPEFLGGPSVFLFPPKPKDTLMISRTPEVTCVVVDVSQEDPEVQFNWYVDGVEVHNAK
TKPREEQFNSTYRVVSVLTVLHQDWLNGKEYKCKVSNKGLPSSIEKTISKAKGQPREPQVYTLPPSQEEM
TKNQVSLTCLVKGFYPSDIAVEWESNGQPENNYKTTPPVLDSDGSFFLYSRLTVDKSRWQEGNVFSCSVM
HEALHNHYTQKSLSLSLGAGGGGSGGGGSGGGGSGGGGSGIPPHVQKSVNNDMIVTDNNGAVKFPQLCKF
CDVRFSTCDNQKSCMSNCEITSICEKPQEVCVAVWRKNDENITLETVCHDPKLPYHDFILEDAASPKCIM
KEKKKPGETFFMCSCSSEECNDNIIFSEEYNTSNPD

G1_TGFβRII_mt4 (SEQ ID NO: 22)
EPKSSDKTHTCPPCPAPELLGGPSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIEKTISKAKGQPREPQVYTLPPSR
DELTKNQVSLTCLVKGFYPSDIAVEWESNGQPENNYKTTPPVLDSDGSFFLYSKLTVDKSRWQQGNVFSC
SVMHEALHNHYTQKSLSLSPGAGGGGSGGGGSGGGGSGGGGSGIPPHVQKSVNNDMIVTDNNGAVKFPQL
CKFCDVRFSTCDNQKSCMSNCEITSICEKPQEVCVAVWRKNDENITLETVCHDPKLPYHDFILEDAASPK
CIMKEKKKPGETFFMCSCSSEECNDNIIFSEEYNTSNPD

SIRPα_G4 (SEQ ID NO: 23)
EEELQVIQPDKSVSVAAGESAILHCTVTSLIPVGPIQWFRGAGPARELIYNQKEGHFPRVTTVSESTKRE
NMDFSISISNITPADAGTYYCVKFRKGSPDTEFKSGAGTELSVRAKPSESKYGPPCPPCPAPEFLGGPSV
FLFPPKPKDTLMISRTPEVTCVVVDVSQEDPEVQFNWYVDGVEVHNAKTKPREEQFNSTYRVVSVLTVLH
QDWLNGKEYKCKVSNKGLPSSIEKTISKAKGQPREPQVYTLPPSQEEMTKNQVSLTCLVKGFYPSDIAVE
WESNGQPENNYKTTPPVLDSDGSFFLYSRLTVDKSRWQEGNVFSCSVMHEALHNHYTQKSLSLSLGK

Human SIRPα amino acid sequence AAH26692.1 (SEQ ID NO: 24)

FIG. 17 Cont.

MEPAGPAPGRLGPLLCLLLAASCAWSGVAGEEELQVIQPDKSVSVAAGESAILHCTVTSLIPVGPIQWFR
GAGPARELIYNQKEGHFPRVTTVSESTKRENMDFSISISNITPADAGTYYCVKFRKGSPDTEFKSGAGTE
LSVRAKPSAPVVSGPAARATPQHTVSFTCESHGFSPRDITLKWFKNGNELSDFQTNVDPVGESVSYSIHS
TAKVVLTREDVHSQVICEVAHVTLQGDPLRGTANLSETIRVPPTLEVTQQPVRAENQVNVTCQVRKFYPQ
RLQLTWLENGNVSRTETASTVTENKDGTYNWMSWLLVNVSAHRDDVKLTCQVEHDGQPAVSKSHDLKVSA
HPKEQGSNTAAENTGSNERNIYIVVGVVCTLLVALLMAALYLVRIRQKKAQGSTSSTRLHEPEKNAREIT
QVQSLDTNDITYADLNLPKGKKPAPQAAEPNNHTEYASIQTSPQPASEDTLTYADLDMVHLNRTPKQPAP
KPEPSFSEYASVQVPRK

Human TGFBR2 amino acid sequence NP_003233.4 (SEQ ID NO: 25)
MGRGLLRGLWPLHIVLWTRIASTIPPHVQKSVNNDMIVTDNNGAVKFPQLCKFCDVRFSTCDNQKSCMSN
CSITSICEKPQEVCVAVWRKNDENITLETVCHDPKLPYHDFILEDAASPKCIMKEKKKPGETFFMCSCSS
DECNDNIIFSEEYNTSNPDLLLVIFQVTGISLLPPLGVAISVIIIFYCYRVNRQQKLSSTWETGKTRKLM
EFSEHCAIILEDDRSDISSTCANNINHNTELLPIELDTLVGKGRFAEVYKAKLKQNTSEQFETVAVKIFP
YEEYASWKTEKDIFSDINLKHENILQFLTAEERKTELGKQYWLITAFHAKGNLQEYLTRHVISWEDLRKL
GSSLARGIAHLHSDHTPCGRPKMPIVHRDLKSSNILVKNDLTCCLCDFGLSLRLDPTLSVDDLANSGQVG
TARYMAPEVLESRMNLENVESFKQTDVYSMALVLWEMTSRCNAVGEVKDYEPPFGSKVREHPCVESMKDN
VLRDRGRPEIPSFWLNHQGIQMVCETLTECWDHDPEARLTAQCVAERFSELEHLDRLSGRSCSEEKIPED
GSLNTTK

Wild-type human SIRPα extracellular domain (SEQ ID NO: 32)
EEELQVIQPDKSVSVAAGESAILHCTVTSLIPVGPIQWFRGAGPARELIYNQKEGHFPRVTTVSESTKRE
NMDFSISISNITPADAGTYYCVKFRKGSPDTEFKSGAGTELSVRAKPS

Wild-type human TGFBR2 extracellular domain (SEQ ID NO: 33)
IPPHVQKSVNNDMIVTDNNGAVKFPQLCKFCDVRFSTCDNQKSCMSNCSITSICEKPQEVCVAVWRKNDE
NITLETVCHDPKLPYHDFILEDAASPKCIMKEKKKPGETFFMCSCSSDECNDNIIFSEEYNTSNPD

PD1_G4 (SEQ ID NO: 34)
DSPDRPWNPPTFSPALLVVTEGDNATFTCSFSNTSESFVLNWYRMSPSNQTDKLAAFPEDRSQPGQDCRF
RVTQLPNGRDFHMSVVRARRNDSGTYLCGAISLAPKAQIKESLRAELRVTERRAEVPTAHPSPSPRPAGQ
FQTLVESKYGPPCPPCPAPEFLGGPSVFLFPPKPKDTLMISRTPEVTCVVVDVSQEDPEVQFNWYVDGVE
VHNAKTKPREEQFNSTYRVVSVLTVLHQDWLNGKEYKCKVSNKGLPSSIEKTISKAKGQPREPQVYTLPP
SQEEMTKNQVSLTCLVKGFYPSDIAVEWESNGQPENNYKTTPPVLDSDGSFFLYSRLTVDKSRWQEGNVF
SCSVMHEALHNHYTQKSLSLSLGK

PDGFR-Fc (SEQ ID NO: 35)
QLSLPSILPNENEKVVQLNSSFSLRCFGESEVSWQYPMSEEESSDVEIRNEENNSGLFVTVLEVSSASAA
HTGLYTCYYNHTQTEENELEGRHIYIYVPDPDVAFVPLGMTDYLVIVEDDDSAIIPCRTTDPETPVTLHN
SEGVVPASYDSRQGFNGTFTVGPYICEATVKGKKFQTIPFNVYALKATSELDLEMEALKTVYKSGETIVV
TCAVFNNEVVDLQWTYPGEVKGKGITMLEEIKVPSIKLVYTLTVPEATVKDSGDYECAARQATREVKEMK
KVTISVHEKGFIEIKPTFSQLEAVNLHEVKHFVVEVRAYPPPRISWLKNNLTLIENLTEITTDVEKIQEI
RYRSKLKLIRAKEEDSGHYTIVAQNEDAVKSYTFELLTQVPSSILDLVDDHHGSTGGQTVRCTAEGTPLP
DIEWMICKDIKKCNNETSWTILANNVSNIITEIHSRDRSTVEGRVTFAKVEETIAVRCLAKNLLGAENRE
LKLVAPTLRSENSDPRRASIEGRGDPEEPKSCDKTHTCPPCPAPELLGGPSVFLFPPKPKDTLMISRTPE
VTCVVVDVSHEDPEVKFNWYVDGVEVHNAKTKPREEQYNSTYRVVSVLTVLHQDWLNGKEYKCKVSNKAL
PAPIEKTISKAKGQPREPQVYTLPPSRDELTKNQVSLTCLVKGFYPSDIAVEWESNGQPENNYKTTPPVL
DSDGSFFLYSKLTVDKSRWQQGNVFSCSVMHEALHNHYTQKSLSLSPGK

H1G4 heavy chain (SEQ ID NO: 36)

FIG. 17 Cont.

QVQLVESGGGLVKPGGSLRLSCAASGFTFSNYGMSWIRQAPGKGLEWVSTISGGGSNIYYADSVKGRFTI
SRDNAKNSLYLQMNSLRAEDTAVYYCVSYYYGIDFWGQGTSVTVSSASTKGPSVFPLAPCSRSTSESTAA
LGCLVKDYFPEPVTVSWNSGALTSGVHTFPAVLQSSGLYSLSSVVTVPSSSLGTKTYTCNVDHKPSNTKV
DKRVESKYGPPCPPCPAPEFLGGPSVFLFPPKPKDTLMISRTPEVTCVVVDVSQEDPEVQFNWYVDGVEV
HNAKTKPREEQFNSTYRVVSVLTVLHQDWLNGKEYKCKVSNKGLPSSIEKTISKAKGQPREPQVYTLPPS
QEEMTKNQVSLTCLVKGFYPSDIAVEWESNGQPENNYKTTPPVLDSDGSFFLYSRLTVDKSRWQEGNVFS
CSVMHEALHNHYTQKSLSLSLGK

H1G4 light chain (SEQ ID NO: 37)
DIQMTQSPSSLSASVGDRVTITCKASQDVTTAVAWYQQKPGKAPKLLIYWASTRHTGVPSRFSGSGSGTD
FTLTISSLQPEDFATYYCQQHYTIPWTFGGGTKLEIKRTVAAPSVFIFPPSDEQLKSGTASVVCLLNNFY
PREAKVQWKVDNALQSGNSQESVTEQDSKDSTYSLSSTLTLSKADYEKHKVYACEVTHQGLSSPVTKSFN
RGEC

SEQUENCE LISTING

```
Sequence total quantity: 37
SEQ ID NO: 1              moltype = AA  length = 646
FEATURE                   Location/Qualifiers
source                    1..646
                          mol_type = protein
                          organism = synthetic construct
SEQUENCE: 1
EEELQVIQPD KSVSVAAGES AILTCTVTSL YPVGPIQWFR GAGPARELIY NQKRQTFPRV  60
TTVSESTKRF NMDFSISISN ITPADAGTYY CVKFRKGSPD TEFKSGAGTE LSVRAKPSGS  120
GGSGGSGGSG GSGGGSGQVQL VESGGGVVQP GRSLRLSCAA SGGPFMSYAM GWFRQAPGKE  180
REFVAAIRWN GISTFYADSV KGRFTISRDN SKNTLYLQMN SLRAEDTAVY YCAAAQTIVT  240
VPENYHFDYW GQGTQVTVSS ESKYGPPCPP CPAPEFLGGP SVFLFPPKPK DTLMISRTPE  300
VTCVVVDVSQ EDPEVQFNWY VDGVEVHNAK TKPREEQFNS TYRVVSVLTV LHQDWLNGKE  360
YKCKVSNKGL PSSIEKTISK AKGQPREPQV YTLPPSQEEM TKNQVSLTCL VKGFYPSDIA  420
VEWESNGQPE NNYKTTPPVL DSDGSFFLYS RLTVDKSRWQ EGNVFSCSVM HEALHNHYTQ  480
KSLSLSLGAG GGGSGGGGSG GGGSGGGGSG IPPHVQKSVN NDMIVTDNNG AVKFPQLCKF  540
CDVRFSTCDN QKSCMSNCEI TSICEKPQEV CVAVWRKNDE NITLETVCHD PKLPYHDFIL  600
EDAASPKCIM KEKKKPGETF FMCSCSSEEC NDNIIFSEEY NTSNPD            646

SEQ ID NO: 2              moltype = AA  length = 649
FEATURE                   Location/Qualifiers
source                    1..649
                          mol_type = protein
                          organism = synthetic construct
SEQUENCE: 2
EEELQVIQPD KSVSVAAGES AILTCTVTSL YPVGPIQWFR GAGPARELIY NQKRQTFPRV  60
TTVSESTKRF NMDFSISISN ITPADAGTYY CVKFRKGSPD TEFKSGAGTE LSVRAKPSGS  120
GGSGGSGGSG GSGGGSGQVQL VESGGGVVQP GRSLRLSCAA SGGPFMSYAM GWFRQAPGKE  180
REFVAAIRWN GISTFYADSV KGRFTISRDN SKNTLYLQMN SLRAEDTAVY YCAAAQTIVT  240
VPENYHFDYW GQGTQVTVSS EPKSSDKTHT CPPCPAPELL GGPSVFLFPP KPKDTLMISR  300
TPEVTCVVVD VSHEDPEVKF NWYVDGVEVH NAKTKPREEQ YNSTYRVVSV LTVLHQDWLN  360
GKEYKCKVSN KALPAPIEKT ISKAKGQPRE PQVYTLPPSR DELTKNQVSL TCLVKGFYPS  420
DIAVEWESNG QPENNYKTTP PVLDSDGSFF LYSKLTVDKS RWQQGNVFSC SVMHEALHNH  480
```

```
YTQKSLSLSP GAGGGGSGGG GSGGGGSGGG GSGIPPHVQK SVNNDMIVTD NNGAVKFPQL   540
CKFCDVRFST CDNQKSCMSN CEITSICEKP QEVCVAVWRK NDENITLETV CHDPKLPYHD   600
FILEDAASPK CIMKEKKKPG ETFFMCSCSS EECNDNIIFS EEYNTSNPD              649

SEQ ID NO: 3                moltype = AA   length = 649
FEATURE                     Location/Qualifiers
source                      1..649
                            mol_type = protein
                            organism = synthetic construct
SEQUENCE: 3
QVQLVESGGG VVQPGRSLRL SCAASGGPFM SYAMGWFRQA PGKEREFVAA IRWNGISTFY   60
ADSVKGRFTI SRDNSKNTLY LQMNSLRAED TAVYYCAAAQ TIVTVPENYH FDYWGQGTQV   120
TVSSGSGGSG GSGGGSGGGG SGEEELQVIQ PDKSVSVAAG ESAILTCTVT SLYPVGPIQW   180
FRGAGPAREL IYNQKRQTFP RVTTVSESTK RFNMDFSISI SNITPADAGT YYCVKFRKGS   240
PDTEFKSGAG TELSVRAKPS EPKSSDKTHT CPPCPAPELL GGPSVFLFPP KPKDTLMISR   300
TPEVTCVVVD VSHEDPEVKF NWYVDGVEVH NAKTKPREEQ YNSTYRVVSV LTVLHQDWLN   360
GKEYKCKVSN KALPAPIEKT ISKAKGQPRE PQVYTLPPSR DELTKNQVSL TCLVKGFYPS   420
DIAVEWESNG QPENNYKTTP PVLDSDGSFF LYSKLTVDKS RWQQGNVFSC SVMHEALHNH   480
YTQKSLSLSP GAGGGGSGGG GSGGGGSGGG GSGIPPHVQK SVNNDMIVTD NNGAVKFPQL   540
CKFCDVRFST CDNQKSCMSN CEITSICEKP QEVCVAVWRK NDENITLETV CHDPKLPYHD   600
FILEDAASPK CIMKEKKKPG ETFFMCSCSS EECNDNIIFS EEYNTSNPD              649

SEQ ID NO: 4                moltype = AA   length = 489
FEATURE                     Location/Qualifiers
source                      1..489
                            mol_type = protein
                            organism = synthetic construct
SEQUENCE: 4
EEELQVIQPD KSVSVAAGES AILTCTVTSL YPVGPIQWFR GAGPARELIY NQKRQTFPRV   60
TTVSESTKRF NMDFSISISN ITPADAGTYY CVKFRKGSPD TEFKSGAGTE LSVRAKPSGS   120
GGSGGSGGSG GSGGSGQVQL VESGGGVVQP GRSLRLSCAA SGGPFMSYAM GWFRQAPGKE   180
REFVAAIRWN GISTFYADSV KGRFTISRDN SKNTLYLQMN SLRAEDTAVY YCAAAQTIVT   240
VPENYHFDYW GQGTQVTVSS ESKYGPPCPP CPAPEFLGGP SVFLFPPKPK DTLMISRTPE   300
VTCVVVDVSQ EDPEVQFNWY VDGVEVHNAK TKPREEQFNS TYRVVSVLTV LHQDWLNGKE   360
YKCKVSNKGL PSSIEKTISK AKGQPREPQV YTLPPSQEEM TKNQVSLTCL VKGFYPSDIA   420
VEWESNGQPE NNYKTTPPVL DSDGSFFLYS RLTVDKSRWQ EGNVFSCSVM HEALHNHYTQ   480
KSLSLSLGK                                                          489

SEQ ID NO: 5                moltype = AA   length = 492
FEATURE                     Location/Qualifiers
source                      1..492
                            mol_type = protein
                            organism = synthetic construct
SEQUENCE: 5
EEELQVIQPD KSVSVAAGES AILTCTVTSL YPVGPIQWFR GAGPARELIY NQKRQTFPRV   60
TTVSESTKRF NMDFSISISN ITPADAGTYY CVKFRKGSPD TEFKSGAGTE LSVRAKPSGS   120
GGSGGSGGSG GSGGSGQVQL VESGGGVVQP GRSLRLSCAA SGGPFMSYAM GWFRQAPGKE   180
REFVAAIRWN GISTFYADSV KGRFTISRDN SKNTLYLQMN SLRAEDTAVY YCAAAQTIVT   240
VPENYHFDYW GQGTQVTVSS EPKSSDKTHT CPPCPAPELL GGPSVFLFPP KPKDTLMISR   300
TPEVTCVVVD VSHEDPEVKF NWYVDGVEVH NAKTKPREEQ YNSTYRVVSV LTVLHQDWLN   360
GKEYKCKVSN KALPAPIEKT ISKAKGQPRE PQVYTLPPSR DELTKNQVSL TCLVKGFYPS   420
DIAVEWESNG QPENNYKTTP PVLDSDGSFF LYSKLTVDKS RWQQGNVFSC SVMHEALHNH   480
YTQKSLSLSP GK                                                      492

SEQ ID NO: 6                moltype = AA   length = 492
FEATURE                     Location/Qualifiers
source                      1..492
                            mol_type = protein
                            organism = synthetic construct
SEQUENCE: 6
QVQLVESGGG VVQPGRSLRL SCAASGGPFM SYAMGWFRQA PGKEREFVAA IRWNGISTFY   60
ADSVKGRFTI SRDNSKNTLY LQMNSLRAED TAVYYCAAAQ TIVTVPENYH FDYWGQGTQV   120
TVSSGSGGSG GSGGSGGSGG SGEEELQVIQ PDKSVSVAAG ESAILTCTVT SLYPVGPIQW   180
FRGAGPAREL IYNQKRQTFP RVTTVSESTK RFNMDFSISI SNITPADAGT YYCVKFRKGS   240
PDTEFKSGAG TELSVRAKPS EPKSSDKTHT CPPCPAPELL GGPSVFLFPP KPKDTLMISR   300
TPEVTCVVVD VSHEDPEVKF NWYVDGVEVH NAKTKPREEQ YNSTYRVVSV LTVLHQDWLN   360
GKEYKCKVSN KALPAPIEKT ISKAKGQPRE PQVYTLPPSR DELTKNQVSL TCLVKGFYPS   420
DIAVEWESNG QPENNYKTTP PVLDSDGSFF LYSKLTVDKS RWQQGNVFSC SVMHEALHNH   480
YTQKSLSLSP GK                                                      492

SEQ ID NO: 7                moltype = AA   length = 118
FEATURE                     Location/Qualifiers
source                      1..118
                            mol_type = protein
                            organism = synthetic construct
SEQUENCE: 7
EEELQVIQPD KSVSVAAGES AILTCTVTSL YPVGPIQWFR GAGPARELIY NQKRQTFPRV   60
TTVSESTKRF NMDFSISISN ITPADAGTYY CVKFRKGSPD TEFKSGAGTE LSVRAKPS    118
```

49

50

-continued

```
SEQ ID NO: 8            moltype = AA   length = 124
FEATURE                 Location/Qualifiers
source                  1..124
                        mol_type = protein
                        organism = synthetic construct
SEQUENCE: 8
QVQLVESGGG VVQPGRSLRL SCAASGGPFM SYAMGWFRQA PGKEREFVAA IRWNGISTFY   60
ADSVKGRFTI SRDNSKNTLY LQMNSLRAED TAVYYCAAAQ TIVTVPENYH FDYWGQGTQV  120
TVSS                                                               124

SEQ ID NO: 9            moltype = AA   length = 136
FEATURE                 Location/Qualifiers
source                  1..136
                        mol_type = protein
                        organism = synthetic construct
SEQUENCE: 9
IPPHVQKSVN NDMIVTDNNG AVKFPQLCKF CDVRFSTCDN QKSCMSNCEI TSICEKPQEV   60
CVAVWRKNDE NITLETVCHD PKLPYHDFIL EDAASPKCIM KEKKKPGETF FMCSCSSEEC  120
NDNIIFSEEY NTSNPD                                                  136

SEQ ID NO: 10           moltype = AA   length = 136
FEATURE                 Location/Qualifiers
source                  1..136
                        mol_type = protein
                        organism = synthetic construct
SEQUENCE: 10
IPPHVQKSVN NDMIVTDNNG AVKFPQLCKF CDVRFSTCDN QKSCMSNCEI TSICEKPQEV   60
CVAVWRKNDE NITLETVCHD PKLPYHDFIL EDAASPKCIM KEKKKPGETF FMCSCSSEEC  120
NDNIIFSEEY NTSNPD                                                  136

SEQ ID NO: 11           moltype = AA   length = 231
FEATURE                 Location/Qualifiers
source                  1..231
                        mol_type = protein
                        organism = Homo sapiens
SEQUENCE: 11
EPKSSDKTHT CPPCPAPELL GGPSVFLFPP KPKDTLMISR TPEVTCVVVD VSHEDPEVKF   60
NWYVDGVEVH NAKTKPREEQ YNSTYRVVSV LTVLHQDWLN GKEYKCKVSN KALPAPIEKT  120
ISKAKGQPRE PQVYTLPPSR DELTKNQVSL TCLVKGFYPS DIAVEWESNG QPENNYKTTP  180
PVLDSDGSFF LYSKLTVDKS RWQQGNVFSC SVMHEALHNH YTQKSLSLSP G           231

SEQ ID NO: 12           moltype = AA   length = 18
FEATURE                 Location/Qualifiers
source                  1..18
                        mol_type = protein
                        organism = synthetic construct
SEQUENCE: 12
GSGGSGGSGG SGGSGGSG                                                 18

SEQ ID NO: 13           moltype = AA   length = 21
FEATURE                 Location/Qualifiers
source                  1..21
                        mol_type = protein
                        organism = synthetic construct
SEQUENCE: 13
GGGGSGGGGS GGGGSGGGGS G                                             21

SEQ ID NO: 14           moltype = AA   length = 12
FEATURE                 Location/Qualifiers
source                  1..12
                        mol_type = protein
                        organism = synthetic construct
SEQUENCE: 14
ESKYGPPCPP CP                                                       12

SEQ ID NO: 15           moltype = AA   length = 216
FEATURE                 Location/Qualifiers
source                  1..216
                        mol_type = protein
                        organism = Homo sapiens
SEQUENCE: 15
APEFLGGPSV FLFPPKPKDT LMISRTPEVT CVVVDVSQED PEVQFNWYVD GVEVHNAKTK   60
PREEQFNSTY RVVSVLTVLH QDWLNGKEYK CKVSNKGLPS SIEKTISKAK GQPREPQVYT  120
LPPSQEEMTK NQVSLTCLVK GFYPSDIAVE WESNGQPENN YKTTPPVLDS DGSFFLYSRL  180
TVDKSRWQEG NVFSCSVMHE ALHNHYTQKS LSLSLG                            216

SEQ ID NO: 16           moltype = AA   length = 15
FEATURE                 Location/Qualifiers
source                  1..15
```

```
                          mol_type = protein
                          organism = synthetic construct
SEQUENCE: 16
EPKSSDKTHT CPPCP                                                   15

SEQ ID NO: 17           moltype = AA   length = 216
FEATURE                 Location/Qualifiers
source                  1..216
                        mol_type = protein
                        organism = synthetic construct
SEQUENCE: 17
APELLGGPSV FLFPPKPKDT LMISRTPEVT CVVVDVSHED PEVKFNWYVD GVEVHNAKTK  60
PREEQYNSTY RVVSVLTVLH QDWLNGKEYK CKVSNKALPA PIEKTISKAK GQPREPQVYT  120
LPPSRDELTK NQVSLTCLVK GFYPSDIAVE WESNGQPENN YKTTPPVLDS DGSFFLYSKL  180
TVDKSRWQQG NVFSCSVMHE ALHNHYTQKS LSLSPG                            216

SEQ ID NO: 18           moltype = AA   length = 5
FEATURE                 Location/Qualifiers
source                  1..5
                        mol_type = protein
                        organism = synthetic construct
SEQUENCE: 18
GGGGS                                                              5

SEQ ID NO: 19           moltype = AA   length = 6
FEATURE                 Location/Qualifiers
source                  1..6
                        mol_type = protein
                        organism = synthetic construct
SEQUENCE: 19
GSGGSG                                                             6

SEQ ID NO: 20           moltype = AA   length = 347
FEATURE                 Location/Qualifiers
source                  1..347
                        mol_type = protein
                        organism = synthetic construct
SEQUENCE: 20
EEELQVIQPD KSVSVAAGES AILTCTVTSL YPVGPIQWFR GAGPARELIY NQKRQTFPRV  60
TTVSESTKRF NMDFSISISN ITPADAGTYY CVKFRKGSPD TEFKSGAGTE LSVRAKPSES  120
KYGPPCPPCP APEFLGGPSV FLFPPKPKDT LMISRTPEVT CVVVDVSQED PEVQFNWYVD  180
GVEVHNAKTK PREEQFNSTY RVVSVLTVLH QDWLNGKEYK CKVSNKGLPS SIEKTISKAK  240
GQPREPQVYT LPPSQEEMTK NQVSLTCLVK GFYPSDIAVE WESNGQPENN YKTTPPVLDS  300
DGSFFLYSRL TVDKSRWQEG NVFSCSVMHE ALHNHYTQKS LSLSLGK               347

SEQ ID NO: 21           moltype = AA   length = 386
FEATURE                 Location/Qualifiers
source                  1..386
                        mol_type = protein
                        organism = synthetic construct
SEQUENCE: 21
ESKYGPPCPP CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGAG GGGSGGGGSG  240
GGGSGGGGSG IPPHVQKSVN NDMIVTDNNG AVKFPQLCKF CDVRFSTCDN QKSCMSNCEI  300
TSICEKPQEV CVAVWRKNDE NITLETVCHD PKLPYHDFIL EDAASPKCIM KEKKKPGETF  360
FMCSCSSEEC NDNIIFSEEY NTSNPD                                       386

SEQ ID NO: 22           moltype = AA   length = 389
FEATURE                 Location/Qualifiers
source                  1..389
                        mol_type = protein
                        organism = synthetic construct
SEQUENCE: 22
EPKSSDKTHT CPPCPAPELL GGPSVFLFPP KPKDTLMISR TPEVTCVVVD VSHEDPEVKF  60
NWYVDGVEVH NAKTKPREEQ YNSTYRVVSV LTVLHQDWLN GKEYKCKVSN KALPAPIEKT  120
ISKAKGQPRE PQVYTLPPSR DELTKNQVSL TCLVKGFYPS DIAVEWESNG QPENNYKTTP  180
PVLDSDGSFF LYSKLTVDKS RWQQGNVFSC SVMHEALHNH YTQKSLSLSP GAGGGGSGGG  240
GSGGGGSGGG GSGIPPHVQK SVNNDMIVTD NNGAVKFPQL CKFCDVRFST CDNQKSCMSN  300
CEITSICEKP QEVCVAVWRK NDENITLETV CHDPKLPYHD FILEDAASPK CIMKEKKKPG  360
ETFFMCSCSS EECNDNIIFS EEYNTSNPD                                    389

SEQ ID NO: 23           moltype = AA   length = 347
FEATURE                 Location/Qualifiers
source                  1..347
                        mol_type = protein
                        organism = synthetic construct
SEQUENCE: 23
```

```
EEELQVIQPD KSVSVAAGES AILHCTVTSL IPVGPIQWFR GAGPARELIY NQKEGHFPRV   60
TTVSESTKRE NMDFSISISN ITPADAGTYY CVKFRKGSPD TEFKSGAGTE LSVRAKPSES  120
KYGPPCPPCP APEFLGGPSV FLFPPKPKDT LMISRTPEVT CVVVDVSQED PEVQFNWYVD  180
GVEVHNAKTK PREEQFNSTY RVVSVLTVLH QDWLNGKEYK CKVSNKGLPS SIEKTISKAK  240
GQPREPQVYT LPPSQEEMTK NQVSLTCLVK GFYPSDIAVE WESNGQPENN YKTTPPVLDS  300
DGSFFLYSRL TVDKSRWQEG NVFSCSVMHE ALHNHYTQKS LSLSLGK                347

SEQ ID NO: 24              moltype = AA   length = 507
FEATURE                    Location/Qualifiers
source                     1..507
                           mol_type = protein
                           organism = Homo sapiens
SEQUENCE: 24
MEPAGPAPGR LGPLLCLLLA ASCAWSGVAG EEELQVIQPD KSVSVAAGES AILHCTVTSL   60
IPVGPIQWFR GAGPARELIY NQKEGHFPRV TTVSESTKRE NMDFSISISN ITPADAGTYY  120
CVKFRKGSPD TEFKSGAGTE LSVRAKPSAP VVSGPAARAT PQHTVSFTCE SHGFSPRDIT  180
LKWFKNGNEL SDFQTNVDPV GESVSYSIHS TAKVVLTRED VHSQVICEVA HVTLQGDPLR  240
GTANLSETIR VPPTLEVTQQ PVRAENQVNV TCQVRKFYPQ RLQLTWLENG NVSRTETAST  300
VTENKDGTYN WMSWLLVNVS AHRDDVKLTC QVEHDGQPAV SKSHDLKVSA HPKEQGSNTA  360
AENTGSNERN IYIVVGVVCT LLVALLMAAL YLVRIRQKKA QGSTSSTRLH EPEKNAREIT  420
QVQSLDTNDI TYADLNLPKG KKPAPQAAEP NNHTEYASIQ TSPQPASEDT LTYADLDMVH  480
LNRTPKQPAP KPEPSFSEYA SVQVPRK                                      507

SEQ ID NO: 25              moltype = AA   length = 567
FEATURE                    Location/Qualifiers
source                     1..567
                           mol_type = protein
                           organism = Homo sapiens
SEQUENCE: 25
MGRGLLRGLW PLHIVLWTRI ASTIPPHVQK SVNNDMIVTD NNGAVKFPQL CKFCDVRFST   60
CDNQKSCMSN CSITSICEKP QEVCVAVWRK NDENITLETV CHDPKLPYHD FILEDAASPK  120
CIMKEKKKPG ETFFMCSCSS DECNDNIIFS EEYNTSNPDL LLVIFQVTGI SLLPPLGVAI  180
SVIIIFYCYR VNRQQKLSST WETGKTRKLM EFSEHCAIIL EDDRSDISST CANNINHNTE  240
LLPIELDTLV GKGRFAEVYK AKLKQNTSEQ FETVAVKIFP YEEYASWKTE KDIFSDINLK  300
HENILQFLTA EERKTELGKQ YWLITAFHAK GNLQEYLTRH VISWEDLRKL GSSLARGIAH  360
LHSDHTPCGR PKMPIVHRDL KSSNILVKND LTCCLCDFGL SLRLDPTLSV DDLANSGQVG  420
TARYMAPEVL ESRMNLENVE SFKQTDVYSM ALVLWEMTSR CNAVGEVKDY EPPFGSKVRE  480
HPCVESMKDN VLRDRGRPEI PSFWLNHQGI QMVCETLTEC WDHDPEARLT AQCVAERFSE  540
LEHLDRLSGR SCSEEKIPED GSLNTTK                                      567

SEQ ID NO: 26              moltype = AA   length = 5
FEATURE                    Location/Qualifiers
source                     1..5
                           mol_type = protein
                           organism = synthetic construct
SEQUENCE: 26
SYAMG                                                                5

SEQ ID NO: 27              moltype = AA   length = 17
FEATURE                    Location/Qualifiers
source                     1..17
                           mol_type = protein
                           organism = synthetic construct
SEQUENCE: 27
AIRWNGISTF YADSVKG                                                  17

SEQ ID NO: 28              moltype = AA   length = 15
FEATURE                    Location/Qualifiers
source                     1..15
                           mol_type = protein
                           organism = synthetic construct
SEQUENCE: 28
AQTIVTVPEN YHFDY                                                    15

SEQ ID NO: 29              moltype = AA   length = 7
FEATURE                    Location/Qualifiers
source                     1..7
                           mol_type = protein
                           organism = synthetic construct
SEQUENCE: 29
GGPFMSY                                                             7

SEQ ID NO: 30              moltype = AA   length = 6
FEATURE                    Location/Qualifiers
source                     1..6
                           mol_type = protein
                           organism = synthetic construct
SEQUENCE: 30
RWNGIS                                                              6
```

-continued

```
SEQ ID NO: 31          moltype = AA   length = 15
FEATURE                Location/Qualifiers
source                 1..15
                       mol_type = protein
                       organism = synthetic construct
SEQUENCE: 31
AQTIVTVPEN YHFDY                                                       15

SEQ ID NO: 32          moltype = AA   length = 118
FEATURE                Location/Qualifiers
source                 1..118
                       mol_type = protein
                       organism = Homo sapiens
SEQUENCE: 32
EEELQVIQPD KSVSVAAGES AILHCTVTSL IPVGPIQWFR GAGPARELIY NQKEGHFPRV   60
TTVSESTKRE NMDFSISISN ITPADAGTYY CVKFRKGSPD TEFKSGAGTE LSVRAKPS      118

SEQ ID NO: 33          moltype = AA   length = 136
FEATURE                Location/Qualifiers
source                 1..136
                       mol_type = protein
                       organism = Homo sapiens
SEQUENCE: 33
IPPHVQKSVN NDMIVTDNNG AVKFPQLCKF CDVRFSTCDN QKSCMSNCSI TSICEKPQEV   60
CVAVWRKNDE NITLETVCHD PKLPYHDFIL EDAASPKCIM KEKKKPGETF FMCSCSSDEC   120
NDNIIFSEEY NTSNPD                                                      136

SEQ ID NO: 34          moltype = AA   length = 374
FEATURE                Location/Qualifiers
source                 1..374
                       mol_type = protein
                       organism = synthetic construct
SEQUENCE: 34
DSPDRPWNPP TFSPALLVVT EGDNATFTCS FSNTSESFVL NWYRMSPSNQ TDKLAAFPED   60
RSQPGQDCRF RVTQLPNGRD FHMSVVRARR NDSGTYLCGA ISLAPKAQIK ESLRAELRVT   120
ERRAEVPTAH PSPSPRPAGQ FQTLVESKYG PPCPPCPAPE FLGGPSVFLF PPKPKDTLMI   180
SRTPEVTCVV VDVSQEDPEV QFNWYVDGVE VHNAKTKPRE EQFNSTYRVV SVLTVLHQDW   240
LNGKEYKCKV SNKGLPSSIE KTISKAKGQP REPQVYTLPP SQEEMTKNQV SLTCLVKGFY   300
PSDIAVEWES NGQPENNYKT TPPVLDSDGS FFLYSRLTVD KSRWQEGNVF SCSVMHEALH   360
NHYTQKSLSL SLGK                                                       374

SEQ ID NO: 35          moltype = AA   length = 749
FEATURE                Location/Qualifiers
source                 1..749
                       mol_type = protein
                       organism = synthetic construct
SEQUENCE: 35
QLSLPSILPN ENEKVVQLNS SFSLRCFGES EVSWQYPMSE EESSDVEIRN EENNSGLFVT   60
VLEVSSASAA HTGLYTCYYN HTQTEENELE GRHIYIYVPD PDVAFVPLGM TDYLVIVEDD   120
DSAIIPCRTT DPETPVTLHN SEGVVPASYD SRQGFNGTFT VGPYICEATV KGKKFQTIPF   180
NVYALKATSE LDLEMEALKT VYKSGETIVV TCAVFNNEVV DLQWTYPGEV KGKGITMLEE   240
IKVPSIKLVY TLTVPEATVK DSGDYECAAR QATREVKEMK KVTISVHEKG FIEIKPTFSQ   300
LEAVNLHEVK HFVVEVRAYP PPRISWLKNN LTLIENLTEI TTDVEKIQEI RYRSKLKLIR   360
AKEEDSGHYT IVAQNEDAVK SYTFELLTQV PSSILDLVHD HHGSTGGQTV RCTAEGTPLP   420
DIEWMICKDI KKCNNETSWT ILANNVSNII TEIHSRDRST VEGRVTFAKV EETIAVRCLA   480
KNLLGAENRE LKLVAPTLRS ENSDPRRASI EGRGDPEEPK SCDKTHTCPP CPAPELLGGP   540
SVFLFPPKPK DTLMISRTPE VTCVVVDVSH EDPEVKFNWY VDGVEVHNAK TKPREEQYNS   600
TYRVSVLTV LHQDWLNGKE YKCKVSNKAL PAPIEKTISK AKGQPREPQV YTLPPSRDEL   660
TKNQVSLTCL VKGFYPSDIA VEWESNGQPE NNYKTTPPVL DSDGSFFLYS KLTVDKSRWQ   720
QGNVFSCSVM HEALHNHYTQ KSLSLSPGK                                       749

SEQ ID NO: 36          moltype = AA   length = 443
FEATURE                Location/Qualifiers
source                 1..443
                       mol_type = protein
                       organism = synthetic construct
SEQUENCE: 36
QVQLVESGGG LVKPGGSLRL SCAASGFTFS NYGMSWIRQA PGKGLEWVST ISGGGSNIYY   60
ADSVKGRFTI SRDNAKNSLY LQMNSLRAED TAVYYCVSYY YGIDFWGQGT SVTVSSASTK   120
GPSVFPLAPC SRSTSESTAA LGCLVKDYFP EPVTVSWNSG ALTSGVHTFP AVLQSSGLYS   180
LSSVVTVPSS SLGTKTYTCN VDHKPSNTKV DKRVESKYGP PCPPCPAPEF LGGPSVFLFP   240
PKPKDTLMIS RTPEVTCVVV DVSQEDPEVQ FNWYVDGVEV HNAKTKPREE QFNSTYRVVS   300
VLTVLHQDWL NGKEYKCKVS NKGLPSSIEK TISKAKGQPR EPQVYTLPPS QEEMTKNQVS   360
LTCLVKGFYP SDIAVEWESN GQPENNYKTT PPVLDSDGSF FLYSRLTVDK SRWQEGNVFS   420
CSVMHEALHN HYTQKSLSLS LGK                                             443

SEQ ID NO: 37          moltype = AA   length = 214
FEATURE                Location/Qualifiers
```

-continued

```
source              1..214
                    mol_type = protein
                    organism = synthetic construct
SEQUENCE: 37
DIQMTQSPSS LSASVGDRVT ITCKASQDVT TAVAWYQQKP GKAPKLLIYW ASTRHTGVPS   60
RFSGSGSGTD FTLTISSLQP EDFATYYCQQ HYTIPWTFGG GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214
```

CD47/PD-L1-TARGETING PROTEIN COMPLEX AND METHODS OF USE THEREOF

CROSS-REFERENCE TO RELATED APPLICATION

This application is a bypass continuation of and claims benefit under 35 U.S.C. § 120 from PCT Application No. PCT/CN2024/096554 filed on May 31, 2024, which claims priority to and benefit of U.S. Provisional Patent Application Ser. No. 63/470,003, filed on May 31, 2023. Each of the foregoing applications is incorporated herein by reference in its entirety.

SEQUENCE LISTING

This application contains a Sequence Listing that has been submitted electronically as an XML file named "52246-001401_ST26_SL.XML." The XML file, created on Jul. 10, 2024, is 42,016 bytes in size. The material in the XML file is hereby incorporated by reference in its entirety.

TECHNICAL FIELD

This disclosure relates to protein complexes targeting CD47 and PD-L1, and methods of use thereof. In some embodiments, the protein complexes also target TGFβ.

BACKGROUND

Signal regulatory protein a (SIRPα) is a regulatory membrane glycoprotein from SIRP family. It is mainly expressed in myeloid cells and additional expression can be detected in stem cells or neurons. SIRPα acts as an inhibitory receptor that interacts with the broadly expressed transmembrane protein CD47. This interaction negatively regulates the effector function of innate immune cells such as host cell phagocytosis. SIRPα diffuses laterally on the macrophage membrane and accumulates at a phagocytic synapse to bind CD47, thereby inhibiting the cytoskeleton-intensive process of phagocytosis by the macrophage. CD47 provides a "do not eat" signal by binding to the N-terminus of signal regulatory protein alpha (SIRPα). CD47 has been found to be overexpressed in many different tumor cells. Targeting CD47 and/or SIRPα can be useful for cancer immunotherapy. However, given that CD47 is also expressed on red blood cells (RBCs) and platelets, inhibiting the CD47/SIRPα interaction may cause the phagocytosis of RBCs and platelets.

Programmed Cell Death Ligand 1 (PD-L1) is a transmembrane protein that is considered to be a co-inhibitory factor in the immune response. It can combine with Programmed Cell Death Protein 1 (PD-1) to reduce the proliferation of PD-1 positive cells, inhibit their cytokine secretion and induce apoptosis. PD-L1 also plays an important role in various malignancies where it can attenuate the host immune response to tumor cells. Thus, PD-1/PD-L1 axis is responsible for cancer immune escape and makes a huge effect on cancer therapy. There is a need to develop therapies targeting CD47/SIRPα pathway and/or PD-1/PD-L1 pathway.

SUMMARY

This disclosure relates to protein complexes targeting CD47 and PD-L1, and methods of use thereof. In some cases, the protein complex can also target TGFβ.

In one aspect, the disclosure is related to a protein complex, comprising: (a) an Fc; (b) a CD47-binding domain; and (c) a PD-L1 (programmed death-ligand 1)-binding domain, in some embodiments, the PD-L1-binding domain is a VHH (heavy chain single variable domain) that binds to PD-L1. In some embodiments, the protein complex described herein further comprises a TGFβ (transforming growth factor beta)-binding domain. In some embodiments, the CD47-binding domain can bind to a cell (e.g., cancer cell) expressing CD47 and/or block the interaction between CD47 and signal regulatory protein a (SIRPα). In some embodiments, the CD47-binding domain is or comprises a SIRPα extracellular domain. In some embodiments, the SIRPα extracellular domain comprises a sequence that is at least 80% identical to SEQ ID NO: 32, optionally in some embodiments, the SIRPα extracellular domain comprises one or more amino acid mutations at positions corresponding to H24, I31, E54, G55, H56, and/or E70 of SEQ ID NO: 32. In some embodiments, the SIRPα extracellular domain comprises one or more of the following: (a) the amino acid that corresponds to H24 of SEQ ID NO: 32 is T; (b) the amino acid that corresponds to 131 of SEQ ID NO: 32 is Y; (c) the amino acid that corresponds to E54 of SEQ ID NO: 32 is R; (d) the amino acid that corresponds to G55 of SEQ ID NO: 32 is Q; (e) the amino acid that corresponds to H56 of SEQ ID NO: 32 is T; and (f) the amino acid that corresponds to E70 of SEQ ID NO: 32 is F. In some embodiments, the CD47-binding domain comprises an amino acid sequence that is at least 80%, 85%, 90%, 95%, 96%, 97%, 98%, 99% or 100% identical to SEQ ID NO: 7. In some embodiments, the VHH can bind to a cell (e.g., cancer cell) expressing PD-L1 and/or block the interaction between PD-L1 and programmed cell death protein 1 (PD-1). In some embodiments, the VHH comprises complementarity determining regions (CDRs) 1, 2, and 3, in some embodiments, the VHH CDR1 region comprises an amino acid sequence that is at least 80% identical to a selected VHH CDR1 amino acid sequence, the VHH CDR2 region comprises an amino acid sequence that is at least 80% identical to a selected VHH CDR2 amino acid sequence, and the VHH CDR3 region comprises an amino acid sequence that is at least 80% identical to a selected VHH CDR3 amino acid sequence; in some embodiments, the selected VHH CDRs 1, 2, and 3 amino acid sequences are one of the following: (1) the selected VHH CDRs 1, 2, 3 amino acid sequences are set forth in SEQ ID NOs: 26, 27, and 28, respectively; and (2) the selected VHH CDRs 1, 2, 3 amino acid sequences are set forth in SEQ ID NOs: 29, 30, and 31, respectively. In some embodiments, the VHH comprises an amino acid sequence that is at least 80%, 85%, 90%, 95%, 96%, 97%, 98%, 99% or 100% identical to SEQ ID NO: 8. In some embodiments, the TGFβ-binding domain can capture TGFβ thereby increasing immune response and/or improving tumor microenvironment. In some embodiments, the TGFβ-binding domain is or comprises a TGFBRII extracellular domain. In some embodiments, the TGFBRII extracellular domain comprises a sequence that is at least 80% identical to SEQ ID NO: 33, optionally in some embodiments, the TGFBRII extracellular domain comprises one or more amino acid mutations at positions corresponding to S49 and/or D118 of SEQ ID NO: 33. In some embodiments, the TGFβ-binding domain comprises one or more of the following: (a) the amino acid that corresponds to S49 of SEQ ID NO: 33 is E; and (b) the amino acid that corresponds to D118 of SEQ ID NO: 33 is E. In some embodiments, the TGFβ-binding domain comprises an amino acid sequence that is at least 80%, 85%, 90%, 95%, 96%, 97%, 98%, 99% or 100% identical to SEQ ID NO: 9.

In some embodiments, the CD47-binding domain is linked to the N-terminus of a CH2 domain in the Fc, optionally via a hinge region. In some embodiments, the PD-L1-binding domain is linked to the N-terminus of the CD47-binding domain, optionally via a linker peptide. In some embodiments, the PD-L1-binding domain is linked to the N-terminus of a CH2 domain in the Fc, optionally via a hinge region. In some embodiments, the CD47-binding domain is linked to the N-terminus of the PD-L1-binding domain, optionally via a linker peptide. In some embodiments, the Fc is human IgG1 Fc. In some embodiments, the Fc is human IgG4 Fc. In some embodiments, the hinge region is a human IgG4 hinge region optionally with S228P mutation according to EU numbering. In some embodiments, the TGFβ-binding domain is linked to the C-terminus of a CH3 domain in the Fc, optionally via a linker peptide.

In one aspect, the disclosure is related to a protein complex, comprising (a) a first polypeptide comprising from N-terminus to C-terminus: a first CD47-binding domain, an optional first linker peptide, a first VHH that binds to PD-L1, an optional first hinge region, a first Fc region; and (b) a second polypeptide comprising from N-terminus to C-terminus: a second CD47-binding domain, an optional second linker peptide, a second VHH that binds to PD-L1, an optional second hinge region, and a second Fc region. In some embodiments, the first VHH and/or the second VHH comprise a sequence that is at least 80%, 90%, 95%, or 100% identical to SEQ ID NO: 8. In some embodiments, the first CD47-binding domain and/or the second CD47-binding domain comprise a sequence that is at least 80%, 90%, 95%, or 100% identical to SEQ ID NO: 7. In some embodiments, the first hinge region and/or the second hinge region comprise a sequence that is at least 80% identical to SEQ ID NO: 14. In some embodiments, the first Fc region and/or the second Fc region comprise a sequence that is at least 80% identical to SEQ ID NO: 15. In some embodiments, the first hinge region and/or the second hinge region comprise a sequence that is at least 80% identical to SEQ ID NO: 16. In some embodiments, the first Fc region and/or the second Fc region comprise a sequence that is at least 80% identical to SEQ ID NO: 17. In some embodiments, the first linker peptide and/or the second linker peptide comprise a sequence that is at least 80% identical to SEQ ID NO: 12. In some embodiments, the first polypeptide and/or the second polypeptide comprise a sequence that is at least 80%, 90%, 95%, or 100% identical to SEQ ID NO: 4 or 5. In some embodiments, the first polypeptide further comprises a first TGFβ-binding domain, and the second polypeptide further comprises a second TGFβ-binding domain. In some embodiments, the first TGFβ-binding domain and/or the second TGFβ-binding domain comprise a sequence that is at least 80%, 90%, 95%, or 100% identical to SEQ ID NO: 9. In some embodiments, the first TGFβ-binding domain is linked to the C-terminus of the first Fc region, optionally via a third linker peptide, in some embodiments, the second TGFβ-binding domain is linked to the C-terminus of the second Fc region, optionally via a fourth linker peptide. In some embodiments, the third linker peptide and/or the fourth linker peptide comprise a sequence that is at least 80% identical to SEQ ID NO: 13. In some embodiments, the first polypeptide and/or the second polypeptide comprise a sequence that is at least 80%, 90%, 95%, or 100% identical to SEQ ID NO: 1 or 2.

In one aspect, the disclosure is related to a protein complex, comprising (a) a first polypeptide comprising from N-terminus to C-terminus: a first VHH that binds to PD-L1, an optional first linker peptide, a first CD47-binding domain, an optional first hinge region, a first Fc region; and (b) a second polypeptide comprising from N-terminus to C-terminus: a second VHH that binds to PD-L1, an optional second linker peptide, a second CD47-binding domain, an optional second hinge region, and a second Fc region. In some embodiments, the first VHH and/or the second VHH comprise a sequence that is at least 80%, 90%, 95%, or 100% identical to SEQ ID NO: 8. In some embodiments, the first CD47-binding domain and/or the second CD47-binding domain comprise a sequence that is at least 80%, 90%, 95%, or 100% identical to SEQ ID NO: 7. In some embodiments, the first hinge region and/or the second hinge region comprise a sequence that is at least 80% identical to SEQ ID NO: 16. In some embodiments, the first Fc region and/or the second Fc region comprise a sequence that is at least 80% identical to SEQ ID NO: 17. In some embodiments, the first linker peptide and/or the second linker peptide comprise a sequence that is at least 80% identical to SEQ ID NO: 12. In some embodiments, the first polypeptide and/or the second polypeptide comprise a sequence that is at least 80%, 90%, 95%, or 100% identical to SEQ ID NO: 6. In some embodiments, the first polypeptide further comprises a first TGFβ-binding domain, and the second polypeptide further comprises a second TGFβ-binding domain. In some embodiments, the first TGFβ-binding domain and/or the second TGFβ-binding domain comprise a sequence that is at least 80%, 90%, 95%, or 100% identical to SEQ ID NO: 9. In some embodiments, the first TGFβ-binding domain is linked to the C-terminus of the first Fc region, optionally via a third linker peptide, in some embodiments, the second TGFβ-binding domain is linked to the C-terminus of the second Fc region, optionally via a fourth linker peptide. In some embodiments, the third linker peptide and/or the fourth linker peptide comprise a sequence that is at least 80% identical to SEQ ID NO: 13. In some embodiments, the first polypeptide and/or the second polypeptide comprise a sequence that is at least 80%, 90%, 95%, or 100% identical to SEQ ID NO: 3.

In one aspect, the disclosure is related to a nucleic acid comprising a polynucleotide encoding the protein complex described herein. In some embodiments, the nucleic acid is a DNA (e.g., cDNA) or RNA (e.g., mRNA).

In one aspect, the disclosure is related to a vector comprising one or more of the nucleic acids described herein.

In one aspect, the disclosure is related to a cell comprising the vector described herein. In some embodiments, the cell is a CHO cell. In one aspect, the disclosure is related to a cell comprising one or more of the nucleic acids described herein.

In one aspect, the disclosure is related to a method of producing a protein complex, the method comprising (a) culturing the cell described herein under conditions sufficient for the cell to produce the protein complex; and (b) collecting the protein complex produced by the cell.

In one aspect, the disclosure is related to a protein conjugate comprising the protein complex described herein, covalently bound to a therapeutic agent. In some embodiments, the therapeutic agent is a cytotoxic or cytostatic agent.

In one aspect, the disclosure is related to a method of treating a subject In some embodiments, the subject has a cancer cell expressing CD47 and/or PD-L1. In some embodiments, the cancer is breast cancer, prostate cancer, non-small cell lung cancer, pancreatic cancer, diffuse large B-cell lymphoma, mesothelioma, lung cancer, ovarian cancer, colon cancer, pleural tumor, glioblastoma, esophageal cancer, gastric cancer, synovial sarcoma, thymic carcinoma, endometrial carcinoma, stomach cancer, cholangiocarcinoma, head and neck cancer, blood cancer, or a combination thereof.

In one aspect, the disclosure is related to a method of decreasing the rate of tumor growth, the method comprising contacting a tumor cell with an effective amount of a composition comprising the protein complex or the protein conjugate described herein.

In one aspect, the disclosure is related to a method of killing a tumor cell, the method comprising contacting a tumor cell with an effective amount of a composition comprising the protein complex or the protein conjugate described herein.

In one aspect, the disclosure is related to a pharmaceutical composition comprising the protein complex, and a pharmaceutically acceptable carrier.

As used herein, the term "protein complex" or "protein construct" refers to a complex having one or more polypeptides. In some embodiments, the protein complex has two or more polypeptides, wherein the polypeptides can associate with each other, forming a dimer or a multimer.

As used herein, the term "CD47-binding domain" refers to a protein domain that can bind to CD47. In some embodiments, the CD47-binding domain can be an anti-CD47 antibody, an antigen-binding fragment thereof (e.g., a scFv or a VHH), or a CD47 binding protein or a portion thereof. In some embodiments, the CD47-binding domain can have one or more self-stabilizing domains. In some embodiments, the CD47-binding domain comprises or consists of a SIRPα extracellular domain. The SIRPα can be a wild type SIRPα, a human SIRPα, a polypeptide derived from a wildtype SIRPα (e.g., with mutations), or a portion thereof (e.g., the extracellular region of SIRPα, or IgV domain of SIRPα). In some embodiments, the polypeptide derived from a wildtype SIRPα can have one or more mutations. In some embodiments, the SIRPα extracellular domain comprises or consists of substantially the entire extracellular region of SIRPα or the variant thereof. In some embodiments, the SIRPα extracellular domain comprises or consists of the IgV domain of SIRPα or the variant thereof. In some embodiments, the IgV domain has one or more mutations. In some embodiments, the SIRPα extracellular domain has one or more mutations (e.g., mutations at positions corresponding to H24, I31, E54, G55, H56, and/or E70 of SEQ ID NO: 32).

As used herein, the term "PD-L1-binding domain" refers to a protein domain that can bind to PD-L1. In some embodiments, the PD-L1-binding domain can be an anti-PD-L1 antibody, an antigen-binding fragment thereof (e.g., a scFv or a VHH), or a PD-L1-binding protein or a portion thereof. In some embodiments, the PD-L1-binding domain is a VHH (e.g., anti-PD-L1 VHH (2H4)) that binds to PD-L1. In some embodiments, the PD-L1-binding domain is any of the VHHs described herein. In some embodiments, the PD-L1-binding domain comprises or consists of a PD-1 extracellular domain. The PD-1 can be a wild type PD-1, a human PD-1, a polypeptide derived from a wildtype PD-1 (e.g., with mutations), or a portion thereof (e.g., the extracellular region of PD-1). In some embodiments, the polypeptide derived from a wildtype PD-1 can have one or more mutations. In some embodiments, the PD-1 extracellular domain comprises or consists of substantially the entire extracellular region of PD-1 or the variant thereof. In some embodiments, the PD-1 extracellular domain comprises or consists of a portion of the extracellular region of PD-1 or the variant thereof. In some embodiments, the PD-1 extracellular domain has one or more mutations.

As used herein, the term "TGFβ-binding domain" refers to a protein domain that can bind to TGFβ. In some embodiments, the TGFβ-binding domain can be an anti-TGFβ antibody, an antigen-binding fragment thereof (e.g., a scFv or a VHH), or a TGFβ-binding protein or a portion thereof. In some embodiments, the TGFβ-binding domain comprises or consists of a TGFBRII extracellular domain. The TGFBRII can be a wild type TGFBRII, a human TGFBRII, a polypeptide derived from a wildtype TGFBRII (e.g., with mutations), or a portion thereof (e.g., the extracellular region of TGFBRII). In some embodiments, the polypeptide derived from a wildtype TGFBRII can have one or more mutations. In some embodiments, the TGFBRII extracellular domain comprises or consists of substantially the entire extracellular region of TGFBRII or the variant thereof. In some embodiments, the TGFBRII extracellular domain comprises or consists of a portion of the extracellular region of TGFBRII or the variant thereof. In some embodiments, the TGFBRII extracellular domain has one or more mutations (e.g., mutations at positions corresponding to S49 and/or D118 of SEQ ID NO: 33).

As used herein, the term "cancer" refers to cells having the capacity for autonomous growth. Examples of such cells include cells having an abnormal state or condition characterized by rapidly proliferating cell growth. The term is meant to include cancerous growths, e.g., tumors; oncogenic processes, metastatic tissues, and malignantly transformed cells, tissues, or organs, irrespective of histopathologic type or stage of invasiveness. Also included are malignancies of the various organ systems, such as respiratory, cardiovascular, renal, reproductive, hematological, neurological, hepatic, gastrointestinal, and endocrine systems; as well as adenocarcinomas which include malignancies such as most colon cancers, renal-cell carcinoma, prostate cancer and/or testicular tumors, non-small cell carcinoma of the lung, and cancer of the small intestine. Cancer that is "naturally arising" includes any cancer that is not experimentally induced by implantation of cancer cells into a subject, and includes, for example, spontaneously arising cancer, cancer caused by exposure of a patient to a carcinogen(s), cancer resulting from insertion of a transgenic oncogene or knock-out of a tumor suppressor gene, and cancer caused by infections, e.g., viral infections. The term "carcinoma" is art recognized and refers to malignancies of epithelial or endocrine tissues. The term also includes carcinosarcomas, which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation. The term "hematopoietic neoplastic disorders" includes diseases involving hyperplastic/neoplastic cells of hematopoietic origin. A hematopoietic neoplastic disorder can arise from myeloid, lymphoid or erythroid lineages, or precursor cells thereof. A hematologic cancer is a cancer that begins in blood-forming tissue, such as the bone marrow, or in the cells of the immune system. Examples of hematologic cancer include e.g., leukemia, lymphoma, and multiple myeloma etc.

As used herein, the terms "subject" and "patient" are used interchangeably throughout the specification and describe an animal, human or non-human, to whom treatment according to the methods of the present invention is provided. Veterinary and non-veterinary applications are contemplated in the present disclosure. Human patients can be adult humans or juvenile humans (e.g., humans below the age of 18 years old). In addition to humans, patients include but are not limited to mice, rats, hamsters, guinea-pigs, rabbits, ferrets, cats, dogs, and primates. Included are, for example, non-human primates (e.g., monkey, chimpanzee, gorilla, and the like), rodents (e.g., rats, mice, gerbils, hamsters, ferrets, rabbits), lagomorphs, swine (e.g., pig, miniature pig), equine, canine, feline, bovine, and other domestic, farm, and zoo animals.

As used herein, the terms "polypeptide," "peptide," and "protein" are used interchangeably to refer to polymers of amino acids of any length of at least two amino acids.

As used herein, the terms "polynucleotide," "nucleic acid molecule," and "nucleic acid sequence" are used interchangeably herein to refer to polymers of nucleotides of any length of at least two nucleotides, and include, without limitation, DNA, RNA, DNA/RNA hybrids, and modifications thereof.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 12 shows PD-1/PD-L1 blocking results of HCB301_v5 proteins on transfected CHO-S cells expressing PD-L1. "Biotin PD1 Fc" stands for biotinylated PD1_G4.

FIG. 16 shows Kabat and Chothia CDR sequences for anti-PD-L1 VHH (2H4).

FIG. 17 lists sequences discussed in the disclosure.

DETAILED DESCRIPTION

Figures 1A, 1B, 1C:
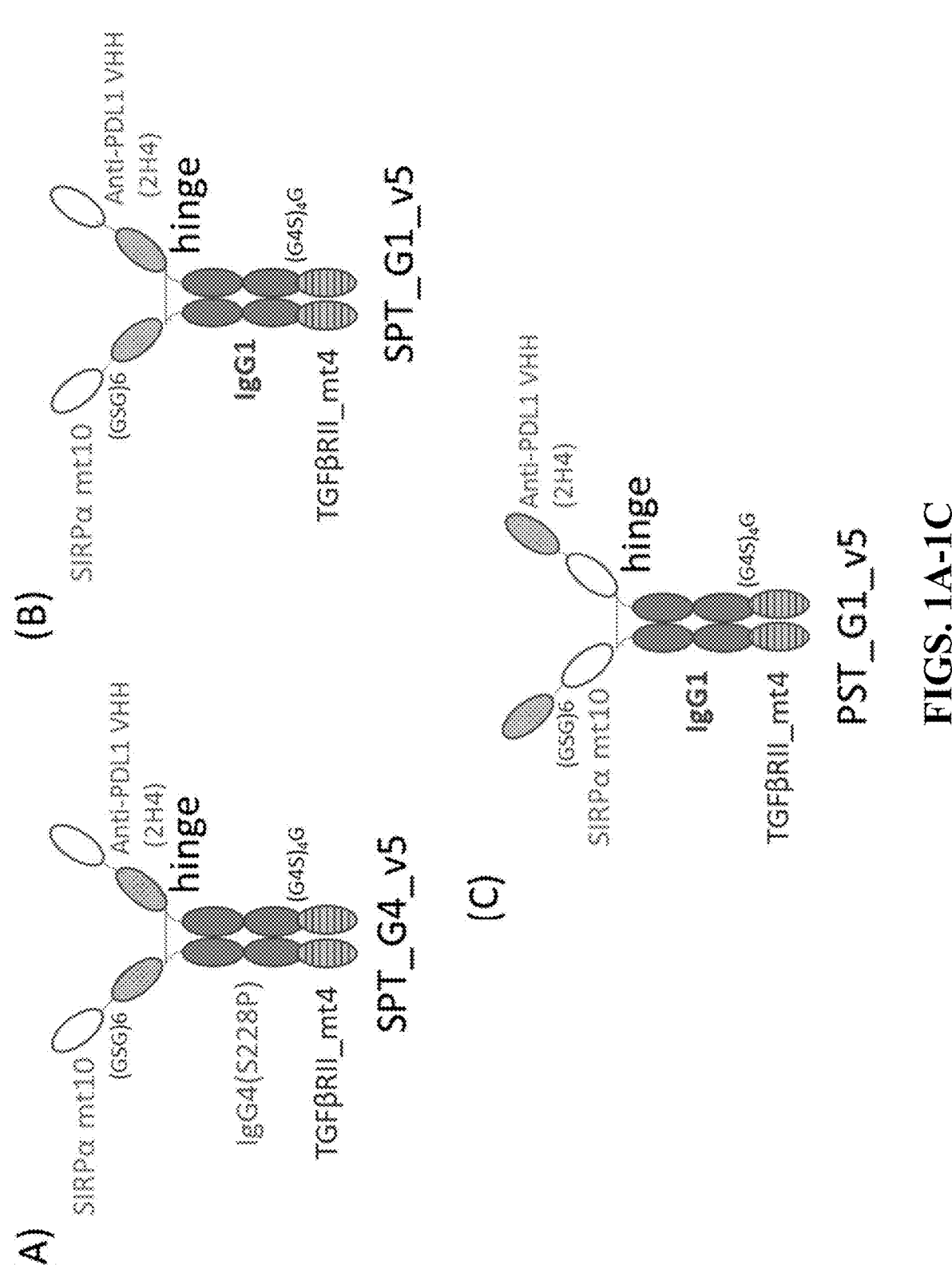
FIGS. 1A-1F show schematic structures of HCB301_v5 formats including SPT_G4_v5, SPT_G1_v5, PST_G1_v5, SP_G4_v5, SP_G1_v5, and PS_G1_v5, respectively.

The present disclosure provides protein complexes binding to CD47 and PD-L1. These protein complexes can be used to target the CD47/SIRPα pathway and PD-1/PD-L1 pathway simultaneously. The results indicate that the protein complexes can effectively bind to CD47-expressing cancer cells and block the interaction between endogenous SIRPα and CD47, thereby inducing innate immune response (e.g., phagocytosis of cancer cells by macrophages). On the other hand, the protein complexes showed minimal binding to RBC cells or platelets, thereby inhibiting the clearance of host cells as observed by the anti-CD47 antibody magrolimab. In addition, the results indicate that the protein complexes can selectively bind to PD-L1-expressing cancer cells and block the interaction between endogenous PD-1 and PD-L1. Further, the protein complexes can also include a TGFβ trap, thereby inhibiting TGFβ-induced immune-suppressive response, increasing T cell proliferation and cytokine secretion. The protein complexes (e.g., SPT_G4_v5) also exhibited a better anti-tumor activity than commercial anti-PD-L1 or anti-PD-1 antibodies (e.g., Atezolizumab and Pembrolizumab) in mouse xenograft models.

Therefore, the protein complexes described herein can be used for cancer treatment with enhanced tumor immunogenicity and antigen presentation through increased phagocytosis by macrophages (e.g., by inactivation of CD47-mediated inhibition of phagocytosis); and enhanced T cell activation through inhibition of PD-1/PD-L1 as well as TGFβ signaling pathways.

SIRPα Extracellular Domains

Signal regulatory protein a (SIRPα, SIRPα, Sirpa, or CD172A) is a transmembrane protein. It has an extracellular region comprising three Ig-like domains and a cytoplasmic region containing immunoreceptor tyrosine-based inhibition motifs that mediate binding of the protein tyrosine phosphatases SHP1 and SHP2. Tyrosine phosphorylation of SIRPα is regulated by various growth factors and cytokines as well as by integrin-mediated cell adhesion to extracellular matrix proteins. SIRPα is especially abundant in myeloid cells such as macrophages and dendritic cells, whereas it is expressed at only low levels in T, B, NK, and NKT cells.

The extracellular region of SIRPα can interact with its ligand CD47. The interaction of SIRPα on macrophages with CD47 on red blood cells prevents phagocytosis of Ig-opsonized red blood cells by macrophages in vitro and in vivo. The ligation of SIRPα on phagocytes by CD47 expressed on a neighboring cell results in phosphorylation of SIRPα cytoplasmic immunoreceptor tyrosine-based inhibition motifs, leading to the recruitment of SHP-1 and SHP-2 phosphatases. One resulting downstream effect is the prevention of myosin-IIA accumulation at the phagocytic synapse and consequently inhibition of phagocytosis. Thus, CD47-SIRPα interaction functions as a negative immune checkpoint to send a "don't eat me" signal to ensure that healthy autologous cells are not inappropriately phagocytosed. However, overexpression of CD47 has also been found in nearly all types of tumors, some of which include acute myeloid leukemia, non-Hodgkin's lymphoma, bladder cancer, and breast cancer. Such negative regulation of macrophages can be minimized by blocking the binding of CD47 to SIRPα. Thus, agents blocking CD47/SIRPα interaction can promote both antibody-dependent cellular phagocytosis (ADCP) and in some cases, trigger antibody-dependent cellular cytotoxicity (ADCC), thus can be used to treat various cancers.

Blocking CD47/SIRPα interaction can promote cellular phagocytosis, thus can be used to treat various cancers. It triggers the recognition and elimination of cancer cells by the innate immunity. Agents that target CD47 or SIRPα can be used to treat various tumors and cancers, e.g., solid tumors, hematologic malignancies (e.g., relapsed or refractory hematologic malignancies), acute myeloid leukemia, non-Hodgkin's lymphoma, breast cancer, bladder cancer, ovarian cancer, and small cell lung cancer tumors.

In addition, SIRPα acts to inhibit in vivo clearance of CD47-expressing host cells, including red blood cells and platelets, by macrophages. CD47-SIRPα interactions also appear essential for engraftment upon hematopoietic stem cells. Blocking CD47/SIRPα interaction may cause accidental killing of normal red blood cells, potentially resulting in anemia, and triggering inflammation. Thus, it is important to modulate the interaction of a SIRPα targeting agent with CD47, e.g., with limited or controlled effects on red blood cells.

A detailed description of SIRPα and its function can be found, e.g., in Yanagita et al. "Anti-SIRPα antibodies as a potential new tool for cancer immunotherapy." JCI insight 2.1 (2017); Seiffert et al. "Signal-regulatory protein a (SIRPα) but not SIRPβ is involved in T-cell activation, binds to CD47 with high affinity, and is expressed on immature CD34+ CD38− hematopoietic cells." Blood 97.9 (2001): 2741-2749; which are incorporated by reference herein in the entirety.

Human SIRPα is a member of signal regulatory proteins (SIRPs). Signal regulatory proteins are cell surface Ig superfamily proteins that mediate essential cell surface protein interactions and signal transduction. SIRPs all contain an N-terminal extracellular region, a single transmembrane domain and a C-terminal intracellular region.

The extracellular region of human SIRPα (UniProt identifier: P78324) has an IgV domain, an Ig-like Cl-type 1 domain, and an Ig-like Cl-type 2 domain. They correspond to amino acids 32-137, amino acids 148-247, and amino acids 254-348 of the human SIRPα protein (NP_542970.1). Amino acids 1-30 are signal peptides. Human SIRPα also has a long intracellular domain that comprises two putative immunoreceptor tyrosine-based inhibition motifs (ITIM). Activation of SIRPα ITIMs delivers inhibitory signals that negatively regulate cell responses.

In some embodiments, the protein complex comprises one or more CD47-binding domains. In some embodiments, the CD47-binding domain comprises or consists of a SIRPα extracellular domain. As used herein, the "SIRPα extracellular domain" refers to the entire or a portion of the extracellular region of SIRPα or the variant thereof, wherein the portion of the extracellular region can bind to CD47. The SIRPα extracellular domain can have one or more protein domains that can fold independently and form self-stabilizing structures. In some embodiments, the SIRPα extracellular domain comprises or consists of one or more domains selected from an IgV domain, an Ig-like Cl-type 1 domain, and an Ig-like Cl-type 2 domain. In some embodiments, the SIRPα extracellular domain comprises or consists of an IgV domain. In some embodiments, the SIRPα extracellular domain comprises or consists of an IgV domain and an Ig-like Cl-type 1 domain. In some embodiments, the SIRPα extracellular domain comprises or consists of an IgV domain, an Ig-like Cl-type 1 domain, and an Ig-like Cl-type 2 domain.

In some embodiments, the SIRPα extracellular domain described herein includes an amino acid sequence that is at least 80%, 85%, 90%, 95%, 96%, 97%, 98%, 99%, or 100% identical to amino acids 31-148 of human SIRPα protein (NCBI Accession No.: AAH26692.1; SEQ ID NO: 24). In some embodiments, the CD47-binding domain or SIRPα extracellular domain described herein includes an amino acid sequence that is at least 80%, 85%, 90%, 95%, 96%, 97%, 98%, 99%, or 100% identical to SEQ ID NO: 32, and also includes one or more (e.g., 1, 2, 3, 4, 5, or 6) amino acid mutations at positions corresponding to H24, 131, E54, G55, H56, and/or E70 of SEQ ID NO: 32. In some embodiments, the CD47-binding domain or SIRPα extracellular domain described herein includes one or more (e.g., 1, 2, 3, 4, 5, or 6) of the following: (a) the amino acid that corresponds to H24 of SEQ ID NO: 32 is T; (b) the amino acid that corresponds to 131 of SEQ ID NO: 32 is Y; (c) the amino acid that corresponds to E54 of SEQ ID NO: 32 is R; (d) the amino acid that corresponds to G55 of SEQ ID NO: 32 is Q; (e) the amino acid that corresponds to H56 of SEQ ID NO: 32 is T; and (f) the amino acid that corresponds to E70 of SEQ ID NO: 32 is F. In some embodiments, the CD47-binding domain or SIRPα extracellular domain described herein includes an amino acid sequence that is at least 80%, 85%, 90%, 95%, 96%, 97%, 98%, 99%, or 100% identical to SEQ ID NO: 7.

In some embodiments, the CD47-binding domain or SIRPα extracellular domain described herein includes the IgV domain of human SIRPα protein (wildtype or mutated). In some embodiments, the CD47-binding domain or SIRPα extracellular domain described herein includes the IgV domain of mouse SIRPα protein (wildtype or mutated).

Anti-PD-L1 VHH

Monoclonal and recombinant antibodies are important tools in medicine and biotechnology. Like all mammals, camelids (e.g., llamas) can produce conventional antibodies made of two heavy chains and two light chains bound together with disulfide bonds in a Y shape (e.g., IgG1). However, they also produce two unique subclasses of IgG: IgG2 and IgG3, also known as heavy chain IgG. These antibodies are made of only two heavy chains, which lack the CH1 region but still bear an antigen-binding domain at their N-terminus called VHH (or nanobody). Conventional Ig require the association of variable regions from both heavy and light chains to allow a high diversity of antigen-antibody interactions. Although isolated heavy and light chains still show this capacity, they exhibit very low affinity when compared to paired heavy and light chains. The unique feature of heavy chain IgG is the capacity of their monomeric antigen binding regions to bind antigens with specificity, affinity and especially diversity that are comparable to conventional antibodies without the need of pairing with another region. This feature is mainly due to a couple of major variations within the amino acid sequence of the variable region of the two heavy chains, which induce deep conformational changes when compared to conventional Ig. Major substitutions in the variable regions prevent the light chains from binding to the heavy chains, but also prevent unbound heavy chains from being recycled by the Immunoglobulin Binding Protein.

The single variable domain of these antibodies (designated VHH, sdAb, or nanobody) is the smallest antigen-binding domain generated by adaptive immune systems. The third Complementarity Determining Region (CDR3) of the variable region of these antibodies has been found to be twice as long as the conventional ones. This results in an increased interaction surface with the antigen as well as an increased diversity of antigen-antibody interactions, which compensates the absence of the light chains. With a long complementarity-determining region 3 (CDR3), VHHs can extend into crevices on proteins that are not accessible to conventional antibodies, including functionally interesting sites such as the active site of an enzyme or the receptor-binding canyon on a virus surface. Moreover, an additional cysteine residue allows the structure to be more stable, thus increasing the strength of the interaction.

VHHs offer numerous other advantages compared to conventional antibodies carrying variable domains (VH and VL) of conventional antibodies, including higher stability, solubility, expression yields, and refolding capacity, as well as better in vivo tissue penetration. Moreover, in contrast to the VH domains of conventional antibodies VHH do not display an intrinsic tendency to bind to light chains. This facilitates the induction of heavy chain antibodies in the presence of a functional light chain loci. Further, since VHH do not bind to VL domains, it is much easier to reformat VHHs into bispecific antibody constructs than constructs containing conventional VH-VL pairs or single domains based on VH domains.

The PD-1/PD-L1 pathway controls the induction and maintenance of immune tolerance within the tumor microenvironment. The activity of PD-1 and its ligands PD-L1 or PD-L2 are responsible for T cell activation, proliferation, and cytotoxic secretion in cancer to degenerating anti-tumor immune responses.

PD-1, also referred to as CD279, is a 55-kDa transmembrane protein containing 288 amino acids with an extracellular N-terminal domain (IgV-Like), a membrane-permeating domain and a cytoplasmic tail located at the N and C ends, respectively, with two tyrosine base.

PD-1 is an inhibitor of both adaptive and innate immune responses, and is expressed on activated T, natural killer (NK) and B lymphocytes, macrophages, dendritic cells (DCs) and monocytes.

PD-1 ligand (PD-L1 or PD-L1; also referred to as CD279 and B7-H1), belongs to the B7 series and is a 33-kDa type 1 transmembrane glycoprotein that contains 290 amino acids with Ig- and IgC domains in its extracellular region.

PD-L1 is usually expressed by macrophages, some activated T cells and B cells, DCs and some epithelial cells, particularly under inflammatory conditions. In addition, PD-L1 is expressed by tumor cells as an "adaptive immune mechanism" to escape anti-tumor responses. PD-L1 is associated with an immune environment rich in CD8 T cells, production of Th1 cytokines and chemical factors, as well as interferons and specific gene expression characteristics. It has been demonstrated that IFN-γ causes PD-L1 upregulation in ovarian cancer cells, which is responsible for disease progression, whereas IFN-γ receptor 1 inhibition can reduce PD-L1 expression in acute myeloid leukemia mouse models through the MEK/extracellular signal-regulated kinase (ERK) and MYD88/TRAF6 pathways. IFN-γ induces protein kinase D isoform 2 (PKD2), which is important for the regulation of PD-L1. Inhibition of PKD2 activity inhibits the expression of PD-L1 and promotes a strong antitumor immune response. NK cells secrete IFN-γ through the Janus kinase (JAK)1, JAK2 and signal transducer and activator of transcription (STAT)1 pathways, increasing the expression of PD-L1 on the surface of the tumor cells. Studies on melanoma cells have shown that IFN-γ secreted by T cells through the JAK1/JAK2-STAT1/STAT2/STAT3-IRF1 pathway may regulate the expression of PD-L1. T and NK cells appear to secrete IFN-γ, which induces PD-L1 expression on the surface of the target cells, including tumor cells.

PD-L1 acts as a pro-tumorigenic factor in cancer cells via binding to its receptors and activating proliferative and survival signaling pathways. This finding further indicated that PD-L1 is implicated in subsequent tumor progression. In addition, PD-L1 has been shown to exert non-immune proliferative effects on a variety of tumor cell types. For example, PD-L1 induced epithelial-to-mesenchymal transition (EMT) and stem cell-like phenotypes in renal cancer cells, indicating that the presence of the intrinsic pathway of PD-L1 promotes kidney cancer progression.

A detailed review of PD-L1 and its functions can be found in Han, Yanyan, Dandan Liu, and Lianhong Li. "PD-1/PD-L1 pathway: current researches in cancer." American journal of cancer research 10.3 (2020): 727; Liu, Jinhua, et al. "PD-1/PD-L1 checkpoint inhibitors in tumor immunotherapy." Frontiers in pharmacology 12 (2021); each of which is incorporated by reference in its entirety.

In some embodiments, the protein complex described herein comprises one or more PD-L1-binding domains. In some embodiments, the PD-L1-binding domain is a VHH that binds to PD-L1.

The disclosure provides a VHH that binds to PD-L1, e.g., anti-PD-L1 VHH (2H4) ("2H4"), the chimeric antibodies thereof, and the human or humanized antibodies thereof. The CDR sequences for 2H4, and 2H4 derived antibodies (e.g., humanized antibodies) include VHH CDRs 1, 2, and 3 as set forth in SEQ ID NOs: 26, 27, and 28, respectively, according to Kabat definition). The VHH CDRs can also be defined by Chothia system. Under the Chothia definition, the CDR sequences for 2H4, and 2H4 derived antibodies (e.g., humanized antibodies) include VHH CDRs 1, 2, and 3 as set forth in SEQ ID NOs: 29, 30, and 31, respectively. The amino acid sequence for anti-PD-L1 VHH (2H4) is set forth in SEQ ID NO: 7. Details of anti-PD-L1 VHH (2H4) can be found, e.g., in PCT Application No. PCT/CN2022/143510, which is incorporated herein by reference in its entirety.

In some embodiments, the amino acid sequences of the VHHs described herein are provided. In some embodiments, the VHH is at least 80%, 85%, 90%, 91%, 92%, 93%, 94%, 95%, 96%, 97%, 98%, or 99% identical to SEQ ID NO: 8. In some embodiments, the VHHs described herein can contain one, two, or three CDRs selected from the groups of SEQ ID NOs: 26-28, and SEQ ID NOs: 29-31.

In some embodiments, the VHHs described herein can have complementarity determining regions (CDRs) 1, 2, 3, wherein the CDR1 region comprises or consists of an amino acid sequence that is at least 80%, 85%, 90%, or 95% identical to a selected VHH CDR1 amino acid sequence, the CDR2 region comprises or consists of an amino acid sequence that is at least 80%, 85%, 90%, or 95% identical to a selected VHH CDR2 amino acid sequence, and the CDR3 region comprises or consists of an amino acid sequence that is at least 80%, 85%, 90%, or 95% identical to a selected VHH CDR3 amino acid sequence. The selected VHH CDRs 1, 2, 3 amino acid sequences are shown in FIG. 16 (CDRs under Kabat definition and Chothia definition).

In some embodiments, the VHHs described herein can contain one, two, or three of the CDRs of SEQ ID NO: 26 with zero, one or two amino acid insertions, deletions, or substitutions; SEQ ID NO: 27 with zero, one or two amino acid insertions, deletions, or substitutions; and SEQ ID NO: 28 with zero, one or two amino acid insertions, deletions, or substitutions. In some embodiments, the VHHs described herein can contain one, two, or three of the CDRs of SEQ ID NO: 29 with zero, one or two amino acid insertions, deletions, or substitutions; SEQ ID NO: 30 with zero, one or two amino acid insertions, deletions, or substitutions; and SEQ ID NO: 31 with zero, one or two amino acid insertions, deletions, or substitutions.

The insertions, deletions, and substitutions can be within the CDR sequence, or at one or both terminal ends of the CDR sequence. In some embodiments, the CDR is determined based on Kabat definition scheme. In some embodiments, the CDR is determined based on Chothia definition scheme. In some embodiments, the CDR is determined based on a combination of Kabat and Chothia definition scheme. In some embodiments, the CDR is determined based on IMGT definition. In some embodiments, the CDR is determined based on contact definition.

TGFBRII Extracellular Domains

TGF-beta receptor type-2 (TGFBRII) is the ligand-binding receptor for all members of the TGF-β family and expressed in virtually all cell types including fibroblasts. Ligand-induced cell response is mediated through either the canonical, Smad-dependent or non-canonical, Smad-independent signaling pathways such as c-Jun N-terminal kinase, Akt, Src, extracellular signal-regulated kinase and p38 mitogen-activated protein kinase pathway. Ligand binding to TGFBRII leads to dimerization and autophosphorylation of the receptor, which then binds to TGF-beta receptor type-1 (TGFBR1) or type-3 (TGFBR3). The newly formed heterotetrameric complex in turn recruits and phosphorylates regulatory SMADs (SMAD2 or SMAD3), which in their phosphorylation state bind to co-SMAD molecule SMAD4. The regulatory SMAD/co-SMAD complex translocates to the nucleus where it acts as a transcription factor regulating target gene expression.

A detailed description of TGFβ, TGFBRII, and the use of TGFβ trap to treat cancers are described, e.g., in Bierie, B., et al. "TGFβ: the molecular Jekyll and Hyde of cancer."

Nature Reviews Cancer 6.7 (2006): 506-520; Kim, B., et al. "Novel therapies emerging in oncology to target the TGF-β pathway." Journal of Hematology & Oncology 14.1 (2021): 1-20; and Lind, H., et al. "Dual targeting of TGF-β and PD-L1 via a bifunctional anti-PD-L1/TGF-βRII agent: status of preclinical and clinical advances." Journal for immunotherapy of cancer 8.1 (2020); each of which is incorporated by reference in its entirety.

According to UniProt identifier P37173, the extracellular region of human TGFBRII corresponds to amino acids 23-166 of NP_003233.4 (SEQ ID NO: 25), the transmembrane region of human TGFBRII corresponds to amino acids 167-187 of SEQ ID NO: 25, and the cytoplasmic region of human TGFBRII corresponds to amino acids 188-567 of SEQ ID NO: 25. The signal peptide corresponds to amino acids 1-22 of SEQ ID NO: 25.

In some embodiments, the protein complex comprises one or more TGFβ-binding domains. In some embodiments, the TGFβ-binding domain comprises or consists of a TGFBRII extracellular domain. As used herein, the "TGFBRII extracellular domain" refers to the entire or a portion of the extracellular region of TGFBRII or the variant thereof, wherein the portion of the extracellular region can bind to TGFβ. The TGFBRII extracellular domain can have one or more protein domains that can fold independently and form self-stabilizing structures. In some embodiments, the TGFBRII extracellular domain does not include the signal peptide.

In some embodiments, the TGFBRII extracellular domain described herein includes an amino acid sequence that is at least 80%, 85%, 90%, 95%, 96%, 97%, 98%, 99%, or 100% identical to amino acids 24-159 of human TGFBRII protein (NCBI Accession No.: NP_003233.4; SEQ ID NO: 25). In some embodiments, the TGFβ-binding domain or TGFBRII extracellular domain described herein includes an amino acid sequence that is at least 80%, 85%, 90%, 95%, 96%, 97%, 98%, 99%, or 100% identical to SEQ ID NO: 33. In some embodiments, the TGFBRII extracellular domain also includes one or more (e.g., 1 or 2) amino acid mutations at positions corresponding to S49 and/or D118 of SEQ ID NO: 33. In some embodiments, the TGFβ-binding domain or TGFBRII extracellular domain described herein includes one or more (e.g., 1 or 2) of the following: (a) the amino acid that corresponds to S49 of SEQ ID NO: 33 is E; and (b) the amino acid that corresponds to D118 of SEQ ID NO: 33 is E. In some embodiments, the TGFβ-binding domain or TGFBRII extracellular domain described herein includes an amino acid sequence that is at least 80%, 85%, 90%, 95%, 96%, 97%, 98%, 99%, or 100% identical to SEQ ID NO: 9.

In some embodiments, the TGFβ-binding domain or TGFBRII extracellular domain described herein includes all or a portion of human TGFBRII extracellular domain (wild-type or mutated). In some embodiments, the TGFβ-binding domain or TGFBRII extracellular domain described herein includes all or a portion of the extracellular domain of mouse TGFBRII protein (wildtype or mutated).

Protein Complexes Targeting CD47, PD-L1, and/or TGFβ

The disclosure provides protein complexes that can specifically bind to CD47. In some embodiments, these protein complexes can block CD47/SIRPα signaling pathway thus increase immune response. In some embodiments, these protein complexes can initiate phagocytosis.

The disclosure also provides protein complexes that can specifically bind to PD-L1. In some embodiments, these protein complexes can block PD-1/PD-L1 signaling pathway thus increase immune response. In some embodiments, these protein complexes can induce T cell activation, proliferation, and/or cytokine release.

In one aspect, the disclosure provides a protein complex or a protein construct, comprising or consisting of an Fc, one or more CD47-binding domains, one or more PD-L1-binding domains, and optionally one or more TGFβ-binding domains. As used herein, the term "Fc" refers to the fragment crystallizable region of an antibody (e.g., IgG, IgE, IgM, IgA, or IgD). The term "Fc region" or "Fc region sequence" refers to heavy chain constant domains (e.g., CH2 and CH3) in a heavy chain peptide that form the Fc region. In some embodiments, the protein complex or the protein construct comprises 1, 2, 3, 4, 5, or 6 CD47-binding domains. In some embodiments, the protein complex or the protein construct comprises 1, 2, 3, 4, 5, or 6 PD-L1-binding domains. In some embodiments, the protein complex or the protein construct comprises 1, 2, 3, 4, 5, or 6 TGFβ-binding domains.

In some embodiments, the protein complex or the protein construct comprises or consists of an Fc, a first domain that specifically binds to cluster of differentiation 47 (CD47), and a second domain that specifically binds to programmed death-ligand 1 (PD-L1).

In some embodiments, the first domain can bind to a cell (e.g., cancer cell) expressing CD47 and/or block the interaction between CD47 and signal regulatory protein a (SIRPα). In some embodiments, the first domain comprises all or a portion of the extracellular region of SIRPα. In some embodiments, the SIRPα is human SIRPα extracellular domain with one or more mutations (e.g., any of the SIRPα mutations described herein). In some embodiments, the first domain comprises an amino acid sequence that is at least 80%, 85%, 90%, 95%, 96%, 97%, 98%, 99% or 100% identical to SEQ ID NO: 7.

In some embodiments, the second domain can bind to a cell (e.g., cancer cell) expressing PD-L1 and/or stimulate T cell activation and proliferation. In some embodiments, the second domain comprises a VHH that binds to PD-L1. In some embodiments, the second domain comprises an amino acid sequence that is at least 80%, 85%, 90%, 95%, 96%, 97%, 98%, 99% or 100% identical to SEQ ID NO: 8.

In some embodiments, the Fc is human IgG1 Fc. In some embodiments, the Fc is human IgG4 Fc. In some embodiments, the first domain is linked to the N-terminus of a CH2 domain in the Fc, optionally via a hinge region. In some embodiments, the second domain is linked to the N-terminus of a CH2 domain in the Fc, optionally via a hinge region. In some embodiments, the hinge region is a human IgG4 hinge region optionally with S228P mutation according to EU numbering.

In some embodiments, the protein complex or the protein construct further comprises a third domain that specifically binds to transforming growth factor beta (TGFβ). In some embodiments, the third domain is linked to the C-terminus of a CH3 domain in the Fc, optionally via a linker peptide. In some embodiments, the third domain comprises all or a portion of the extracellular region of TGFBRII. In some embodiments, the TGFBRII is human TGFBRII extracellular domain with one or more mutations (e.g., any of the TGFBRII mutations described herein). In some embodiments, the first domain comprises an amino acid sequence that is at least 80%, 85%, 90%, 95%, 96%, 97%, 98%, 99% or 100% identical to SEQ ID NO: 9.

In some embodiments, the protein complex comprises two or more first domains. In some embodiments, the protein complex comprises two or more second domains. In some embodiments, the protein complex comprises two or more third domains.

In some embodiments, the CD47-binding domains, the PD-L1-binding domains, and the TGFβ-binding domains are linked to the Fc region through any of the linker peptide or the hinge region sequence as described herein.

Some embodiments of the protein complexes are shown in FIGS. 1A-1F. They are described in detail below.

SPT_G4_v5

In one aspect, the disclosure is related to a protein complex including a first polypeptide and a second polypeptide. The first polypeptide includes, preferably from N-terminus to C-terminus, a first CD47-binding domain, an optional first linker peptide, a first PD-L1-binding domain, an optional first hinge region, a first Fc region, an optionally a second linker peptide, and an optional first TGFβ-binding domain. The second polypeptide includes, preferably from N-terminus to C-terminus, a second CD47-binding domain, an optional third linker peptide, a second PD-L1-binding domain, an optional second hinge region, a second Fc region, an optionally a fourth linker peptide, and an optional second TGFβ-binding domain. A schematic structure of an exemplary protein complex having a SPT_G4_v5 format is shown in FIG. 1A.

In any of the protein complexes described herein, the first and/or the second CD47-binding domains can include a SIRPα extracellular domain (e.g., any of the SIRPα extracellular domain described herein). In some embodiments, the SIRPα extracellular domain includes one or more mutations (e.g., at positions corresponding to H24, I31, E54, G55, H56, and/or E70 of SEQ ID NO: 32). In some embodiments, the first and the second CD47-binding domains are identical. In some embodiments, the first and/or the second CD47-binding domain include an amino acid sequence that is at least 80%, 85%, 90%, 91%, 92%, 93%, 94%, 95%, 96%, 97%, 98%, 99%, or 100% identical to SEQ ID NO: 7. In some embodiments, the first and/or the second CD47-binding domains include the IgV domain of SIRPα (e.g., human SIRPα), with one or more mutations (at positions corresponding to H24, I31, E54, G55, H56, and/or E70 of SEQ ID NO: 32). In some embodiments, the first and the second CD47-binding domains are different.

In some embodiments, the first and/or the second PD-L1-binding domains include a VHH that binds to PD-L1, e.g., anti-PD-L1 VHH (2H4). In some embodiments, the first and/or the second PD-L1-binding domains are identical. In some embodiments, the first and/or the second PD-L1-binding domains are different. In some embodiments, the first and/or the second PD-L1-binding domains include an amino acid sequence that is at least 80%, 85%, 90%, 91%, 92%, 93%, 94%, 95%, 96%, 97%, 98%, 99%, or 100% identical to SEQ ID NO: 8.

In some embodiments, the first and/or the second hinge region can include all or a portion of the hinge region of an immunoglobulin, e.g., human IgG4 hinge region (SEQ ID NO: 14). In some embodiments, the first and/or the second hinge region include an amino acid sequence that is at least 80%, 85%, 90%, 91%, 92%, 93%, 94%, 95%, 96%, 97%, 98%, 99%, or 100% identical to SEQ ID NO: 14. In some embodiments, the first and the second hinge regions are identical. In some embodiments, the first and the second hinge regions are different. In some embodiments, the first and/or the second hinge region include a proline at position 228 according to EU numbering.

In some embodiments, the first and/or the second Fc region can be identical and can form a Fc homodimer. In some embodiments, the first and/or the second Fc region include all or a portion of the Fc region of an immunoglobulin, e.g., human IgG4 Fc region (SEQ ID NO: 15). In some embodiments, the first and/or the second Fc region include an amino acid sequence that is at least 80%, 85%, 90%, 91%, 92%, 93%, 94%, 95%, 96%, 97%, 98%, 99%, or 100% identical to SEQ ID NO: 15.

In some embodiments, the first and/or the second TGFβ-binding domains can include a TGFBRII extracellular domain (e.g., any of the TGFBRII extracellular domain described herein). In some embodiments, the TGFBRII extracellular domain includes one or more mutations (e.g., at positions corresponding to S49 and/or D118 of SEQ ID NO: 33). In some embodiments, the first and/or the second TGFβ-binding domains are identical. In some embodiments, the first and/or the second TGFβ-binding domains are different. In some embodiments, the first and/or the second TGFβ-binding domains include an amino acid sequence that is at least 80%, 85%, 90%, 91%, 92%, 93%, 94%, 95%, 96%, 97%, 98%, 99%, or 100% identical to SEQ ID NO: 9.

In some embodiments, the first and/or the third linker peptide described herein include an amino acid sequence that is at least 80%, 85%, 90%, 95%, or 100% identical to SEQ ID NO: 12. In some embodiments, the second and/or fourth linker peptide described herein include an amino acid sequence that is at least 80%, 85%, 90%, 95%, or 100% identical to SEQ ID NO: 13. In some embodiments, the first, the second, the third, and/or the fourth linker peptides described herein include an amino acid sequence that is at least 80%, 85%, 90%, 95%, or 100% identical to one or more (e.g., 1, 2, 3, 4, 5, 6, 7, or 8) repeats of GGGGS (SEQ ID NO: 18) or GSGGSG (SEQ ID NO: 19).

In some embodiments, the first and/or the second polypeptide include an amino acid sequence that is at least 80%, 85%, 90%, 91%, 92%, 93%, 94%, 95%, 96%, 97%, 98%, 99%, or 100% identical to SEQ ID NO: 1.

SPT_G1_v5

In one aspect, the disclosure is related to a protein complex including a first polypeptide and a second polypeptide. The first polypeptide includes, preferably from N-terminus to C-terminus, a first CD47-binding domain, an optional first linker peptide, a first PD-L1-binding domain, an optional first hinge region, a first Fc region, an optionally a second linker peptide, and an optional first TGFβ-binding domain. The second polypeptide includes, preferably from N-terminus to C-terminus, a second CD47-binding domain, an optional third linker peptide, a second PD-L1-binding domain, an optional second hinge region, a second Fc region, an optionally a fourth linker peptide, and an optional second TGFβ-binding domain. A schematic structure of an exemplary protein complex having a SPT_G1_v5 format is shown in FIG. 1B.

In any of the protein complexes described herein, the first and/or the second CD47-binding domains can include a SIRPα extracellular domain (e.g., any of the SIRPα extracellular domain described herein). In some embodiments, the SIRPα extracellular domain includes one or more mutations (e.g., at positions corresponding to H24, I31, E54, G55, H56, and/or E70 of SEQ ID NO: 32). In some embodiments, the first and the second CD47-binding domains are identical. In some embodiments, the first and/or the second CD47-binding domain include an amino acid sequence that is at least 80%, 85%, 90%, 91%, 92%, 93%, 94%, 95%, 96%, 97%, 98%, 99%, or 100% identical to SEQ ID NO: 7. In some embodiments, the first and/or the second CD47-binding domains include the IgV domain of SIRPα (e.g., human SIRPα), with one or more mutations (at positions corresponding to H24, I31, E54, G55, H56, and/or E70 of SEQ ID NO: 32). In some embodiments, the first and the second CD47-binding domains are different.

In some embodiments, the first and/or the second PD-L1-binding domains include a VHH that binds to PD-L1, e.g., anti-PD-L1 VHH (2H4). In some embodiments, the first and/or the second PD-L1-binding domains are identical. In some embodiments, the first and/or the second PD-L1-binding domains are different. In some embodiments, the first and/or the second PD-L1-binding domains include an amino acid sequence that is at least 80%, 85%, 90%, 91%, 92%, 93%, 94%, 95%, 96%, 97%, 98%, 99%, or 100% identical to SEQ ID NO: 8.

In some embodiments, the first and/or the second hinge region can include all or a portion of the hinge region of an immunoglobulin, e.g., human IgG1 hinge region (SEQ ID NO: 16). In some embodiments, the first and/or the second hinge region include an amino acid sequence that is at least 80%, 85%, 90%, 91%, 92%, 93%, 94%, 95%, 96%, 97%, 98%, 99%, or 100% identical to SEQ ID NO: 16. In some embodiments, the first and the second hinge regions are identical. In some embodiments, the first and the second hinge regions are different.

In some embodiments, the first and/or the second Fc region can be identical and can form a Fc homodimer. In some embodiments, the first and/or the second Fc region include all or a portion of the Fc region of an immunoglobulin, e.g., human IgG1 Fc region (SEQ ID NO: 17). In some embodiments, the first and/or the second Fc region include an amino acid sequence that is at least 80%, 85%, 90%, 91%, 92%, 93%, 94%, 95%, 96%, 97%, 98%, 99%, or 100% identical to SEQ ID NO: 17.

In some embodiments, the first and/or the second TGFβ-binding domains can include a TGFBRII extracellular domain (e.g., any of the TGFBRII extracellular domain described herein). In some embodiments, the TGFBRII extracellular domain includes one or more mutations (e.g., at positions corresponding to S49 and/or D118 of SEQ ID NO: 33). In some embodiments, the first and/or the second TGFβ-binding domains are identical. In some embodiments, the first and/or the second TGFβ-binding domains are different. In some embodiments, the first and/or the second TGFβ-binding domains include an amino acid sequence that is at least 80%, 85%, 90%, 91%, 92%, 93%, 94%, 95%, 96%, 97%, 98%, 99%, or 100% identical to SEQ ID NO: 9.

In some embodiments, the first and/or the third linker peptide described herein include an amino acid sequence that is at least 80%, 85%, 90%, 95%, or 100% identical to SEQ ID NO: 12. In some embodiments, the second and/or fourth linker peptide described herein include an amino acid sequence that is at least 80%, 85%, 90%, 95%, or 100% identical to SEQ ID NO: 13. In some embodiments, the first, the second, the third, and/or the fourth linker peptides described herein include an amino acid sequence that is at least 80%, 85%, 90%, 95%, or 100% identical to one or more (e.g., 1, 2, 3, 4, 5, 6, 7, or 8) repeats of GGGGS (SEQ ID NO: 18) or GSGGSG (SEQ ID NO: 19).

In some embodiments, the first and/or the second polypeptide include an amino acid sequence that is at least 80%, 85%, 90%, 91%, 92%, 93%, 94%, 95%, 96%, 97%, 98%, 99%, or 100% identical to SEQ ID NO: 2.

PST_G1_v5

In one aspect, the disclosure is related to a protein complex including a first polypeptide and a second polypeptide. The first polypeptide includes, preferably from N-terminus to C-terminus, a first PD-L1-binding domain, an optional first linker peptide, a first CD47-binding domain, an optional first hinge region, a first Fc region, an optionally a second linker peptide, and an optional first TGFβ-binding domain. The second polypeptide includes, preferably from N-terminus to C-terminus, a second PD-L1-binding domain, an optional third linker peptide, a second CD47-binding domain, an optional second hinge region, a second Fc region, an optionally a fourth linker peptide, and an optional second TGFβ-binding domain. A schematic structure of an exemplary protein complex having a PST_G1_v5 format is shown in FIG. 1C.

In some embodiments, the first and/or the second PD-L1-binding domains include a VHH that binds to PD-L1, e.g., anti-PD-L1 VHH (2H4). In some embodiments, the first and/or the second PD-L1-binding domains are identical. In some embodiments, the first and/or the second PD-L1-binding domains are different. In some embodiments, the first and/or the second PD-L1-binding domains include an amino acid sequence that is at least 80%, 85%, 90%, 91%, 92%, 93%, 94%, 95%, 96%, 97%, 98%, 99%, or 100% identical to SEQ ID NO: 8.

In any of the protein complexes described herein, the first and/or the second CD47-binding domains can include a SIRPα extracellular domain (e.g., any of the SIRPα extracellular domain described herein). In some embodiments, the SIRPα extracellular domain includes one or more mutations (e.g., at positions corresponding to H24, I31, E54, G55, H56, and/or E70 of SEQ ID NO: 32). In some embodiments, the first and the second CD47-binding domains are identical. In some embodiments, the first and/or the second CD47-binding domain include an amino acid sequence that is at least 80%, 85%, 90%, 91%, 92%, 93%, 94%, 95%, 96%, 97%, 98%, 99%, or 100% identical to SEQ ID NO: 7. In some embodiments, the first and/or the second CD47-binding domains include the IgV domain of SIRPα (e.g., human SIRPα), with one or more mutations (at positions corresponding to H24, I31, E54, G55, H56, and/or E70 of SEQ ID NO: 32). In some embodiments, the first and the second CD47-binding domains are different.

In some embodiments, the first and/or the second hinge region can include all or a portion of the hinge region of an immunoglobulin, e.g., human IgG1 hinge region (SEQ ID NO: 16). In some embodiments, the first and/or the second hinge region include an amino acid sequence that is at least 80%, 85%, 90%, 91%, 92%, 93%, 94%, 95%, 96%, 97%, 98%, 99%, or 100% identical to SEQ ID NO: 16. In some embodiments, the first and the second hinge regions are identical. In some embodiments, the first and the second hinge regions are different.

In some embodiments, the first and/or the second Fc region can be identical and can form a Fc homodimer. In some embodiments, the first and/or the second Fc region include all or a portion of the Fc region of an immunoglobulin, e.g., human IgG1 Fc region (SEQ ID NO: 17). In some embodiments, the first and/or the second Fc region include an amino acid sequence that is at least 80%, 85%, 90%, 91%, 92%, 93%, 94%, 95%, 96%, 97%, 98%, 99%, or 100% identical to SEQ ID NO: 17.

In some embodiments, the first and/or the second TGFβ-binding domains can include a TGFBRII extracellular domain (e.g., any of the TGFBRII extracellular domain described herein). In some embodiments, the TGFBRII extracellular domain includes one or more mutations (e.g., at positions corresponding to S49 and/or D118 of SEQ ID NO: 33). In some embodiments, the first and/or the second TGFβ-binding domains are identical. In some embodiments, the first and/or the second TGFβ-binding domains are different. In some embodiments, the first and/or the second TGFβ-binding domains include an amino acid sequence that is at least 80%, 85%, 90%, 91%, 92%, 93%, 94%, 95%, 96%, 97%, 98%, 99%, or 100% identical to SEQ ID NO: 9.

In some embodiments, the first and/or the third linker peptide described herein include an amino acid sequence that is at least 80%, 85%, 90%, 95%, or 100% identical to SEQ ID NO: 12. In some embodiments, the second and/or fourth linker peptide described herein include an amino acid sequence that is at least 80%, 85%, 90%, 95%, or 100% identical to SEQ ID NO: 13. In some embodiments, the first, the second, the third, and/or the fourth linker peptides described herein include an amino acid sequence that is at least 80%, 85%, 90%, 95%, or 100% identical to one or more (e.g., 1, 2, 3, 4, 5, 6, 7, or 8) repeats of GGGGS (SEQ ID NO: 18) or GSGGSG (SEQ ID NO: 19).

In some embodiments, the first and/or the second polypeptide include an amino acid sequence that is at least 80%, 85%, 90%, 91%, 92%, 93%, 94%, 95%, 96%, 97%, 98%, 99%, or 100% identical to SEQ ID NO: 3.

SP_G4_v5

Figures 1D, 1E, 1F:
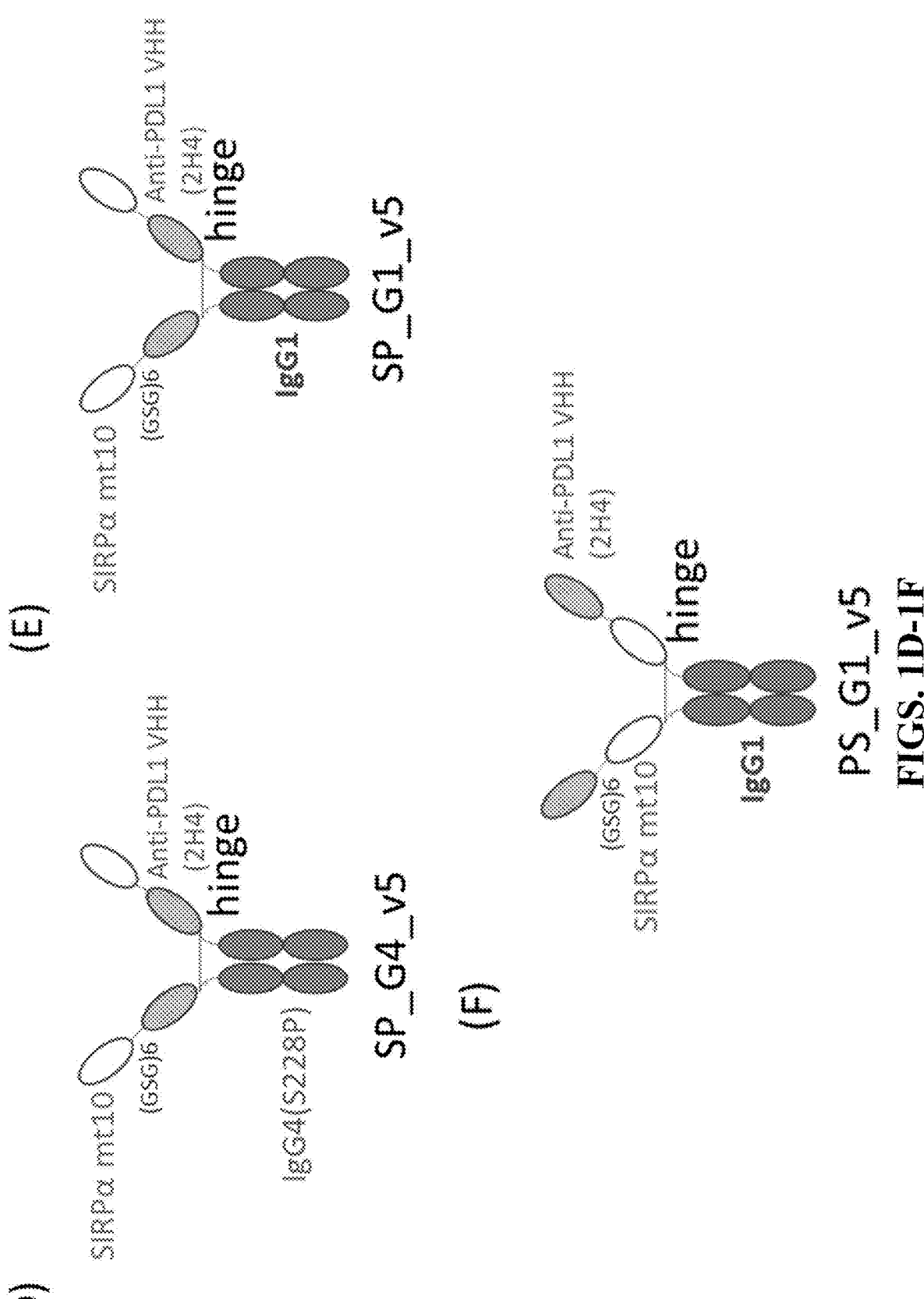

In one aspect, the disclosure is related to a protein complex including a first polypeptide and a second polypeptide. The first polypeptide includes, preferably from N-terminus to C-terminus, a first CD47-binding domain, an optional first linker peptide, a first PD-L1-binding domain, an optional first hinge region, and a first Fc region. The second polypeptide includes, preferably from N-terminus to C-terminus, a second CD47-binding domain, an optional second linker peptide, a second PD-L1-binding domain, an optional second hinge region, and a second Fc region. A schematic structure of an exemplary protein complex having a SP_G4_v5 format is shown in FIG. 1D.

In any of the protein complexes described herein, the first and/or the second CD47-binding domains can include a SIRPα extracellular domain (e.g., any of the SIRPα extracellular domain described herein). In some embodiments, the SIRPα extracellular domain includes one or more mutations (e.g., at positions corresponding to H24, I31, E54, G55, H56, and/or E70 of SEQ ID NO: 32). In some embodiments, the first and the second CD47-binding domains are identical. In some embodiments, the first and/or the second CD47-binding domain include an amino acid sequence that is at least 80%, 85%, 90%, 91%, 92%, 93%, 94%, 95%, 96%, 97%, 98%, 99%, or 100% identical to SEQ ID NO: 7. In some embodiments, the first and/or the second CD47-binding domains include the IgV domain of SIRPα (e.g., human SIRPα), with one or more mutations (at positions corresponding to H24, I31, E54, G55, H56, and/or E70 of SEQ ID NO: 32). In some embodiments, the first and the second CD47-binding domains are different.

In some embodiments, the first and/or the second PD-L1-binding domains include a VHH that binds to PD-L1, e.g., anti-PD-L1 VHH (2H4). In some embodiments, the first and/or the second PD-L1-binding domains are identical. In some embodiments, the first and/or the second PD-L1-binding domains are different. In some embodiments, the first and/or the second PD-L1-binding domains include an amino acid sequence that is at least 80%, 85%, 90%, 91%, 92%, 93%, 94%, 95%, 96%, 97%, 98%, 99%, or 100% identical to SEQ ID NO: 8.

In some embodiments, the first and/or the second hinge region can include all or a portion of the hinge region of an immunoglobulin, e.g., human IgG4 hinge region (SEQ ID NO: 14). In some embodiments, the first and/or the second hinge region include an amino acid sequence that is at least 80%, 85%, 90%, 91%, 92%, 93%, 94%, 95%, 96%, 97%, 98%, 99%, or 100% identical to SEQ ID NO: 14. In some embodiments, the first and the second hinge regions are identical. In some embodiments, the first and the second hinge regions are different. In some embodiments, the first and/or the second hinge region include a proline at position 228 according to EU numbering.

In some embodiments, the first and/or the second Fc region can be identical and can form a Fc homodimer. In some embodiments, the first and/or the second Fc region include all or a portion of the Fc region of an immunoglobulin, e.g., human IgG4 Fc region (SEQ ID NO: 15). In some embodiments, the first and/or the second Fc region include an amino acid sequence that is at least 80%, 85%, 90%, 91%, 92%, 93%, 94%, 95%, 96%, 97%, 98%, 99%, or 100% identical to SEQ ID NO: 15.

In some embodiments, the first and/or the second linker peptide described herein include an amino acid sequence that is at least 80%, 85%, 90%, 95%, or 100% identical to SEQ ID NO: 12. In some embodiments, the first and/or the second linker peptides described herein include an amino acid sequence that is at least 80%, 85%, 90%, 95%, or 100% identical to one or more (e.g., 1, 2, 3, 4, 5, 6, 7, or 8) repeats of GGGGS (SEQ ID NO: 18) or GSGGSG (SEQ ID NO: 19).

In some embodiments, the first and/or the second polypeptide include an amino acid sequence that is at least 80%, 85%, 90%, 91%, 92%, 93%, 94%, 95%, 96%, 97%, 98%, 99%, or 100% identical to SEQ ID NO: 4.

SP_G1_v5

In one aspect, the disclosure is related to a protein complex including a first polypeptide and a second polypeptide. The first polypeptide includes, preferably from N-terminus to C-terminus, a first CD47-binding domain, an optional first linker peptide, a first PD-L1-binding domain, an optional first hinge region, and a first Fc region. The second polypeptide includes, preferably from N-terminus to C-terminus, a second CD47-binding domain, an optional second linker peptide, a second PD-L1-binding domain, an optional second hinge region, and a second Fc region. A schematic structure of an exemplary protein complex having a SP_G1_v5 format is shown in FIG. 1E.

In any of the protein complexes described herein, the first and/or the second CD47-binding domains can include a SIRPα extracellular domain (e.g., any of the SIRPα extracellular domain described herein). In some embodiments, the SIRPα extracellular domain includes one or more mutations (e.g., at positions corresponding to H24, I31, E54, G55, H56, and/or E70 of SEQ ID NO: 32). In some embodiments, the first and the second CD47-binding domains are identical. In some embodiments, the first and/or the second CD47-binding domain include an amino acid sequence that is at least 80%, 85%, 90%, 91%, 92%, 93%, 94%, 95%, 96%, 97%, 98%, 99%, or 100% identical to SEQ ID NO: 7. In some embodiments, the first and/or the second CD47-binding domains include the IgV domain of SIRPα (e.g., human SIRPα), with one or more mutations (at positions corresponding to H24, I31, E54, G55, H56, and/or E70 of SEQ ID NO: 32). In some embodiments, the first and the second CD47-binding domains are different.

In some embodiments, the first and/or the second PD-L1-binding domains include a VHH that binds to PD-L1, e.g., anti-PD-L1 VHH (2H4). In some embodiments, the first and/or the second PD-L1-binding domains are identical. In some embodiments, the first and/or the second PD-L1-binding domains are different. In some embodiments, the first and/or the second PD-L1-binding domains include an amino acid sequence that is at least 80%, 85%, 90%, 91%, 92%, 93%, 94%, 95%, 96%, 97%, 98%, 99%, or 100% identical to SEQ ID NO: 8.

In some embodiments, the first and/or the second hinge region can include all or a portion of the hinge region of an immunoglobulin, e.g., human IgG1 hinge region (SEQ ID NO: 16). In some embodiments, the first and/or the second hinge region include an amino acid sequence that is at least 80%, 85%, 90%, 91%, 92%, 93%, 94%, 95%, 96%, 97%, 98%, 99%, or 100% identical to SEQ ID NO: 16. In some embodiments, the first and the second hinge regions are identical.

In some embodiments, the first and/or the second Fc region can be identical and can form a Fc homodimer. In some embodiments, the first and/or the second Fc region include all or a portion of the Fc region of an immunoglobulin, e.g., human IgG1 Fc region (SEQ ID NO: 17). In some embodiments, the first and/or the second Fc region include an amino acid sequence that is at least 80%, 85%, 90%, 91%, 92%, 93%, 94%, 95%, 96%, 97%, 98%, 99%, or 100% identical to SEQ ID NO: 17.

In some embodiments, the first and/or the second linker peptide described herein include an amino acid sequence that is at least 80%, 85%, 90%, 95%, or 100% identical to SEQ ID NO: 12. In some embodiments, the first and/or the second linker peptides described herein include an amino acid sequence that is at least 80%, 85%, 90%, 95%, or 100% identical to one or more (e.g., 1, 2, 3, 4, 5, 6, 7, or 8) repeats of GGGGS (SEQ ID NO: 18) or GSGGSG (SEQ ID NO: 19).

In some embodiments, the first and/or the second polypeptide include an amino acid sequence that is at least 80%, 85%, 90%, 91%, 92%, 93%, 94%, 95%, 96%, 97%, 98%, 99%, or 100% identical to SEQ ID NO: 5.

PS_G1_v5

In one aspect, the disclosure is related to a protein complex including a first polypeptide and a second polypeptide. The first polypeptide includes, preferably from N-terminus to C-terminus, a first PD-L1-binding domain, an optional first linker peptide, a first CD47-binding domain, an optional first hinge region, and a first Fc region. The second polypeptide includes, preferably from N-terminus to C-terminus, a second PD-L1-binding domain, an optional second linker peptide, a second CD47-binding domain, an optional second hinge region, and a second Fc region. A schematic structure of an exemplary protein complex having a PS_G1_v5 format is shown in FIG. 1F.

In some embodiments, the first and/or the second PD-L1-binding domains include a VHH that binds to PD-L1, e.g., anti-PD-L1 VHH (2H4). In some embodiments, the first and/or the second PD-L1-binding domains are identical. In some embodiments, the first and/or the second PD-L1-binding domains are different. In some embodiments, the first and/or the second PD-L1-binding domains include an amino acid sequence that is at least 80%, 85%, 90%, 91%, 92%, 93%, 94%, 95%, 96%, 97%, 98%, 99%, or 100% identical to SEQ ID NO: 8.

In any of the protein complexes described herein, the first and/or the second CD47-binding domains can include a SIRPα extracellular domain (e.g., any of the SIRPα extracellular domain described herein). In some embodiments, the SIRPα extracellular domain includes one or more mutations (e.g., at positions corresponding to H24, I31, E54, G55, H56, and/or E70 of SEQ ID NO: 32). In some embodiments, the first and the second CD47-binding domains are identical. In some embodiments, the first and/or the second CD47-binding domain include an amino acid sequence that is at least 80%, 85%, 90%, 91%, 92%, 93%, 94%, 95%, 96%, 97%, 98%, 99%, or 100% identical to SEQ ID NO: 7. In some embodiments, the first and/or the second CD47-binding domains include the IgV domain of SIRPα (e.g., human SIRPα), with one or more mutations (at positions corresponding to H24, I31, E54, G55, H56, and/or E70 of SEQ ID NO: 32). In some embodiments, the first and the second CD47-binding domains are different.

In some embodiments, the first and/or the second hinge region can include all or a portion of the hinge region of an immunoglobulin, e.g., human IgG1 hinge region (SEQ ID NO: 16). In some embodiments, the first and/or the second hinge region include an amino acid sequence that is at least 80%, 85%, 90%, 91%, 92%, 93%, 94%, 95%, 96%, 97%, 98%, 99%, or 100% identical to SEQ ID NO: 16. In some embodiments, the first and the second hinge regions are identical.

In some embodiments, the first and/or the second Fc region can be identical and can form a Fc homodimer. In some embodiments, the first and/or the second Fc region include all or a portion of the Fc region of an immunoglobulin, e.g., human IgG1 Fc region (SEQ ID NO: 17). In some embodiments, the first and/or the second Fc region include an amino acid sequence that is at least 80%, 85%, 90%, 91%, 92%, 93%, 94%, 95%, 96%, 97%, 98%, 99%, or 100% identical to SEQ ID NO: 17.

In some embodiments, the first and/or the second linker peptide described herein include an amino acid sequence that is at least 80%, 85%, 90%, 95%, or 100% identical to SEQ ID NO: 12. In some embodiments, the first and/or the second linker peptides described herein include an amino acid sequence that is at least 80%, 85%, 90%, 95%, or 100% identical to one or more (e.g., 1, 2, 3, 4, 5, 6, 7, or 8) repeats of GGGGS (SEQ ID NO: 18) or GSGGSG (SEQ ID NO: 19).

In some embodiments, the first and/or the second polypeptide include an amino acid sequence that is at least 80%, 85%, 90%, 91%, 92%, 93%, 94%, 95%, 96%, 97%, 98%, 99%, or 100% identical to SEQ ID NO: 6.

In any of the protein complexes described herein, the first and the second hinge regions can be different. In any of the protein complexes described herein, the first and/or the second Fc region can be different. In some embodiments, the first and/or the second Fc region can form a Fc heterodimer by introducing one or more mutations. For example, the first and/or the second Fc region can include one or more knob-into-hole (KIH) mutations. In some embodiments, the first and/or the second Fc region can form a Fc heterodimer using other technologies known in the art. Details heterodimeric Fc technologies can be found, e.g., in Ha, et al. "Immunoglobulin Fc heterodimer platform technology: from design to applications in therapeutic antibodies and proteins." Frontiers In Immunology 7 (2016): 394, which is incorporated herein by reference in its entirety.

In one aspect, the disclosure is related to a protein complex including a CD47-binding domain (e.g., any of the CD47-binding domain described herein) and a PD-L1-binding domain (e.g., any of the PD-L1-binding domain described herein). In some embodiments, the protein complex further includes a TGFβ-binding domain (e.g., any of the TGFβ-binding domain described herein). In some embodiments, the CD47-binding domain is or comprises a SIRPα extracellular domain (e.g., any of the SIRPα extracellular domain described herein). In some embodiments, the PD-L1-binding domain is or comprises a VHH that binds to PD-L1 (e.g., any of the VHHs described herein). In some embodiments, the TGFβ-binding domain is or comprises a TGFBRII extracellular domain (e.g., any of the TGFBRII extracellular domain described herein).

Characteristics of Protein Complexes

In some embodiments, the protein complex can comprise any CD47-binding domains, PD-L1-binding domains, and/or TGFβ-binding domains as described herein. The disclosure also provides nucleic acid comprising a polynucleotide encoding a polypeptide described herein.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90%, 95%, or 100%. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences. For example, the comparison of sequences and determination of percent identity between two sequences can be accomplished using a Blossum 62 scoring matrix with a gap penalty of 12, a gap extend penalty of 4, and a frameshift gap penalty of 5.

The protein complex described herein can include an Fc of an antibody. These antibodies can be of any type (e.g., IgG, IgE, IgM, IgD, IgA, and IgY), class or subclass (e.g., IgG1, IgG2, IgG3, IgG4, IgA1, IgA2, IgE1, IgE2). In some embodiments, the Fc region is derived from human IgG (e.g., IgG1, IgG2, IgG3, or IgG4). In some embodiments, the Fc region is an IgG4 Fc region (e.g., human IgG4 Fc region).

In some embodiments, the protein complex described herein is linked to the Fc region through an antibody hinge region (e.g., IgG, IgE hinge region). In addition, the Fc region can be modified to provide desired effector functions or serum half-life.

The protein complex described herein can block the binding between CD47 and endogenous SIRPα that are expressed on immune cells. In some embodiments, by binding to CD47, the protein complex described herein can inhibit the binding of CD47 (e.g., that is expressed on tumor cells) to endogenous SIRPα that is expressed on immune cells (e.g., myeloid cells, macrophages and dendritic cells), thereby blocking CD47/SIRPα pathway, upregulating immune response, and promoting phagocytosis.

The protein complex described herein can block the binding between PD-L1 and endogenous PD-1 that are expressed on immune cells. In some embodiments, by binding to PD-L1, the protein complex described herein can inhibit the binding of PD-L1 (e.g., that is expressed on tumor cells) to endogenous PD-1 that is expressed on immune cells (e.g., T cells), thereby blocking PD-1/PD-L1 pathway, upregulating immune response, activating T cell proliferation and cytokine release.

In some embodiments, the protein complex described herein can increase immune response, activity or number of immune cells (e.g., myeloid cells, macrophages, dendritic cells, antigen presenting cells) by at least 10%, 20%, 30%, 40%, 50%, 60%, 70%, 80%, 90%, 100%, 2 folds, 3 folds, 5 folds, 10 folds, or 20 folds.

In some implementations, the protein complex described herein can bind to CD47 (e.g., human CD47, monkey CD47, or mouse CD47), PD-L1 (e.g., human PD-L1, monkey PD-L1, or mouse PD-L1), or TGFβ (e.g., human TGFβ, monkey TGFβ, or mouse TGFβ) with a dissociation rate (koff) of less than 0.1 s$^{-1}$, less than 0.01 s$^{-1}$, less than 0.001 s$^{-1}$, less than 0.0001 s$^{-1}$, or less than 0.00001 s$^{-1}$. In some embodiments, the dissociation rate (koff) is greater than 0.01 s$^{-1}$, greater than 0.001 s$^{-1}$, greater than 0.0001 s$^{-1}$, greater than 0.00001 s$^{-1}$, or greater than 0.000001 s$^{-1}$. In some embodiments, kinetic association rates (kon) is greater than $1 \times 10^2$/Ms, greater than $1 \times 10^3$/Ms, greater than $1 \times 10^4$/Ms, greater than $1 \times 10^5$/Ms, or greater than $1 \times 10^6$/Ms. In some embodiments, kinetic association rates (kon) is less than $1 \times 10^5$/Ms, less than $1 \times 10^6$/Ms, or less than $1 \times 10^7$/Ms. Affinities can be deduced from the quotient of the kinetic rate constants (KD=koff/kon). In some embodiments, KD is less than $1 \times 10^{-6}$ M, less than $1 \times 10^{-7}$ M, less than $1 \times 10^{-8}$ M, less than $1 \times 10^{-9}$ M, or less than $1 \times 10^{-11}$ M. In some embodiments, the KD is less than 300 nM, 200 nM, 100 nM, 50 nM, 30 nM, 20 nM, 15 nM, 10 nM, 9 nM, 8 nM, 7 nM, 6 nM, 5 nM, 4 nM, 3 nM, 2 nM, 1 nM, 900 pM, 800 pM, 700 pM, 600 pM, 500 pM, 400 pM, 300 pM, 200 pM, 100 pM, 90 pM, 80 pM, 70 pM, 60 pM, 50 pM, 40 pM, 30 pM, 20 pM, or 10 pM. In some embodiments, KD is greater than $1 \times 10^{-7}$ M, greater than $1 \times 10^{-8}$ M, greater than $1 \times 10^{-9}$ M, greater than $1 \times 10^{-10\circ}$ M, greater than $1 \times 10^{-11}$ M, or greater than $1 \times 10^{-12}$ M.

General techniques for measuring the affinity include, e.g., ELISA, RIA, and surface plasmon resonance (SPR). In some embodiments, the protein complex described herein can bind to monkey CD47, and/or mouse CD47. In some embodiments, the protein complex described herein cannot bind to monkey CD47, and/or mouse CD47. In some embodiments, the protein complex described herein can bind to monkey PD-L1, and/or mouse PD-L1. In some embodiments, the protein complex described herein cannot bind to monkey PD-L1, and/or mouse PD-L1. In some embodiments, the protein complex described herein can bind to monkey TGFβ, and/or mouse TGFβ. In some embodiments, the protein complex described herein cannot bind to monkey TGFβ, and/or mouse TGFβ.

In some embodiments, thermal stabilities are determined. The protein complex described herein can have a Tm greater than 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95° C. In some embodiments, Tm is less than 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95° C.

In some embodiments, the protein complex described herein has a tumor growth inhibition percentage (TGI %) that is greater than 10%, 20%, 30%, 40%, 50%, 60%, 70%, 80%, 90%, 100%, 110%, 120%, 130%, 140%, 150%, 160%, 170%, 180%, 190%, or 200%. In some embodiments, the protein complex described herein has a tumor growth inhibition percentage that is less than 60%, 70%, 80%, 90%, 100%, 110%, 120%, 130%, 140%, 150%, 160%, 170%, 180%, 190%, or 200%. The TGI % can be determined, e.g., at 3, 4, 5, 6, 7, 8, 9, 10, 11, 12, 13, 14, 15, 16, 17, 18, 19, 20, 21, 22, 23, 24, 25, 26, 27, 28, 29, or 30 days after the treatment starts, or 1, 2, 3, 4, 5, 6, 7, 8, 9, 10, 11, or 12 months after the treatment starts. As used herein, the tumor growth inhibition percentage (TGI %) is calculated using the following formula:

$$TGI\ (\%) = \left[1 - (Ti - T0)/(Vi - V0)\right] \times 100$$

Ti is the average tumor volume in the treatment group on day i. T0 is the average tumor volume in the treatment group on day zero. Vi is the average tumor volume in the control group on day i. V0 is the average tumor volume in the control group on day zero.

In some embodiments, the tumor inhibitory effects of the protein complex described herein are comparable to an anti-CD47 reference antibody, e.g., Hu5F9-G4, or an anti-SIRPα antibody, e.g., CC-95251. Hu5F9-G4 is described e.g., in Sikic et al. "First-in-human, first-in-class phase I trial of the anti-CD47 antibody Hu5F9-G4 in patients with advanced cancers." Journal of Clinical Oncology 37.12 (2019): 946, which is incorporated herein by reference in its entirety. In some embodiments, the tumor inhibitory effects of the protein complex described herein are at least 10%, 20%, 30%, 40%, 50%, 60%, 70%, 80%, 90%, 1 fold, 2 folds, or 5 folds more than an anti-CD47 reference antibody, e.g., Hu5F9-G4, or an anti-SIRPα antibody, e.g., CC-95251. In some embodiments, the tumor inhibitory effects of the protein complex described herein are at least 10%, 20%, 30%, 40%, 50%, 60%, 70%, 80%, 90%, 1 fold, 2 folds, or 5 folds more than HCB101. Amino acid sequence of HCB101 is shown in SEQ ID NO: 20.

In some embodiments, the tumor inhibitory effects of the protein complex described herein are comparable to an anti-PD-L1 reference antibody, e.g., Atezolizumab (MPDL3280A), or an anti-PD-1 antibody, e.g., Pembrolizumab. MPDL3280A is described e.g., in Powles, T. et al. "MPDL3280A (anti-PD-L1) treatment leads to clinical activity in metastatic bladder cancer." Nature 515.7528 (2014): 558-562, which is incorporated herein by reference in its entirety. In some embodiments, the tumor inhibitory effects of the protein complex described herein are at least 10%, 20%, 30%, 40%, 50%, 60%, 70%, 80%, 90%, 1 fold, 2 folds, or 5 folds more than an anti-PD-L1 reference antibody, e.g., MPDL3280A, or an anti-PD-1 antibody, e.g., Pembrolizumab. In some embodiments, the tumor inhibitory effects of the protein complex described herein are at least 10%, 20%, 30%, 40%, 50%, 60%, 70%, 80%, 90%, 1 fold, 2 folds, or 5 folds more than anti-PD-L1 VHH (2H4). c is used as a control protein for the HCB301_v5 fusion proteins. Amino acid sequence of anti-PD-L1 VHH (2H4) is shown in SEQ ID NO: 8.

In some embodiments, the tumor inhibitory effects of the protein complex described herein are comparable to an TGFβ trap protein, e.g., G4_TGFβRII_mt4 or an anti-PD-L1 antibody×TGFβ trap M7824. M7824 is described e.g., in Gatti-Mays, M. E., et al. "M7824: a promising new strategy to combat cancer immune evasion." Oncoscience 5.11-12 (2018): 269, which is incorporated herein by reference in its entirety. In some embodiments, the tumor inhibitory effects of the protein complex described herein are at least 10%, 20%, 30%, 40%, 50%, 60%, 70%, 80%, 90%, 1 fold, 2 folds, or 5 folds more than G4_TGFβRII_mt4 or M7824. In some embodiments, the tumor inhibitory effects of the protein complex described herein are at least 10%, 20%, 30%, 40%, 50%, 60%, 70%, 80%, 90%, 1 fold, 2 folds, or 5 folds more than G4_TGFβRII_mt4. G4_TGFβRII_mt4 is used as a control protein for the HCB301_v5 fusion proteins. Amino acid sequence of G4_TGFβRII_mt4 is shown in SEQ ID NO: 21.

In some embodiments, the protein complex described herein has a functional Fc. In some embodiments, the Fc is from human IgG1, human IgG2, human IgG3, or human IgG4. In some embodiments, effector function of a functional Fc is antibody-dependent cell-mediated cytotoxicity (ADCC). In some embodiments, effector function of a functional Fc is phagocytosis. In some embodiments, effector function of a functional Fc is ADCC and phagocytosis. In some embodiments, the protein constructs as described herein have an Fc region without effector function. In some embodiments, the Fc is a human IgG4 Fc. In some embodiments, the Fc does not have a functional Fc region. For example, the Fc region has LALA mutations (L234A and L235A mutations in EU numbering), or LALA-PG mutations (L234A, L235A, P329G mutations in EU numbering).

Some other modifications to the Fc region can be made. For example, a cysteine residue(s) can be introduced into the Fc region, thereby allowing interchain disulfide bond formation in this region. The homodimeric fusion protein thus generated may have any increased half-life in vitro and/or in vivo.

In some embodiments, the IgG4 has S228P mutation (EU numbering). The S228P mutation prevents in vivo and in vitro IgG4 Fab-arm exchange.

In some embodiments, Fc regions are provided having a carbohydrate structure that lacks fucose attached (directly or indirectly) to an Fc region. For example, the amount of fucose in such Fc region composition may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues; or position 314 in Kabat numbering); however, Asn297 may also be located about ±3 amino acids upstream or downstream of position 297, i.e., between positions 294 and 300, due to minor sequence variations in Fc region sequences. Such fucosylation variants may have improved ADCC function. In some embodiments, to reduce glycan heterogeneity, the Fc region can be further engineered to replace the Asparagine at position 297 with Alanine (N297A).

In some embodiments, the main peak of HPLC-SEC accounts for at least 80%, 85%, 90%, 95%, 96%, 97%, 98%, 99%, or 99.5% of the protein complex described herein after purification by protein A-based affinity chromatography and/or size-exclusive chromatography.

In some embodiments, the protein complex described herein can bind to human CD47-expressing tumor cells (e.g., human CD47 tf CHO-S cells, FaDu cells, or NCI-H460 cells) with an affinity that is at least 10%, at least 20%, 30%, at least 40%, at least 50%, at least 60%, at least 70%, at least 80%, at least 90%, at least 100%, at least 110%, or at least 120% as compared to that an anti-CD47 reference antibody (e.g., Hu5F9-G4) or HCB101.

In some embodiments, the protein complex described herein can bind to human PD-L1-expressing tumor cells (e.g., transfected CHO-S cells expressing human PD-L1) with an affinity that is at least 10%, at least 20%, 30%, at least 40%, at least 50%, at least 60%, at least 70%, at least 80%, at least 90%, at least 100%, at least 110%, or at least 120% as compared to that of anti-PD-L1 VHH (2H4).

In some embodiments, the protein complex described herein can selectively bind to transfected cells expressing PD-L1 (e.g., transfected DLD1 cells expressing PD-L1; or PD-L1 tf DLD1 cells), e.g., in a mixture of cells of transfected DLD1 cells expressing PD-L1 and untransfected DLD1 cells. In some embodiments, the selectivity of the protein complex is comparable to Atezolizumab and/or anti-PD-L1 VHH (2H4).

In some embodiments, the protein complex described herein can bind to human TGFβ (e.g., TGFβ1, TGFβ2, or TGFβ3) with an affinity that is at least 30%, at least 40%, at least 50%, at least 60%, at least 70%, at least 80%, at least 90%, at least 100%, at least 110%, or at least 120% as compared to that of G4_TGFβRII_mt4. In some embodiments, the EC50 value of the protein complex binding to human TGFβ (e.g., TGFβ1, TGFβ2, or TGFβ3) is less than 10%, less than 20%, less than 30%, less than 40%, less than 50%, less than 60%, less than 70%, less than 80%, less than 90%, less than 1-fold, less than 2-fold, less than 3-fold, less than 4-fold, less than 5-fold, or less than 10-fold as compared to that of G4_TGFβRII_mt4.

In some embodiments, the protein complex described herein can bind to RBC cells or platelets (e.g., from human donors) with an affinity that is less than 90%, less than 80%, less than 70%, less than 60%, less than 50%, less than 40%, less than 30%, less than 20%, less than 10%, less than 5%, less than 3%, or less than 1% as compared to that of an anti-CD47 reference antibody (e.g., Hu5F9-G4).

In some embodiments, the protein complex described herein does not induce hemagglutination. In some embodiments, the protein complex described herein can induce hemagglutination at a minimal concentration that is greater than 500-fold, 2000-fold, 5000-fold, 20000-fold, or 50000-fold as compared to that of an anti-CD47 reference antibody (e.g., Hu5F9-G4).

In some embodiments, the protein complex described herein can block the interaction between CD47 (e.g., human CD47 or fragments thereof) and SIRPα (e.g., human SIRPα or fragments thereof). In some embodiments, the protein complex described herein can block the interaction between human CD47-expressing cells (e.g., CD47 tf CHO-S cells or FaDu cells) and human SIRPα. In some embodiments, the blocking ability of the protein complex described herein is at least 30%, at least 50%, at least 60%, at least 70%, at least 80%, at least 90%, at least 100%, at least 110%, at least 120%, at least 130%, at least 140%, or at least 150% as compared to that an anti-CD47 reference antibody (e.g., Hu5F9-G4) or HCB101.

In some embodiments, the protein complex described herein can block the interaction between PD-L1 (e.g., human PD-L1 or fragments thereof) and PD-1 (e.g., human PD-1 or fragments thereof). In some embodiments, the protein complex described herein can block the interaction between human PD-L1-expressing cells (e.g., PD-L1 tf CHO-S cells) and human PD-1. In some embodiments, the blocking ability of the protein complex described herein is at least 30%, at least 50%, at least 60%, at least 70%, at least 80%, at least 90%, at least 100%, at least 110%, at least 120%, at least 130%, at least 140%, or at least 150% as compared to that an anti-PD-L1 reference antibody (e.g., Atezolizumab) or anti-PD-L1 VHH (2H4).

In some embodiments, the protein complex described herein can induce phagocytosis of tumor cells by mouse macrophages (e.g., Raw264.7 cells). In some embodiments, the ability of the protein complex described herein to induce phagocytosis of tumor cells by mouse microphages is at least 10%, at least 20%, at least 30%, at least 40%, at least 50%, at least 60%, at least 70%, at least 80%, or at least 90% as compared to that of Hu5F9-G4 or HCB101. In some embodiments, the protein complex described herein has a weaker ability (e.g., less than 80%, 70%, 60%, 50%, 40%, 30%, 20% or 10%) to induce phagocytosis of RBC cells or platelets by mouse macrophages (e.g., Raw264.7 cells) than an anti-CD47 reference antibody (e.g., Hu5F9-G4) or HCB101.

In some embodiments, the protein complex described herein can induce phagocytosis of PD-L1-expressing tumor cells (e.g., PD-L1 tf DLD1 cells) by human macrophages (e.g., MDM cells). In some embodiments, the ability of the protein complex described herein to induce phagocytosis of PD-L1-expressing tumor cells by human macrophages is at least 10%, at least 20%, at least 30%, at least 40%, at least 50%, at least 60%, at least 70%, at least 80%, at least 90%, at least 100%, at least 110%, at least 120%, at least 130%, at least 140, at least 150%, at least 160%, at least 170%, at least 180%, at least 190%, or at least 200% as compared to that of an anti-CD47 reference antibody (e.g., Hu5F9-G4) or HCB101. In some embodiments, the protein complex described herein has a weaker ability (less than 80%, 70%, 60%, 50%, 40%, 30%, 20% or 10%) to induce phagocytosis of RBC cells or platelets by human macrophages (e.g., MDM cells) than an anti-CD47 reference antibody (e.g., Hu5F9-G4) or HCB101.

In some embodiments, the protein complex described herein can induce phagocytosis of CD47-expressing tumor cells by mouse macrophages (e.g., Raw264.7 cells). In some embodiments, the protein complex described herein can induce phagocytosis of CD47-expressing tumor cells by human macrophages (e.g., MDM cells).

Endogenous expression of CD47 on a variety of cell types, including red blood cells, creates a formidable "antigen sink" that may limit the efficacy of CD47-targeting therapies. Thus, the weaker ability of the protein complex described herein to induce phagocytosis of RBC cells and/or platelets may increase the in vivo efficacy of the protein complex. In addition, the protein complex may be administered with a lower dose level and/or less frequent dosage schedule with similar efficacy than an anti-CD47 reference antibody (e.g., Hu5F9-G4).

In some embodiments, the protein complex described herein can inhibit TGFβ-induced downstream pathways, e.g., smad2 reporter pathway. In some embodiments, the protein complex can inhibit TGFβ1 and/or TGFβ3-mediated smad2 reporter activity to less than 150%, less than 140%, less than 130%, less than 120%, less than 110%, less than 100%, less than 90%, less than 80%, less than 70%, less than 60%, or less than 50% as compared to that of G4_TGFβRII_mt4.

In some embodiments, the protein complex described herein can enhance T cell response (e.g., in an MLR assay). The principle of a mixed lymphocyte reaction (MLR) is that T cells from one donor will proliferate in the presence of APCs from a different donor. This is caused by the recognition of an HLA mismatch between two unrelated donors, which provokes an immune response from the T cells. MLR is often used as a means of inducing generalized stimulation/activation of T cells in culture. In some embodiments, the protein complex can increase the T cell proliferation by at least 10%, 20%, 30%, 40%, 50%, 60%, 70%, 80%, 90%, or 100% than control molecules used herein or combinations thereof. In some embodiments, the protein complex described herein can increase cytokine (e.g., IFN-γ and/or IL-2) production by at least 1-fold, 2-fold, 5-fold, 10-fold, 20-fold, 50-fold, 100-fold, 200-fold, 500-fold, 1000-fold, 2000-fold, or 10000-fold than control molecules used herein or combinations thereof.

In some embodiments, the protein complex described herein does not induce cytokine storm in human. In some embodiments, the protein complex described herein is not a superagonist. Details of cytokine storm and superagonist can be found, e.g., in Shimabukuro-Vornhagen, A. et al. "Cytokine release syndrome." Journal for ImmunoTherapy of Cancer 6.1 (2018): 1-14, which is incorporated herein by reference in its entirety.

In some embodiments, the protein complex described herein can inhibit tumor growth. In some embodiments, the protein complex described herein (e.g., SPT_G4_v5) can significantly inhibit tumor growth as compared the vehicle control. In some embodiments, the protein complex described herein (e.g., SPT_G4_v5) can inhibit tumor growth with a TGI value that is at least 100%, at least 110%, at least 120%, at least 130%, at least 140%, at least 150%, at least 160%, at least 170%, at least 180%, at least 190%, at least 200%, at least 2.5-fold, at least 3-fold, at least 3.5-fold, at least 4-fold, at least 4.5-fold, at least 5-fold, at least 6-fold, at least 7-fold, at least 8-fold, at least 9-fold, or at least 10-fold, as compared to that of HCB101, anti-PD-L1 VHH (2H4), G4_TGFβRII_mt4, Atezolizumab, and/or Pembrolizumab in a mouse xenograft model. In some embodiments, the tumor cells (e.g., pharynx carcinoma cells) are subcutaneously inoculated in NPG™ mice to generate the xenograft model. The immunodeficient NPG™ mice (NOD.Cg-PrkdcscidIl2rgtm1Vst/Vst mice) were obtained from Beijing Vitalstar Biotechnology Co., Ltd., which are the NOD/SCID mice with the knock-out interleukin-2 gamma chain receptor. In some embodiments, the tumor volume of the mice was analyzed 1, 2, 3, 4, 5, 6, 7, 8, 9, 10, 11, 12, 13, 14, 15, 16, 17, 18, 19, or 20 days post inoculation. In some embodiments, the TGI value of mice treated with the protein complex described herein (e.g., SPT_G4_v5) is at least 50%, at least 55%, at least 60%, at least 65%, at least 70%, at least 75%, at least 80%, at least 85%, or at least 90%.

Methods of Making Protein Complexes

Variants of the protein complexes described herein can be prepared by introducing appropriate nucleotide changes into the DNA encoding a polypeptide or a part thereof or by peptide synthesis. Such variants include, for example, deletions, insertions, or substitutions of residues within the amino acids sequences.

Screening can be performed to increase binding affinity of the CD47-binding domains, PD-L1-binding domains, and/or TGFβ-binding domains. Any combination of deletions, insertions, and/or combinations can be made to arrive at a variant that has increased binding affinity for the target. The amino acid changes introduced into the variant can also alter or introduce new post-translational modifications into the polypeptide, such as changing (e.g., increasing or decreasing) the number of glycosylation sites, changing the type of glycosylation site (e.g., changing the amino acid sequence such that a different sugar is attached by enzymes present in a cell), or introducing new glycosylation sites.

The CD47-binding domains, PD-L1-binding domains, and/or TGFβ-binding domains can be derived from any species of animal, including mammals. Non-limiting examples of binding domain variants include sequences derived from humans, primates, e.g., monkeys and apes, cows, pigs, horses, sheep, camelids (e.g., camels and llamas), chicken, goats, and rodents (e.g., rats, mice, hamsters and rabbits).

The present disclosure also provides recombinant vectors (e.g., an expression vectors) that include an isolated polynucleotide disclosed herein (e.g., a polynucleotide that encodes a polypeptide disclosed herein), host cells into which are introduced the recombinant vectors (i.e., such that the host cells contain the polynucleotide and/or a vector comprising the polynucleotide), and the production of recombinant polypeptides or fragments thereof by recombinant techniques.

As used herein, a "vector" is any construct capable of delivering one or more polynucleotide(s) of interest to a host cell when the vector is introduced to the host cell. An "expression vector" is capable of delivering and expressing the one or more polynucleotide(s) of interest as an encoded polypeptide in a host cell into which the expression vector has been introduced. Thus, in an expression vector, the polynucleotide of interest is positioned for expression in the vector by being operably linked with regulatory elements such as a promoter, enhancer, and/or a poly-A tail, either within the vector or in the genome of the host cell at or near or flanking the integration site of the polynucleotide of interest such that the polynucleotide of interest will be translated in the host cell introduced with the expression vector.

A vector can be introduced into the host cell by methods known in the art, e.g., electroporation, chemical transfection (e.g., DEAE-dextran), transformation, transfection, and infection and/or transduction (e.g., with recombinant virus). Thus, non-limiting examples of vectors include viral vectors (which can be used to generate recombinant virus), naked DNA or RNA, plasmids, cosmids, phage vectors, and DNA or RNA expression vectors associated with cationic condensing agents.

In some implementations, a polynucleotide disclosed herein (e.g., a polynucleotide that encodes a polypeptide disclosed herein) is introduced using a viral expression system (e.g., vaccinia or other pox virus, retrovirus, or adenovirus), which may involve the use of a non-pathogenic (defective), replication competent virus, or may use a replication defective virus. Techniques for incorporating DNA into such expression systems are well known to those of ordinary skill in the art. The DNA may also be "naked." The uptake of naked DNA may be increased by coating the DNA onto biodegradable beads that are efficiently transported into the cells.

For expression, the DNA insert comprising a polypeptide-encoding polynucleotide disclosed herein can be operatively linked to an appropriate promoter (e.g., a heterologous promoter), such as the phage lambda PL promoter, the *E. coli* lac, trp and tac promoters, the SV40 early and late promoters and promoters of retroviral LTRs, to name a few. Other suitable promoters are known to the skilled artisan. In some embodiments, the promoter is a cytomegalovirus (CMV) promoter. The expression constructs can further contain sites for transcription initiation, termination and, in the transcribed region, a ribosome binding site for translation. The coding portion of the mature transcripts expressed by the constructs may include a translation initiating at the beginning and a termination codon (UAA, UGA, or UAG) appropriately positioned at the end of the polypeptide to be translated.

As indicated, the expression vectors can include at least one selectable marker. Such markers include dihydrofolate reductase or neomycin resistance for eukaryotic cell culture and tetracycline or ampicillin resistance genes for culturing in *E. coli* and other bacteria. Representative examples of appropriate hosts include, but are not limited to, bacterial cells, such as *E. coli*, *Streptomyces*, and *Salmonella typhimurium* cells; fungal cells, such as yeast cells; insect cells such as *Drosophila* S2 and *Spodoptera* Sf9 cells; animal cells such as CHO, COS, Bowes melanoma, and HK 293 cells; and plant cells. Appropriate culture mediums and conditions for the host cells described herein are known in the art.

Non-limiting vectors for use in bacteria include pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Non-limiting eukaryotic vectors include pWL-NEO, pSV2CAT, pOG44, pXT1 and pSG available from Stratagene; and pSVK3, pBPV, pMSG and pSVL available from Pharmacia. Other suitable vectors will be readily apparent to the skilled artisan.

Non-limiting bacterial promoters suitable for use include the *E. coli* lacI and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous sarcoma virus (RSV), and metallothionein promoters, such as the mouse metallothionein-I promoter.

In the yeast *Saccharomyces cerevisiae*, a number of vectors containing constitutive or inducible promoters such as alpha factor, alcohol oxidase, and PGH can be used.

Introduction of the construct into the host cell can be affected by calcium phosphate transfection, DEAE-dextran mediated transfection, cationic lipid-mediated transfection, electroporation, transduction, infection or other methods. Such methods are described in many standard laboratory manuals, such as Davis et al., Basic Methods In Molecular Biology (1986), which is incorporated herein by reference in its entirety.

Transcription of DNA encoding a polypeptide of the present disclosure by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at base pairs 100 to 270, the cytomegalovirus early promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptides can be expressed in a modified form, such as a fusion protein (e.g., a GST-fusion) or with a histidine-tag, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties can be added to the polypeptide to facilitate purification. Such regions can be removed prior to final preparation of the polypeptide. The addition of peptide moieties to polypeptides to engender secretion or excretion, to improve stability and to facilitate purification, among others, are familiar and routine techniques in the art.

Methods of Treatment

The protein constructs or polypeptides of the present disclosure can be used for various therapeutic purposes.

In one aspect, the disclosure provides methods for treating a cancer in a subject, methods of reducing the rate of the increase of volume of a tumor in a subject over time, methods of reducing the risk of developing a metastasis, or methods of reducing the risk of developing an additional metastasis in a subject. In some embodiments, the treatment can halt, slow, retard, or inhibit progression of a cancer. In some embodiments, the treatment can result in the reduction of in the number, severity, and/or duration of one or more symptoms of the cancer in a subject.

In one aspect, the disclosure features methods that include administering a therapeutically effective amount of protein constructs or polypeptides disclosed herein to a subject in need thereof (e.g., a subject having, or identified or diagnosed as having, a cancer), e.g., breast cancer (e.g., triple-negative breast cancer), carcinoid cancer, cervical cancer, endometrial cancer, glioma, head and neck cancer, liver cancer, lung cancer, small cell lung cancer, lymphoma, melanoma, ovarian cancer, pancreatic cancer, prostate cancer, renal cancer, colorectal cancer, gastric cancer, testicular cancer, thyroid cancer, bladder cancer, urethral cancer, or hematologic malignancy. In some embodiments, the cancer is unresectable melanoma or metastatic melanoma, non-small cell lung carcinoma (NSCLC), small cell lung cancer (SCLC), bladder cancer, or metastatic hormone-refractory prostate cancer. In some embodiments, the subject has a solid tumor. In some embodiments, the cancer is squamous cell carcinoma of the head and neck (SCCHN), renal cell carcinoma (RCC), triple-negative breast cancer (TNBC), or colorectal carcinoma. In some embodiments, the cancer is melanoma, pancreatic carcinoma, mesothelioma, hematological malignancies, especially Non-Hodgkin's lymphoma, lymphoma, chronic lymphocytic leukemia, or advanced solid tumors.

In some embodiments, the compositions and methods disclosed herein can be used for treatment of patients at risk for a cancer. Patients with cancer can be identified with various methods known in the art.

As used herein, by an "effective amount" is meant an amount or dosage sufficient to effect beneficial or desired results including halting, slowing, retarding, or inhibiting progression of a disease, e.g., a cancer. An effective amount will vary depending upon, e.g., an age and a body weight of a subject to which the protein constructs or the polypeptides, vector comprising the polynucleotide encoding the protein constructs or the polypeptides, and/or compositions thereof is to be administered, a severity of symptoms and a route of administration, and thus administration can be determined on an individual basis.

An effective amount can be administered in one or more administrations. By way of example, an effective amount of the protein constructs or the polypeptides is an amount sufficient to ameliorate, stop, stabilize, reverse, inhibit, slow and/or delay progression of a cancer in a patient or is an amount sufficient to ameliorate, stop, stabilize, reverse, slow and/or delay proliferation of a cell (e.g., a biopsied cell, any of the cancer cells described herein, or cell line (e.g., a cancer cell line)) in vitro. As is understood in the art, an effective amount may vary, depending on, inter alia, patient history as well as other factors such as the type (and/or dosage) of the protein constructs or the polypeptides used.

Effective amounts and schedules for administering the protein constructs or the polypeptides, the polynucleotides encoding the protein constructs or the polypeptides, and/or compositions disclosed herein may be determined empirically, and making such determinations is within the skill in the art. Those skilled in the art will understand that the dosage that must be administered will vary depending on, for example, the mammal that will receive the protein constructs or the polypeptides, the polynucleotides, and/or compositions disclosed herein, the route of administration, the particular type of polynucleotides, and/or compositions disclosed herein used and other drugs being administered to the mammal.

A typical daily dosage of an effective amount of the protein constructs and/or the polypeptides is 0.1 mg/kg to 100 mg/kg (mg per kg of patient weight). In some embodiments, the dosage can be less than 100 mg/kg, 10 mg/kg, 9 mg/kg, 8 mg/kg, 7 mg/kg, 6 mg/kg, 5 mg/kg, 4 mg/kg, 3 mg/kg, 2 mg/kg, 1 mg/kg, 0.5 mg/kg, or 0.1 mg/kg. In some embodiments, the dosage can be greater than 10 mg/kg, 9 mg/kg, 8 mg/kg, 7 mg/kg, 6 mg/kg, 5 mg/kg, 4 mg/kg, 3 mg/kg, 2 mg/kg, 1 mg/kg, 0.5 mg/kg, or 0.1 mg/kg. In some embodiments, the dosage is about 10 mg/kg, 9 mg/kg, 8 mg/kg, 7 mg/kg, 6 mg/kg, 5 mg/kg, 4 mg/kg, 3 mg/kg, 2 mg/kg, or 1 mg/kg. In some embodiments, the dosage is about 1 to 10 mg/kg, about 1 to 5 mg/kg, or about 2 to 5 mg/kg.

In any of the methods described herein, the protein constructs or the polypeptides can be administered to the subject at least once a week (e.g., once a week, twice a week, three times a week, four times a week, once a day, twice a day, or three times a day).

In some embodiments, the one or more additional therapeutic agents can be administered to the subject prior to, or after administering the protein constructs or the polypeptides. In some embodiments, the one or more additional therapeutic agents are administered to the subject such that there is an overlap in the bioactive period of the one or more additional therapeutic agents and the protein constructs or the polypeptides in the subject.

In some embodiments, one or more additional therapeutic agents can be administered to the subject. The additional therapeutic agent can comprise one or more inhibitors selected from the group consisting of an inhibitor of B-Raf, an EGFR inhibitor, an inhibitor of a MEK, an inhibitor of ERK, an inhibitor of K-Ras, an inhibitor of c-Met, an inhibitor of anaplastic lymphoma kinase (ALK), an inhibitor of a phosphatidylinositol 3-kinase (PI3K), an inhibitor of an Akt, an inhibitor of mTOR, a dual PI3K/mTOR inhibitor, an inhibitor of Bruton's tyrosine kinase (BTK), and an inhibitor of Isocitrate dehydrogenase 1 (IDH1) and/or Isocitrate dehydrogenase 2 (IDH2). In some embodiments, the additional therapeutic agent is an inhibitor of indoleamine 2,3-dioxygenase-1 (IDO1) (e.g., epacadostat).

In some embodiments, the additional therapeutic agent can comprise one or more inhibitors selected from the group consisting of an inhibitor of HER3, an inhibitor of LSD1, an inhibitor of MDM2, an inhibitor of BCL2, an inhibitor of CHK1, an inhibitor of activated hedgehog signaling pathway, and an agent that selectively degrades the estrogen receptor.

In some embodiments, the additional therapeutic agent can comprise one or more therapeutic agents selected from the group consisting of Trabectedin, nab-paclitaxel, Trebananib, Pazopanib, Cediranib, Palbociclib, everolimus, fluoropyrimidine, IFL, regorafenib, Reolysin, Alimta, Zykadia, Sutent, temsirolimus, axitinib, everolimus, sorafenib, Votrient, Pazopanib, IMA-901, AGS-003, cabozantinib, Vinflunine, an Hsp90 inhibitor, Ad-GM-CSF, Temazolomide, IL-2, IFNa, vinblastine, Thalomid, dacarbazine, cyclophosphamide, lenalidomide, azacytidine, lenalidomide, bortezomid, amrubicine, carfilzomib, pralatrexate, and enzastaurin.

In some embodiments, the additional therapeutic agent can comprise one or more therapeutic agents selected from the group consisting of an adjuvant, a TLR agonist, tumor necrosis factor (TNF) alpha, IL-1, HMGB1, an IL-10 antagonist, an IL-4 antagonist, an IL-13 antagonist, an IL-17 antagonist, an HVEM antagonist, an ICOS agonist, a treatment targeting CX3CL1, a treatment targeting CXCL9, a treatment targeting CXCL10, a treatment targeting CCL5, an LFA-1 agonist, an ICAM1 agonist, and a Selectin agonist.

In some embodiments, carboplatin, nab-paclitaxel, paclitaxel, cisplatin, pemetrexed, gemcitabine, FOLFOX, or FOLFIRI are administered to the subject.

In some embodiments, the additional therapeutic agent is an anti-OX40 antibody, an anti-PD-1 antibody, an anti-PD-L1 antibody, an anti-PD-L2 antibody, an anti-SIRPα antibody, an anti-CD47 antibody, an anti-LAG-3 antibody, an anti-TIGIT antibody, an anti-BTLA antibody, an anti-CTLA-4 antibody, or an anti-GITR antibody. In some embodiments, the additional therapeutic agent is an anti-CD20 antibody (e.g., rituximab) or an anti-EGF receptor antibody (e.g., cetuximab).

Pharmaceutical Compositions and Routes of Administration

Also provided herein are pharmaceutical compositions that contain the protein constructs or the polypeptides described herein. The pharmaceutical compositions can be formulated in any manner known in the art.

Pharmaceutical compositions are formulated to be compatible with their intended route of administration (e.g., intravenous, intraarterial, intramuscular, intradermal, subcutaneous, or intraperitoneal). The compositions can include a sterile diluent (e.g., sterile water or saline), a fixed oil, polyethylene glycol, glycerine, propylene glycol or other synthetic solvents, antibacterial or antifungal agents, such as benzyl alcohol or methyl parabens, chlorobutanol, phenol, ascorbic acid, thimerosal, and the like, antioxidants, such as ascorbic acid or sodium bisulfite, chelating agents, such as ethylenediaminetetraacetic acid, buffers, such as acetates, citrates, or phosphates, and isotonic agents, such as sugars (e.g., dextrose), polyalcohols (e.g., mannitol or sorbitol), or salts (e.g., sodium chloride), or any combination thereof. Liposomal suspensions can also be used as pharmaceutically acceptable carriers. Preparations of the compositions can be formulated and enclosed in ampules, disposable syringes, or multiple dose vials. Where required (as in, for example, injectable formulations), proper fluidity can be maintained by, for example, the use of a coating, such as lecithin, or a surfactant. Absorption of the agents can be prolonged by including an agent that delays absorption (e.g., aluminum monostearate and gelatin). Alternatively, controlled release can be achieved by implants and microencapsulated delivery systems, which can include biodegradable, biocompatible polymers (e.g., ethylene vinyl acetate, polyanhydrides, polyglycolic acid, collagen, polyorthoesters, and polylactic acid).

Compositions containing the protein constructs or the polypeptides described herein can be formulated for parenteral (e.g., intravenous, intraarterial, intramuscular, intradermal, subcutaneous, or intraperitoneal) administration in dosage unit form (i.e., physically discrete units containing a predetermined quantity of active compound for ease of administration and uniformity of dosage).

Pharmaceutical compositions for parenteral administration are preferably sterile and substantially isotonic and manufactured under Good Manufacturing Practice (GMP) conditions. Pharmaceutical compositions can be provided in unit dosage form (i.e., the dosage for a single administration). Pharmaceutical compositions can be formulated using one or more physiologically acceptable carriers, diluents, excipients or auxiliaries. The formulation depends on the route of administration chosen. For injection, the agents can be formulated in aqueous solutions, preferably in physiologically-compatible buffers to reduce discomfort at the site of injection. The solution can contain formulatory agents such as suspending, stabilizing and/or dispersing agents. Alternatively, the protein constructs or the polypeptides can be in lyophilized form for constitution with a suitable vehicle, e.g., sterile pyrogen-free water, before use.

Toxicity and therapeutic efficacy of compositions can be determined by standard pharmaceutical procedures in cell cultures or experimental animals (e.g., monkeys). One can, for example, determine the LD50 (the dose lethal to 50% of the population) and the ED50 (the dose therapeutically effective in 50% of the population): the therapeutic index being the ratio of LD50:ED50. Agents that exhibit high therapeutic indices are preferred. Where an agent exhibits an undesirable side effect, care should be taken to minimize potential damage (i.e., reduce unwanted side effects). Toxicity and therapeutic efficacy can be determined by other standard pharmaceutical procedures.

Exemplary doses include milligram or microgram amounts of any of the protein constructs or the polypeptides described herein per kilogram of the subject's weight (e.g., about 1 µg/kg to about 500 mg/kg; about 100 µg/kg to about 500 mg/kg; about 100 µg/kg to about 50 mg/kg; about 10 µg/kg to about 5 mg/kg; about 10 µg/kg to about 0.5 mg/kg; about 1 µg/kg to about 50 µg/kg; about 1 mg/kg to about 10 mg/kg; or about 1 mg/kg to about 5 mg/kg). While these doses cover a broad range, one of ordinary skill in the art will understand that therapeutic agents can vary in their potency, and effective amounts can be determined by methods known in the art. Typically, relatively low doses are administered at first, and the attending health care professional or veterinary professional (in the case of therapeutic application) or a researcher (when still working at the development stage) can subsequently and gradually increase the dose until an appropriate response is obtained. In addition, it is understood that the specific dose level for any particular subject will depend upon a variety of factors including the activity of the specific compound employed, the age, body weight, general health, gender, and diet of the subject, the time of administration, the route of administration, the rate of excretion, and the half-life in vivo.

The pharmaceutical compositions can be included in a container, pack, or dispenser together with instructions for administration. The disclosure also provides methods of manufacturing the protein constructs or the polypeptides for various uses as described herein.

EXAMPLES

The invention is further described in the following examples, which do not limit the scope of the invention described in the claims.

Example 1. Design of Fc-Based Designer Biologics
(FBDB™) with Anti-PD-L1×SIRPα×TGFβ Trap
Formats Various triple-targeting formats of FBDB™ were developed and optimized to achieve specific functional outcomes as follows: (1) to direct therapeutics to PD-L1⁺ tumor cells; (2) to enhance the synergistic power between innate immunity (e.g., targeting the SIRPα/CD47 pathway) and adaptive immunity (e.g., targeting the PD-1/PD-L1 pathway); (3) to reverse TGFβ-induced immunosuppression.

Each format contains at least three distinct types of immune modules that are directly or indirectly connected to the Fc region of an IgG (e.g., human IgG4 or human IgG1). The three immune modules are: (1) one or more SIRPα extracellular domains that can stimulate the antigen-presentation by inducing phagocytosis; (2) one or more anti-PD-L1 extracellular domains that can block the PD-1/PD-L1 pathway to enhance the T cell function and guide the SIRPαx PD-1×TGFβ-trap molecules to the PD-L1-expressing tumors; and (3) one or more TGFβ-trap molecules (e.g., the extracellular domain of TGF-beta receptor type-2 (TGFBRII)) that can capture the immune-suppressive TGFβ and improve the tumor microenvironment to augment the immune response. For example, the SIRPα extracellular domains disrupts the interaction between CD47 expressed on tumor cells and SIRPα present on macrophages, thereby releasing the inhibitory signal and enabling macrophages to overcome the "don't eat me" mechanism; the anti-PD-L1 extracellular domains disrupt the interaction between PD-1 expressed on T cells and PD-L1 present on tumor cells, thereby releasing the inhibitory brake on effector T cells and promoting T cell functions; and the TGFβ-trap molecule can counteract TGFβ induced immune-suppression, thereby improving the tumor microenvironment (TME) to augment the immune response.

Three triple-targeting formats of FBDB™ were designed as shown in FIGS. 1A-1C. SPT_G4_v5 (schematic structure shown in FIG. 1A) includes two identical polypeptide chains, and each polypeptide chain has an amino acid sequence as set forth in SEQ ID NO: 1. Specifically, each polypeptide chain includes, from N-terminus to C-terminus, a SIRPα extracellular domain SIRPα_mt10 (SEQ ID NO: 7), an anti-PD-L1 VHH (2H4) (SEQ ID NO: 8), a human IgG4 Fc region (S228P) containing hinge region (SEQ ID NO: 10), and a mutated TGFBRII extracellular domain TGFβRII_mt4 (SEQ ID NO: 9). The SIRPα_mt10 is connected to the N-terminus of the anti-PD-L1 VHH (2H4) via a (GSG)$_6$ linker peptide (SEQ ID NO: 12). The TGFβRII_mt4 is connected to the C-terminus of the human IgG4 Fc via a (G4S)$_4$G linker peptide (SEQ ID NO: 13).

SPT_G1_v5 (schematic structure shown in FIG. 1B) includes two identical polypeptide chains, and each polypeptide chain has an amino acid sequence as set forth in SEQ ID NO: 2. Specifically, each polypeptide chain includes, from N-terminus to C-terminus, a SIRPα extracellular domain SIRPα mt10 (SEQ ID NO: 7), an anti-PD-L1 VHH (2H4) (SEQ ID NO: 8), a human IgG1 Fc region containing hinge region (SEQ ID NO: 11), and a TGFBRII extracellular domain TGFβRII_mt4 (SEQ ID NO: 9). The SIRPα_mt10 and the anti-PD-L1 VHH (2H4) are connected via a (GSG)$_6$ linker peptide (SEQ ID NO: 12). The TGFβRII_mt4 is connected to the C-terminus of the human IgG1 Fc via a (G4S)$_4$G linker peptide (SEQ ID NO: 13).

PST_G1_v5 (schematic structure shown in FIG. 1C) includes two identical polypeptide chains, and each polypeptide chain has an amino acid sequence as set forth in SEQ ID NO: 3. Specifically, each polypeptide chain includes, from N-terminus to C-terminus, an anti-PD-L1 VHHs (2H4) (SEQ ID NO: 8), a SIRPα extracellular domain SIRPα_mt10 (SEQ ID NO: 7), a human IgG1 Fc region containing hinge region (SEQ ID NO: 11), and a TGFBRII extracellular domain TGFβRII_mt4 (SEQ ID NO: 9). The anti-PD-L1 VHH (2H4) is connected to the N-terminus of the SIRPα_mt10 via a (GSG)$_6$ linker peptide (SEQ ID NO: 12). The TGFβRII_mt4 is connected to the C-terminus of the human IgG1 Fc via a (G4S)$_4$G linker peptide (SEQ ID NO: 13).

Three double-targeting formats of FBDB™ were designed as shown in FIGS. 1D-1F. SP_G4_v5 (schematic structure shown in FIG. 1D) includes two identical polypeptide chains, and each polypeptide chain has an amino acid sequence as set forth in SEQ ID NO: 4. Specifically, each polypeptide chain includes, from N-terminus to C-terminus, a SIRPα extracellular domain SIRPα_mt10 (SEQ ID NO: 7), an anti-PD-L1 VHH (2H4) (SEQ ID NO: 8), and a human IgG4 Fc region (S228P) containing hinge region (SEQ ID NO: 10). The SIRPα_mt10 is connected to the N-terminus of the anti-PD-L1 VHH (2H4) via a (GSG)$_6$ linker peptide (SEQ ID NO: 12).

SP_G1_v5 (schematic structure shown in FIG. 1E) includes two identical polypeptide chains, and each polypeptide chain has an amino acid sequence as set forth in SEQ ID NO: 5. Specifically, each polypeptide chain includes, from N-terminus to C-terminus, a SIRPα extracellular domain SIRPα_mt10 (SEQ ID NO: 7), an anti-PD-L1 VHH (2H4) (SEQ ID NO: 8), and a human IgG1 Fc region containing hinge region (SEQ ID NO: 11). The SIRPα_mt10 and the anti-PD-L1 VHH (2H4) are connected via a (GSG)$_6$ linker peptide (SEQ ID NO: 12).

PS_G1_v5 (schematic structure shown in FIG. 1F) includes two identical polypeptide chains, and each polypeptide chain has an amino acid sequence as set forth in SEQ ID NO: 6. Specifically, each polypeptide chain includes, from N-terminus to C-terminus, an anti-PD-L1 VHH (2H4) (SEQ ID NO: 8), a SIRPα extracellular domain SIRPα_mt10 (SEQ ID NO: 7), and a human IgG1 Fc region containing hinge region (SEQ ID NO: 11). The anti-PD-L1 VHH (2H4) is connected to the N-terminus of the SIRPα_mt10 via a (GSG)$_6$ linker peptide (SEQ ID NO: 12).

The expressed proteins were purified by a protein A column, followed by HPLC-SEC (high-performance liquid chromatography coupled with size-exclusion chromatography; Agilent). Specifically, the six HCB301_v5 proteins were expressed in CHO-S cells. The culture supernatant was collected and subject to protein A purification. Next, the protein A column was equilibrated with 10× column volume of an equilibration buffer (25 mM Tris, 150 mM NaCl, pH 8.0), and the culture supernatant was then loaded to the equilibrated protein A column. The column was then washed with 6× column volume of a equilibration buffer (25 mM Tris, 150 mM NaCl, pH 8.0). The protein sample was eluted by 6× column volume of an elution buffer (100 mM acetate, 20 mM NaCl, pH 3.0), and pH was adjusted to 6.5-7 by a buffer containing 1 M HEPES, pH 8.0. The results indicate that all six HCB301_v5 proteins (SPT_G4_v5, SPT_G1_v5, PST_G1_v5, SP_G4_v5, SP_G1_v5, and PS_G1_v5) can be expressed and harvested with a high purity.

In addition, the amino acid sequences of SEQ ID NOs: 1-6 were analyzed using the deimmunization tool (Immune Epitope Database and Analysis Resource; Dhanda et al. "Development of a strategy and computational application to select candidate protein analogues with reduced HLA binding and immunogenicity." Immunology 153.1 (2018): 118-132) to identify immunogenic regions. No immunogenicity was identified.

Example 2. Determination of the Whole Cell Binding Ability to CD47 Transfected (Tf) CHO-S Cells To determine the whole cell binding ability of the HCB301_v5 proteins to CD47 expressed on cell surface, tf CHO-S cells expressing human CD47 (CD47 tf CHO-S) were used as target cells. $5 \times 10^4$ cells were incubated with serially diluted HCB301_v5 proteins at indicated concentrations (0.2 pM, 1.91 pM, 15.3 pM, 122.1 pM, 1.0 nM, 7.8 nM, 62.5 nM, and 500 nM) in FACS buffer (phosphate-buffered saline (PBS) supplemented with 4% fetal bovine serum (FBS)) at 4° C. for 30 minutes. After the incubation, the cells were washed twice with FACS buffer, and then incubated with R-Phycoerythrin-AffiniPure Goat Anti-Human IgG (Jackson ImmunoResearch, Cat #: 109-115-098) at 4° C. for 30 minutes. The samples were analyzed using a CytoFLEX flow cytometer (Beckman Coulter Inc., CA, USA). Hu5F9-G4 was used as a positive control. Anti-PD-L1 VHH (2H4) was used as a negative control.

Figure 2:
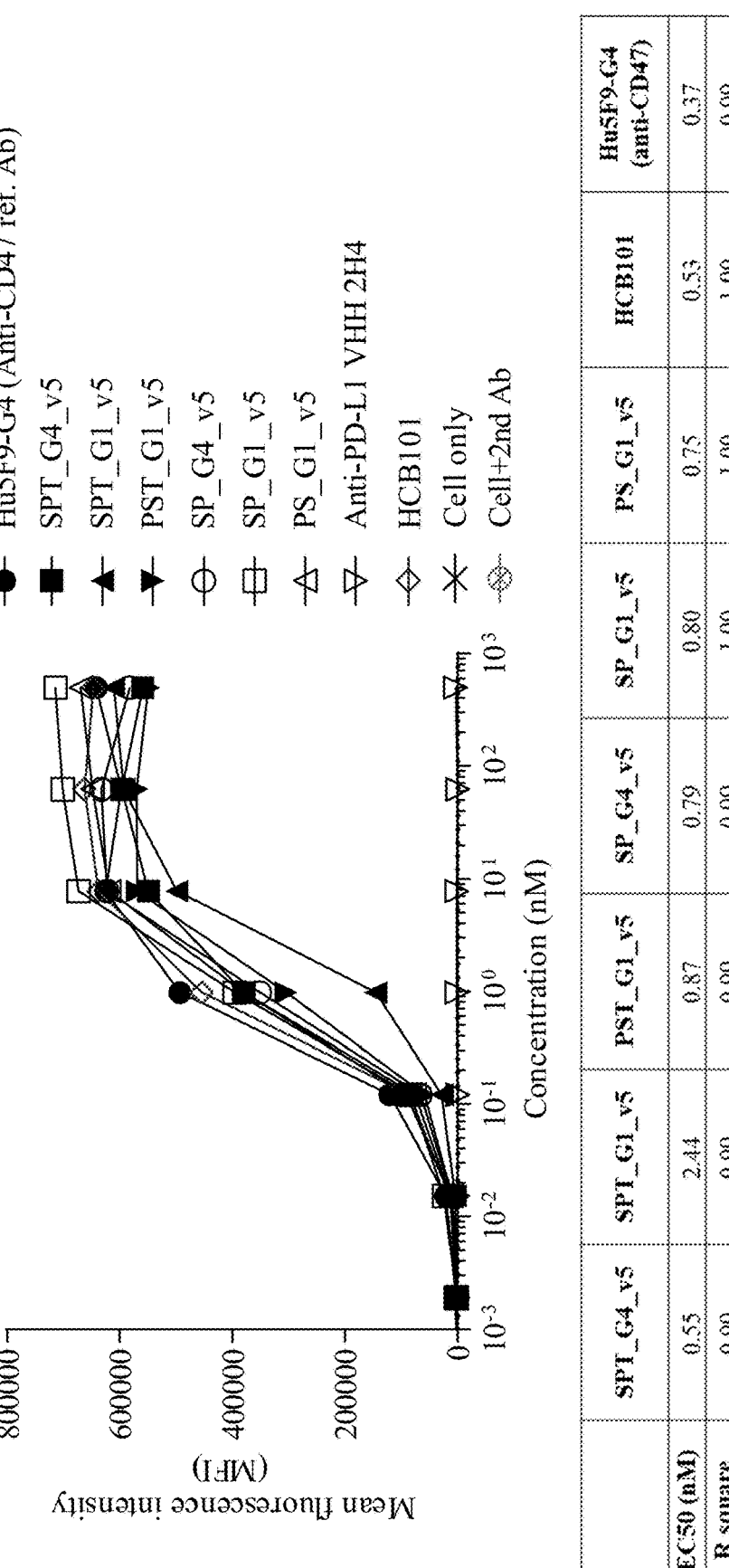
FIG. 2 shows whole cell binding results of HCB301 v5 proteins to transfected CHO-S cells expressing CD47.

As shown in FIG. 2, all six HCB301_v5 proteins can bind to CD47 tf CHO-S cells. The EC50 values were determined according to the binding curves. Specifically, SPT_G1_v5 demonstrated comparable binding efficacy only at high concentrations, whereas at low concentrations it showed diminished effectiveness. Conversely, the other 5 HCB301_v5 proteins exhibited equivalent effectiveness to the positive control Hu5F9-G4 (anti-47 ref. Ab) throughout the concentration range for binding to CD47 tf CHO-S cells. By contrast, no binding signals were detected for the negative control anti-PD-L1 VHH (2H4).

Example 3. Determination of the Whole Cell Binding Ability to PD-L1 Tf CHO-S Cells To determine the whole cell binding ability of the HCB301_v5 proteins to PD-L1 expressed on cell surface, tf CHO-S cells expressing human PD-L1 (PD-L1 tf CHO-S) were used as target cells. $5 \times 10^4$ cells were incubated with serially diluted HCB301_v5 proteins at indicated concentrations (0.2 pM, 1.91 pM, 15.3 pM, 122.1 pM, 1.0 nM, 7.8 nM, 62.5 nM, and 500 nM) in FACS buffer (phosphate-buffered saline (PBS) supplemented with 4% fetal bovine serum (FBS)) at 4° C. for 30 minutes. After the incubation, the cells were washed twice with FACS buffer, and then incubated with R-Phycoerythrin-AffiniPure Goat Anti-Human IgG (Jackson ImmunoResearch, Cat #: 109-115-098) at 4° C. for 30 minutes. The samples were analyzed using a CytoFLEX flow cytometer (Beckman Coulter Inc., CA, USA). Anti-PD-L1 VHH (2H4) was used as a positive control. Hu5F9-G4 was used as a negative control.

Figure 3:
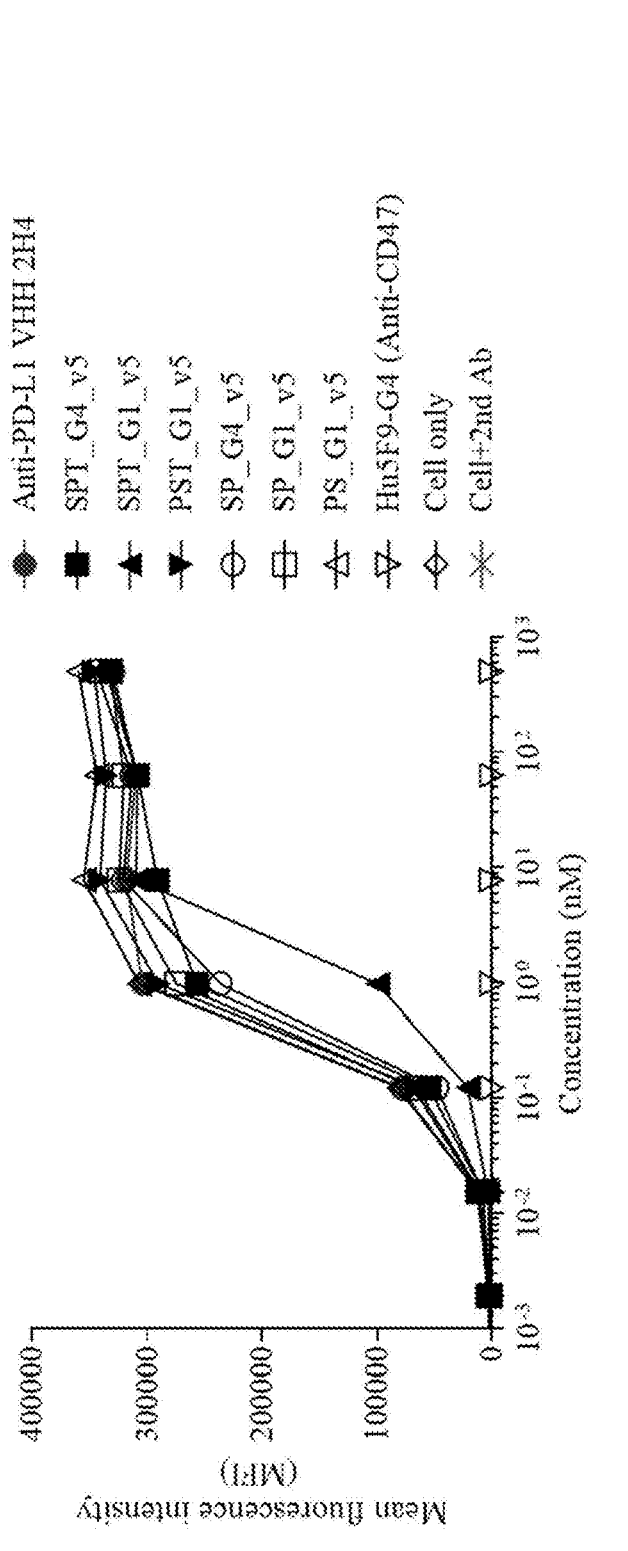
FIG. 3 shows whole cell binding results of HCB301 v5 proteins to transfected CHO-S cells expressing PD-L1.

As shown in FIG. 3, all six HCB301_v5 proteins can bind to PD-L1 tf CHO-S cells. The EC50 values were also determined according to the binding curves. Again, SPT_G1_v5 demonstrated comparable binding efficacy only at high concentrations, whereas the other 5 HCB301_v5 proteins exhibited equivalent effectiveness to the positive control anti-PD-L1 VHH (2H4) throughout the concentration range for binding to CD47 tf CHO-S cells. By contrast, no binding signals were detected for the negative controls Hu5F9-G4 (anti-47 ref. Ab).

Example 4. Determination of HCB301_v5 Binding Ability to Plate-Bound Human TGFβ Proteins To determine the binding ability of HCB301_v5 proteins to human TGFβ, a binding titration ELISA assay was performed using of the HCB301_v5 proteins at indicated concentrations (6.4 pM, 32.0 pM, 160.0 pM, 0.8 nM, 4.0 nM, 20 nM, 100 nM, or 500 nM). G4_TGFβRII_mt4 (SEQ ID NO: 21) was used as a positive control. HCB101 (SEQ ID NO: 20) was used as a negative control. A 96-well EIA microplate was coated with 0.5 µg/ml human TGFβ (TGFβ 1, TGFβ2, or TGFβ3) overnight at 4° C. After blocking with 1×PBS containing 5% skim milk, diluted HCB301_v5 proteins were added and incubated at 24° C. for 1 hour. The unbound proteins were removed by washing the wells with 1×PBST (1×PBS containing 0.1% Tween 20) three times. An HRP-conjugated secondary antibody (1:5000) was added to the wells at 24° C. for 1 hour. After the incubation, excess secondary antibodies were removed by washing the wells with 1×PBST three times. Finally, 3,3',5,5'-Tetramethylbenzidine (TMB) was added to the color development. The reaction was stopped and HRP activity was measured using a spectrophotometer at 450 nm.

Figure 4A:
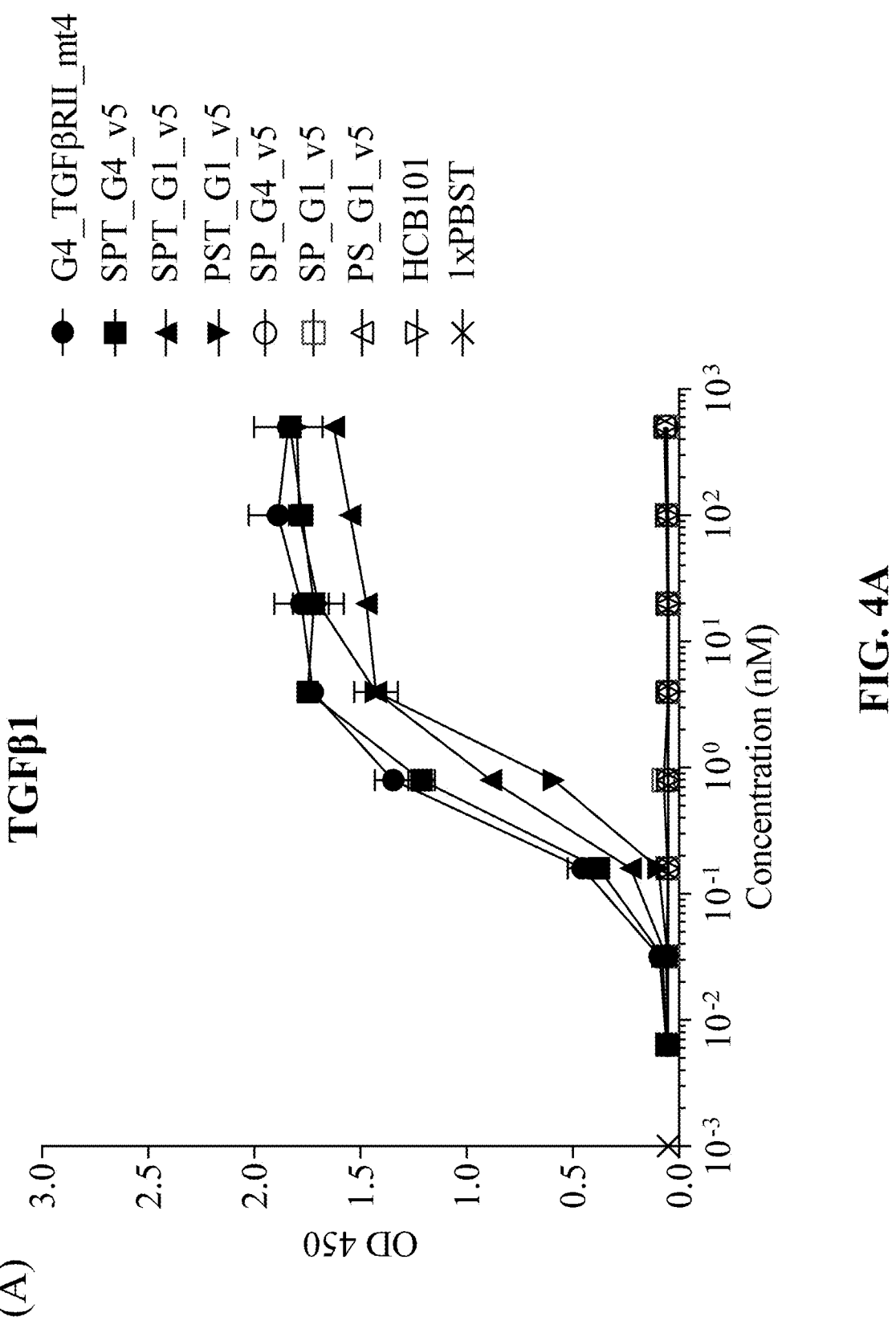
FIG. 4A shows human TGFβ1 binding results of HCB301 v5 proteins to by ELISA. G4_TGFβRII_mt4 was used as a positive control.
Figure 4B:
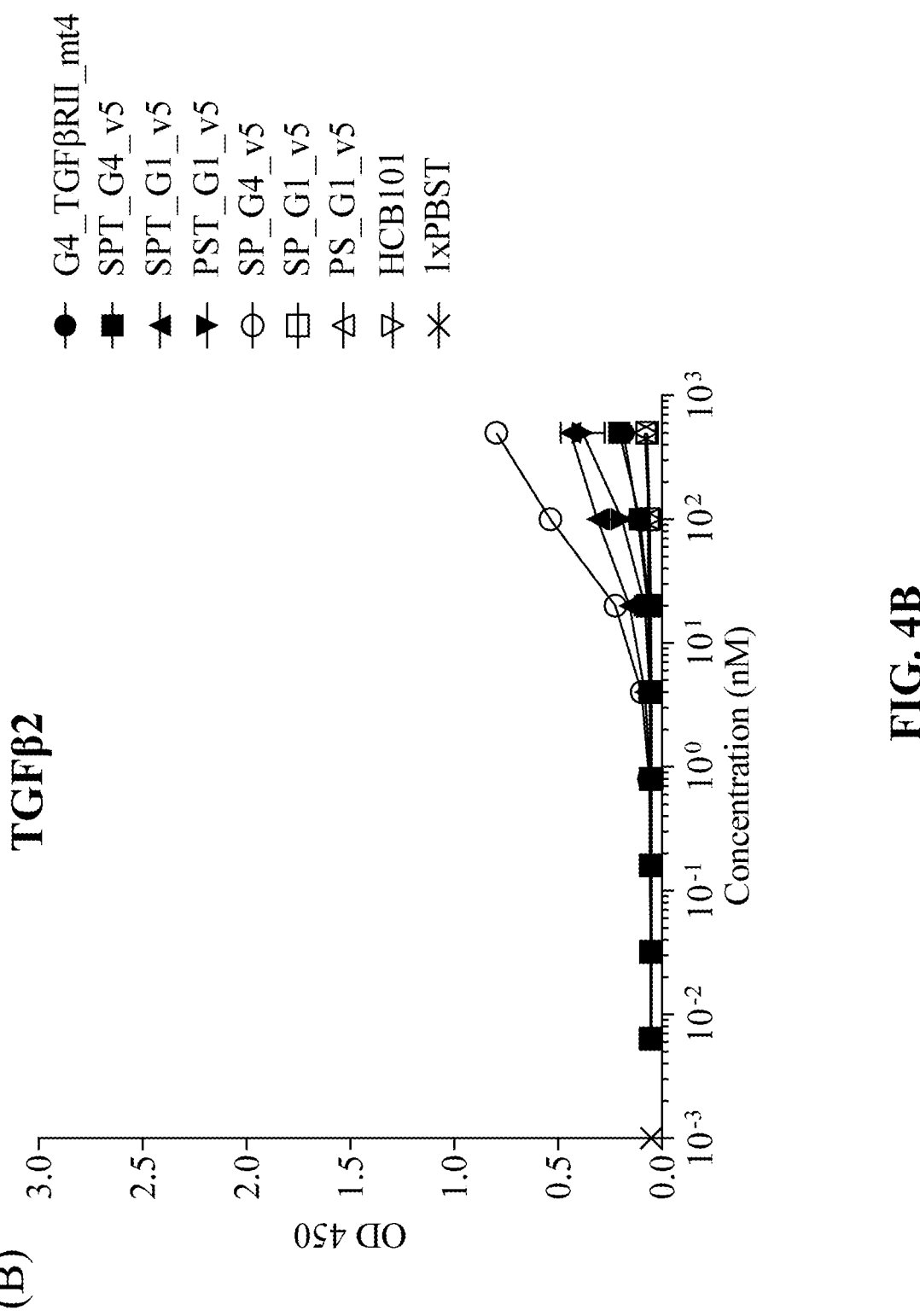
FIG. 4B shows human TGFβ2 binding results of HCB301 v5 proteins to by ELISA. G4_TGFβRII_mt4 was used as a positive control.
Figure 4C:
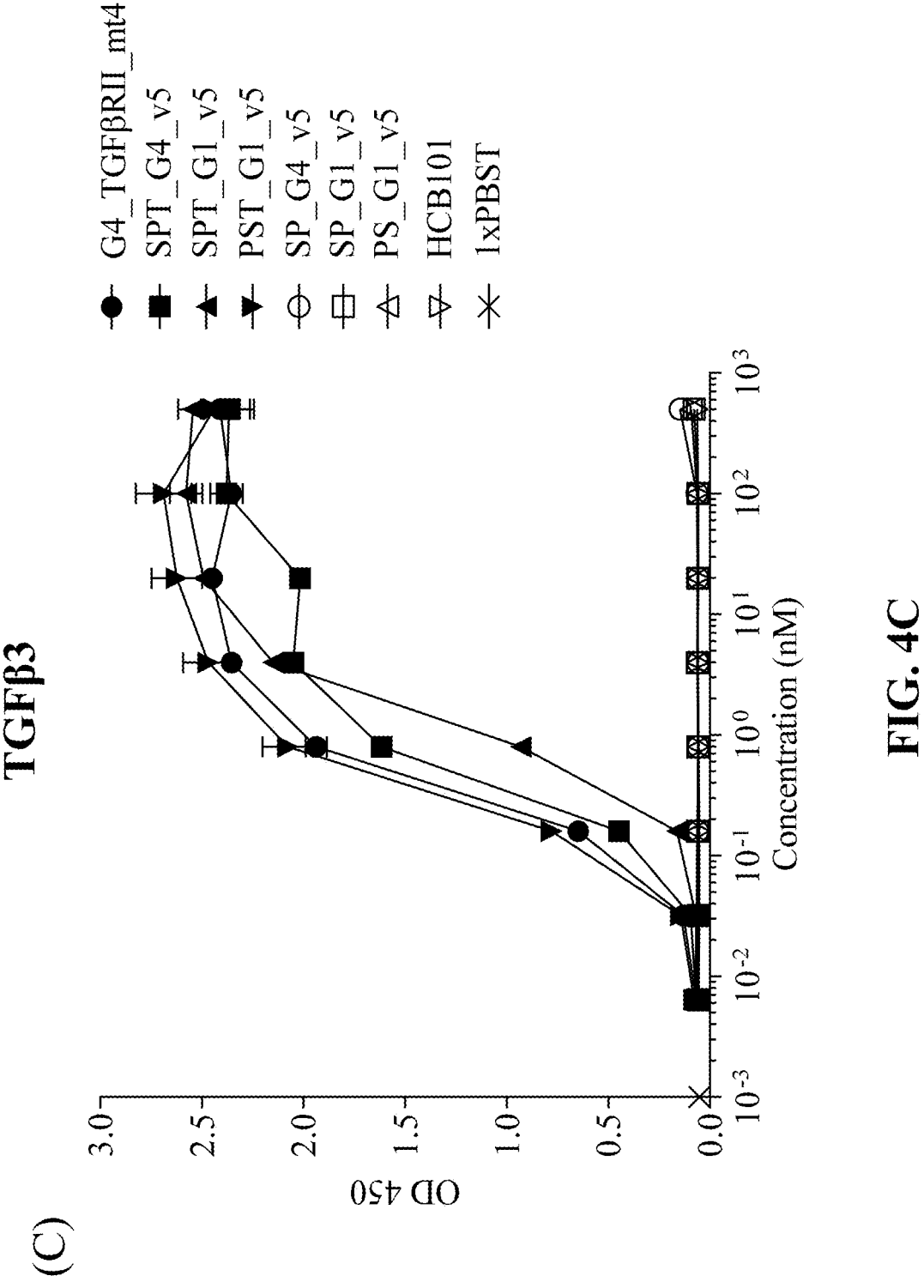
FIG. 4C shows human TGFβ3 binding results of HCB301 v5 proteins to by ELISA. G4_TGFβRII_mt4 was used as a positive control.

As shown in FIGS. 4A-4C, the three triple-targeting formats of HCB301_v5 proteins, SPT_G4_v5, SPT_G1_v5, PST_G1_v5, demonstrated the ability to bind to hTGFβ1 (FIG. 4A) and hTGFβ3 (FIG. 4C), but barely bound to hTGFβ2 (FIG. 4B). By contrast, the three double-targeting formats of HCB301_v5 proteins without a TGFβRII_mt4 extracellular domain, SP_G4_v5, SP_G1_v5, PS_G1_v5, as well as the negative controls did not bind to hTGFβ31, hTGFβ2, or hTGFβ3.

Example 5. Determination of the Whole Cell Binding Ability to CD47-Expressing Tumor Cells To determine the whole cell binding ability of HCB301_v5 proteins to CD47 and PD-L1 expressed on tumor cell surface, hypopharyngeal carcinoma FaDu cells and non-small cell lung cancer NCI-H460 expressing endogenous CD47 were used as target cells. $5 \times 10^4$ tumor cells were incubated with serially diluted HCB301_v5 proteins at indicated concentrations (0.2 pM, 1.91 pM, 15.3 pM, 122.1 pM, 1.0 nM, 7.8 nM, 62.5 nM, and 500 nM) in FACS buffer (PBS supplemented with 4% FBS) at 4° C. for 30 minutes. After the incubation, the cells were washed twice with FACS buffer, and then incubated with R-Phycoerythrin-AffiniPure Goat Anti-Human IgG (Jackson ImmunoResearch, Cat #: 109-115-098) at 4° C. for 30 minutes. The samples were analyzed using a CytoFLEX flow cytometer (Beckman Coulter Inc., CA, USA). HCB101 was used as the positive control. G4_TGFβRII_mt4 was used as a negative control.

Figure 5A:
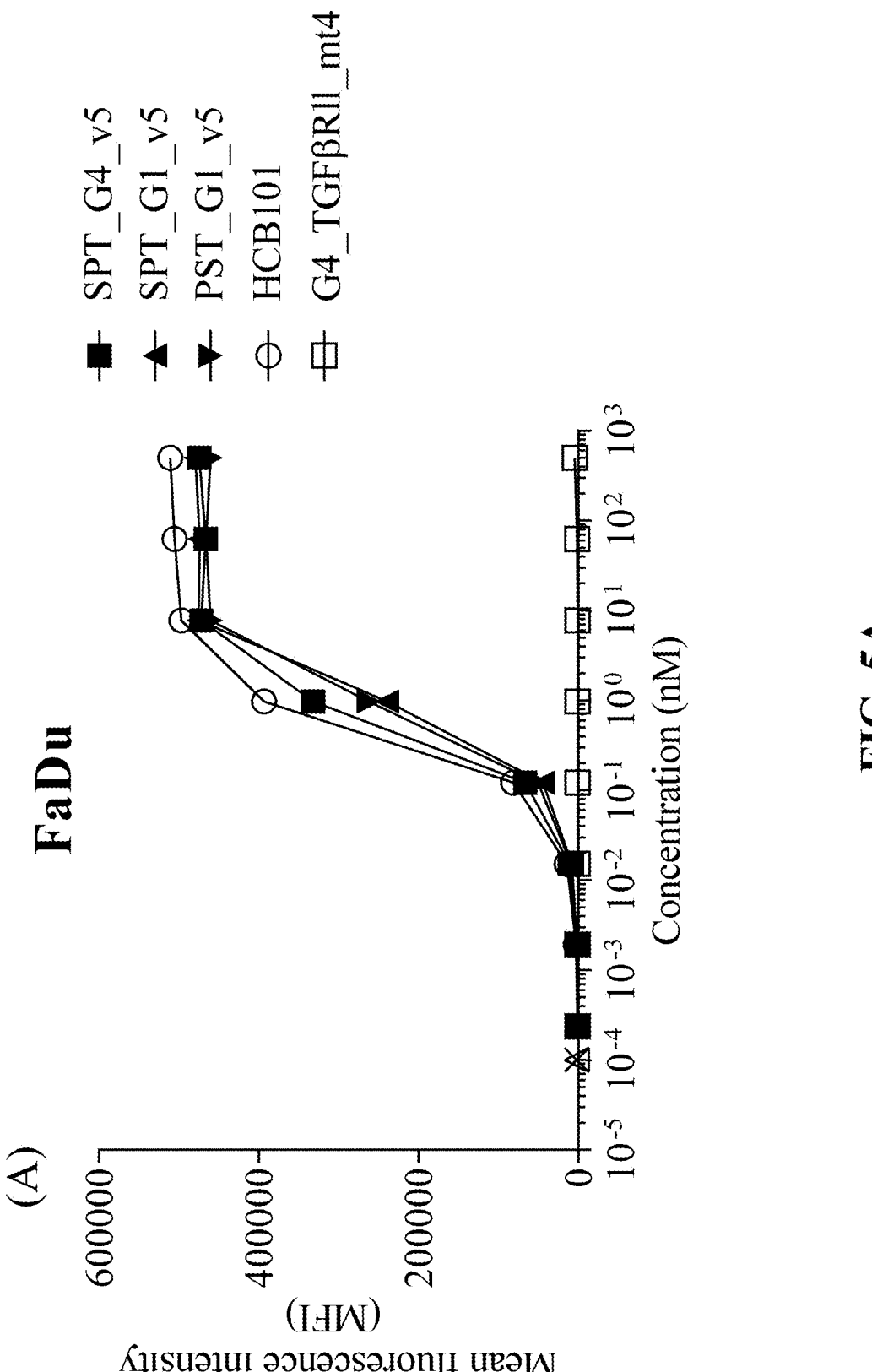
FIGS. 5A-5B show whole cell binding results of HCB301 v5 proteins to CD47-expressing FaDu cells and NCI-H460 cells, respectively.
Figure 5B:
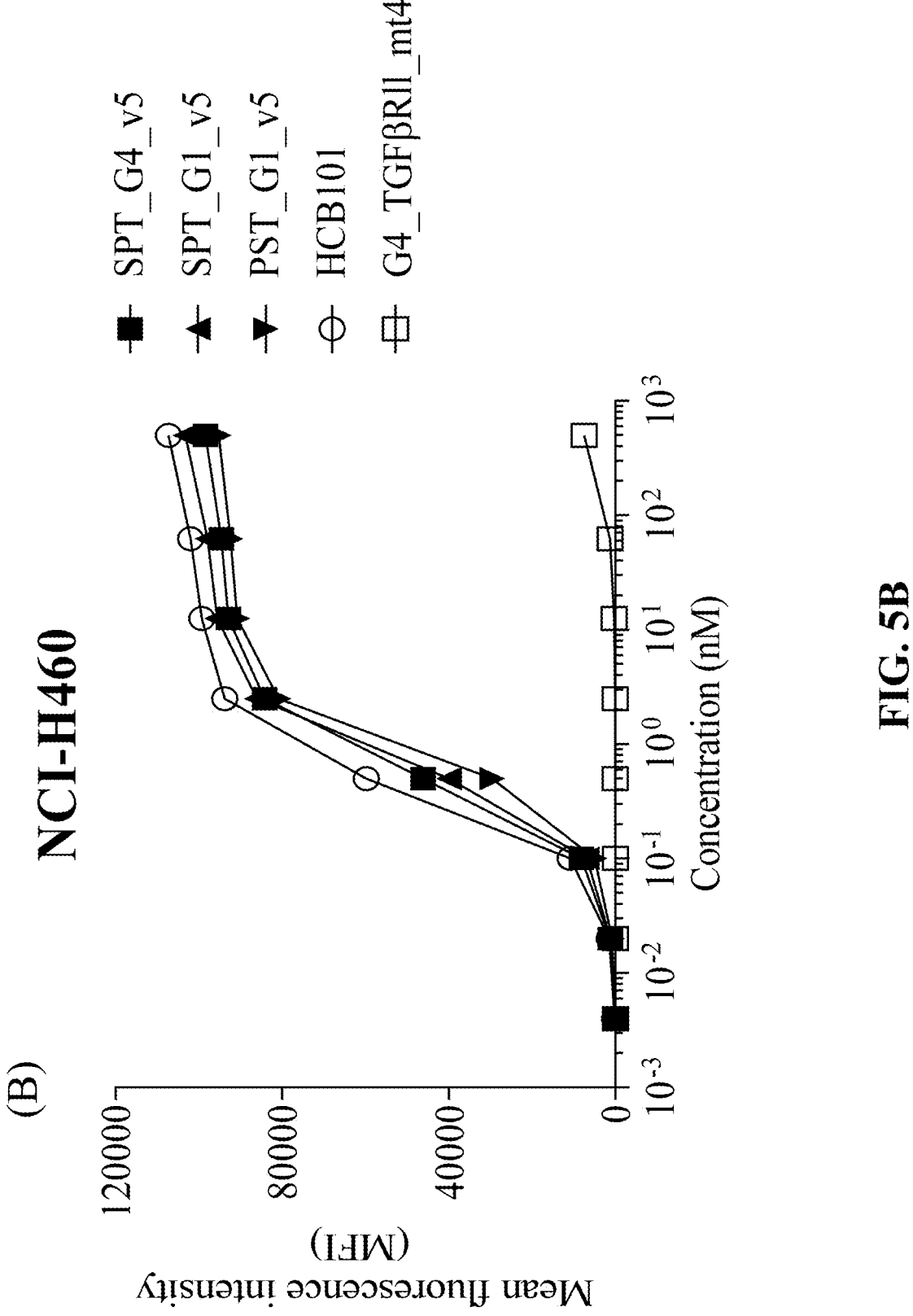

As shown in FIGS. 5A-5B, all three triple-targeting formats of HCB301_v5 proteins, SPT_G4_v5, SPT_G1_v5, PST_G1_v5 can bind to FaDu cells (FIG. 5A) and NCI-H460 cells (FIG. 5B) as effectively as the positive control HCB101. By contrast, no binding signal was detected for the negative control G4_TGFβRII_mt4.

Example 6. Selective Binding to PD-L1-Expressing Cells

The selective binding ability of HCB301_v5 proteins to PD-L1-expressing cells was determined as follows. DLD1 cells were labeled with CellTrace™ CFSE (Thermo, Cat #: C34554) and tf DLD1 cells expressing PD-L1 (PD-L1 tf DLD1) were labeled with Celltrace™ (Thermo, Cat #:

C34557) according to the instructions provided by manufacturer. $5 \times 10^4$ cells/well of CellTrace™ CFSE-labeled DLD1 cells and $5 \times 10^4$ cells/well of CellTrace™ violet-labeled PD-L1 tf DLD1 cells were incubated with serially diluted HCB301_v5 proteins at indicated concentrations (0.2 pM, 1.91 pM, 15.3 pM, 122.1 pM, 1.0 nM, 7.8 nM, 62.5 nM, and 500 nM) in FACS buffer (PBS supplemented with 4% FBS) at 4° C. for 30 minutes. After the incubation, the cells were washed twice with FACS buffer, and then incubated with R-Phycoerythrin-AffiniPure Goat Anti-Human IgG (Jackson ImmunoResearch, Cat #: 109-115-098) at 4° C. for 30 minutes. The samples were analyzed using a CytoFLEX flow cytometer (Beckman Coulter Inc., CA, USA). Afterwards, the cells were gated according to PE signals to calculate the percentages of different cell types by Kaluza analysis software (Beckman Coulter Inc.). Hu5F9-G4, HCB101, Atezolizumab, and anti-PD-L1 VHH (2H4) were used as positive controls and G4_TGFβRII_mt4 used as a negative control.

Figure 6A:
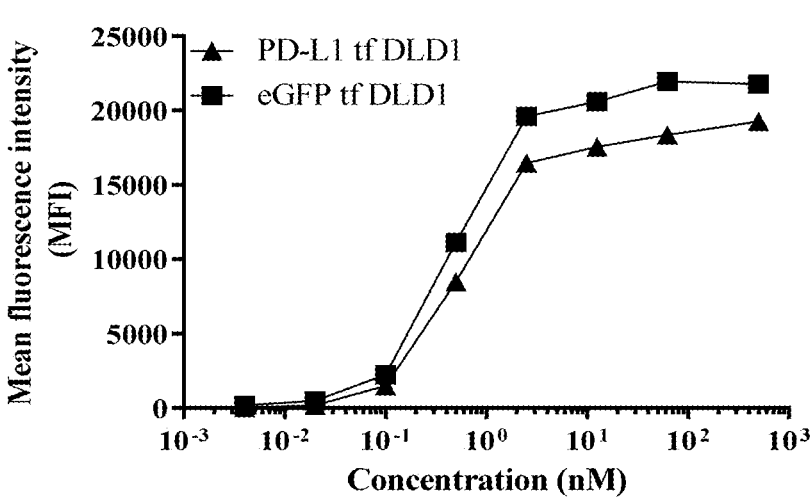
FIGS. 6A-6K show the whole cell binding results of HCB301 v5 proteins to PD-L1-expressing DLD1 cells and DLD1 cells, respectively.
Figure 6B:
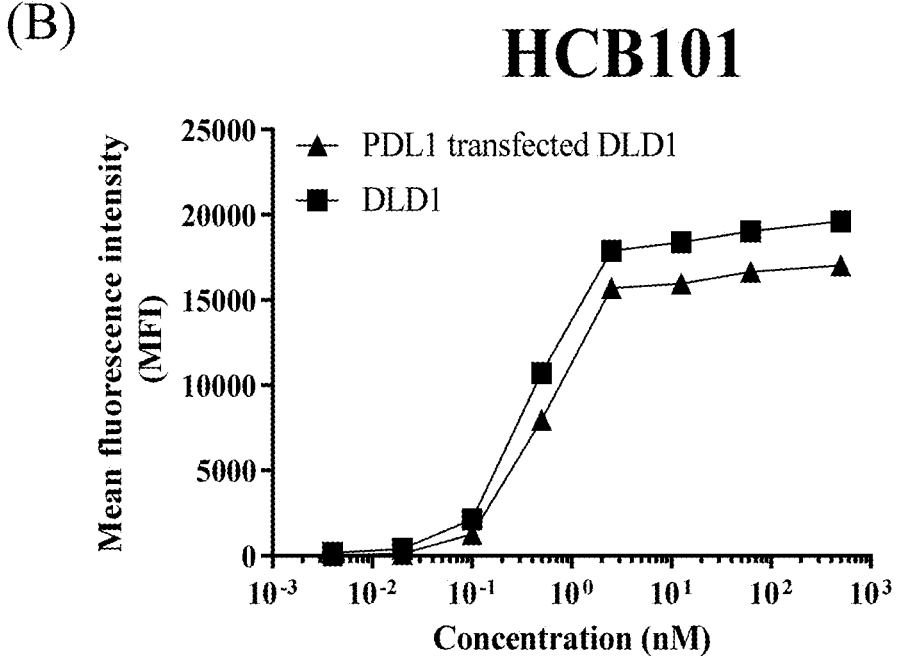
Figure 6C:
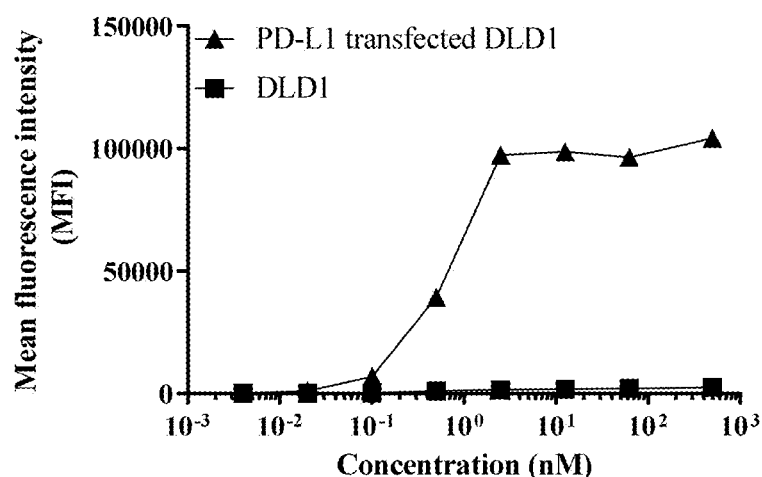
Figure 6D:
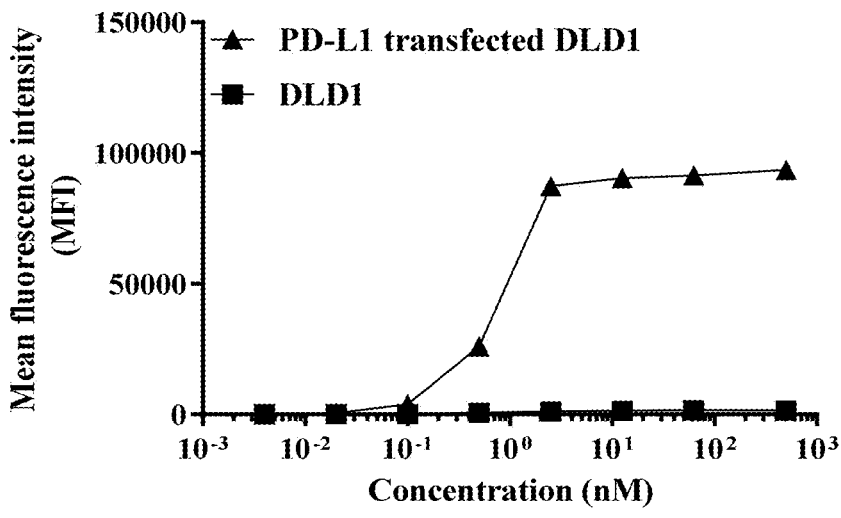
Figure 6E:
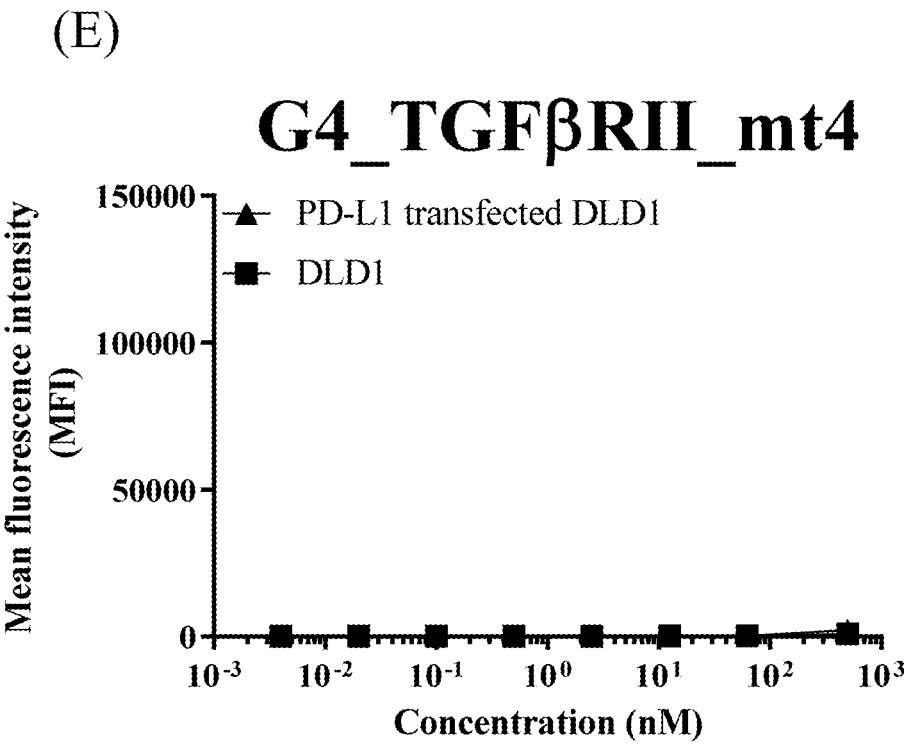
Figure 6F:
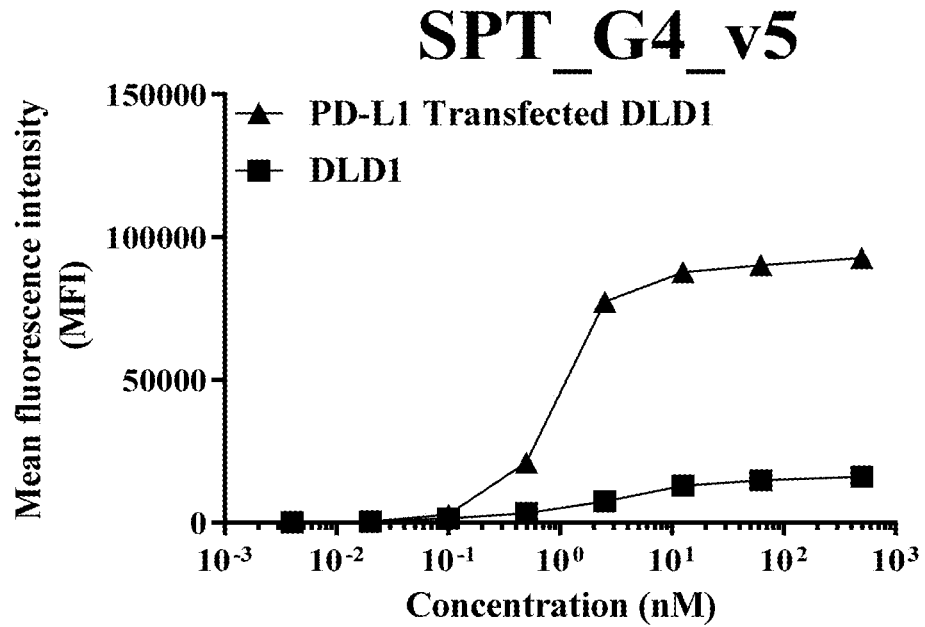
Figure 6G:
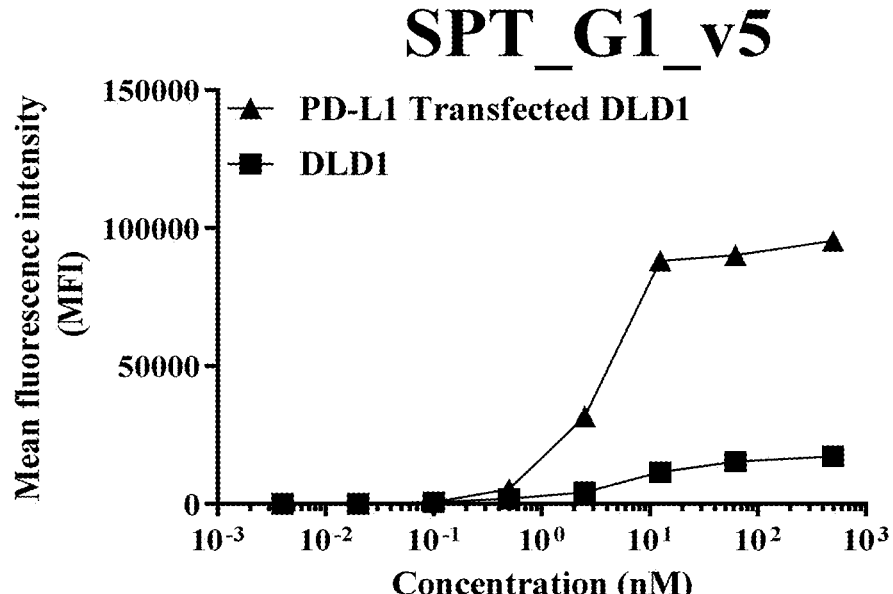
Figure 6H:
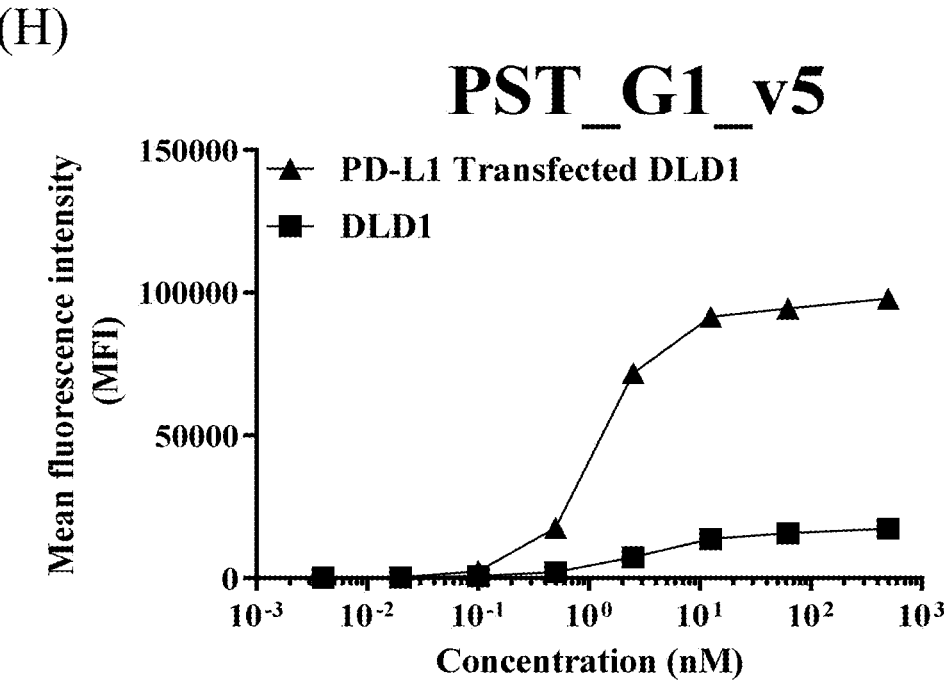
Figure 6I:
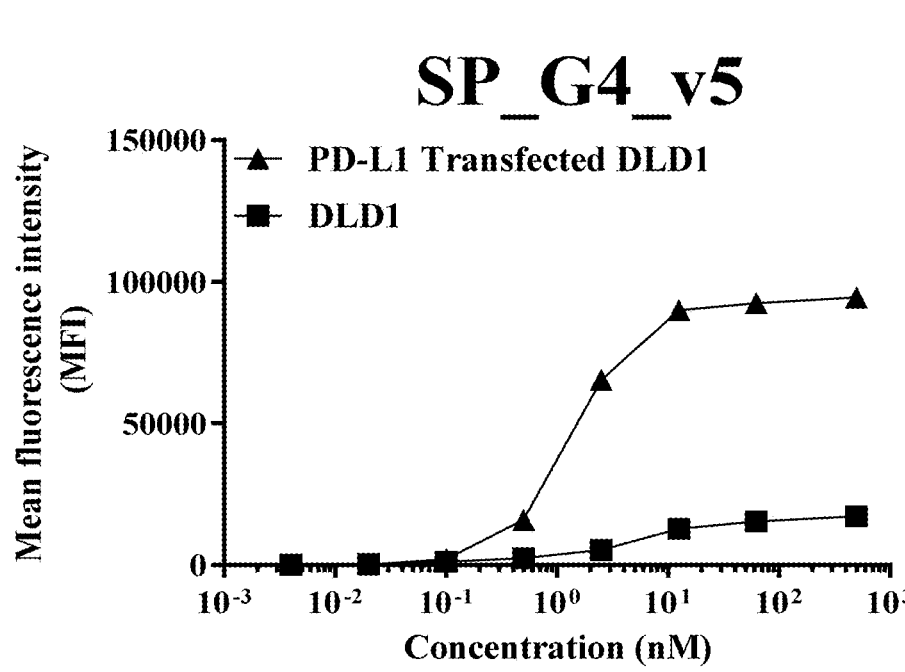
Figure 6J:
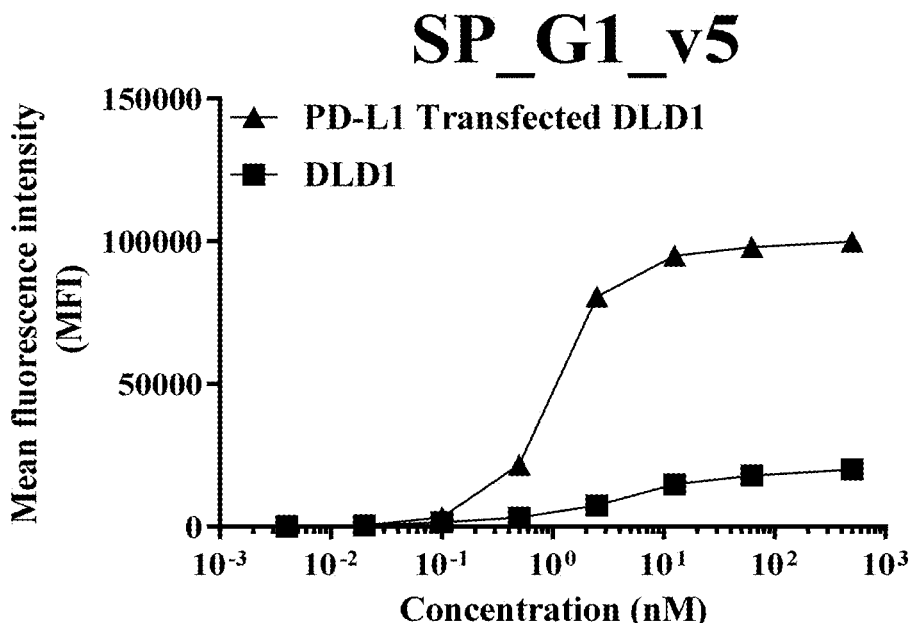
Figure 6K:
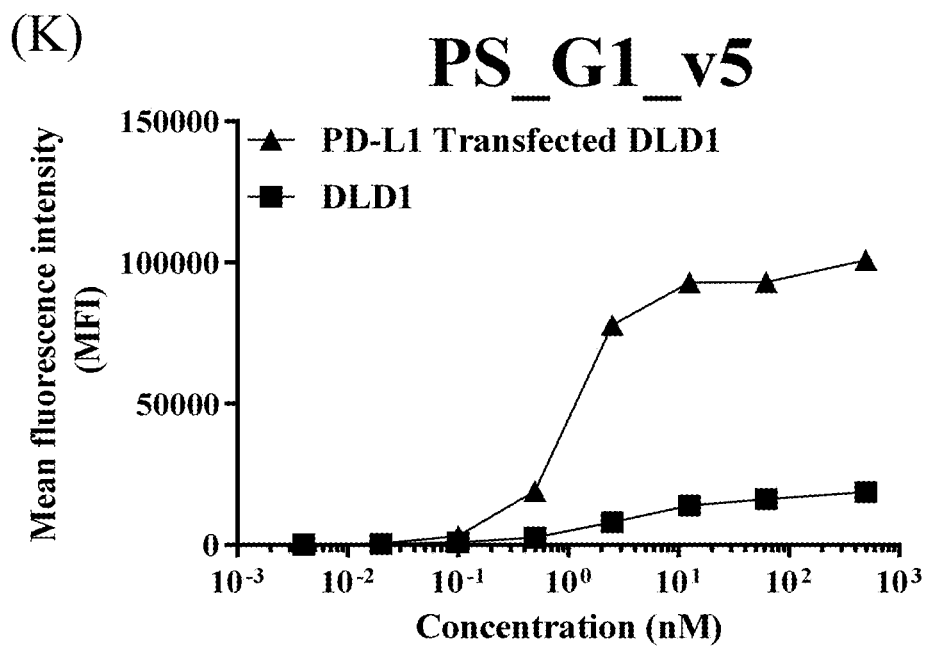

As shown in FIGS. 6F-6K, all six HCB301_v5 proteins preferentially bound to PD-L1 tf DLD1 cells in the mixture of PD-L1 tf DLD1 cells and DLD1 cells (at a ratio of 1 to 1). This selective binding to PD-L1 tf DLD1 cells was also evident in two of the positive controls, Atezolizumab, and anti-PD-L1 VHH (2H4) (FIGS. 6C-6D). By contrast, the other two of the positive controls, Hu5F9-G4 and HCB101 (FIGS. 6A-6B) exhibited similar binding effectiveness between PD-L1 tf DLD1 cells and DLD1 cells. No binding signal was detected for the negative control G4_TGFβRII_mt4 (FIG. 6E).

Example 7. Determination of Hemagglutination (HA) Activity

To determine the HA activity induced by the HCB301_v5, RBCs were prepared from whole blood of healthy donor by washing with 0.9% sodium chloride buffer twice, and then RBC were resuspended in a 0.9% sodium chloride buffer. The HCB301_v5 proteins were serially diluted (3-fold) to a final concentration of 500 nM, 166.7 nM, 55.6 nM, 18.5 nM, 6.2 nM, 2.1 nM, 685.8 pM, 228.6 pM, 76.2 pM, 25.4 pM, or 8.4 pM, and were incubated in a round-bottom 96-well plate with $8 \times 10^6$ RBC solution per well at room temperature (RT) overnight. After the incubation, agglutinated RBCs coated wells evenly, whereas non-agglutinated cells formed a distinct red dot at the bottom of the well. Hu5F9-G4 was used a positive control. h1G4 (heavy chain: SEQ ID NO: 36; light chain: SEQ ID NO: 37) was used as negative control. The sequence of G1_TGFβRII_mt4 is set forth in SEQ ID NO: 22.

Figure 7:
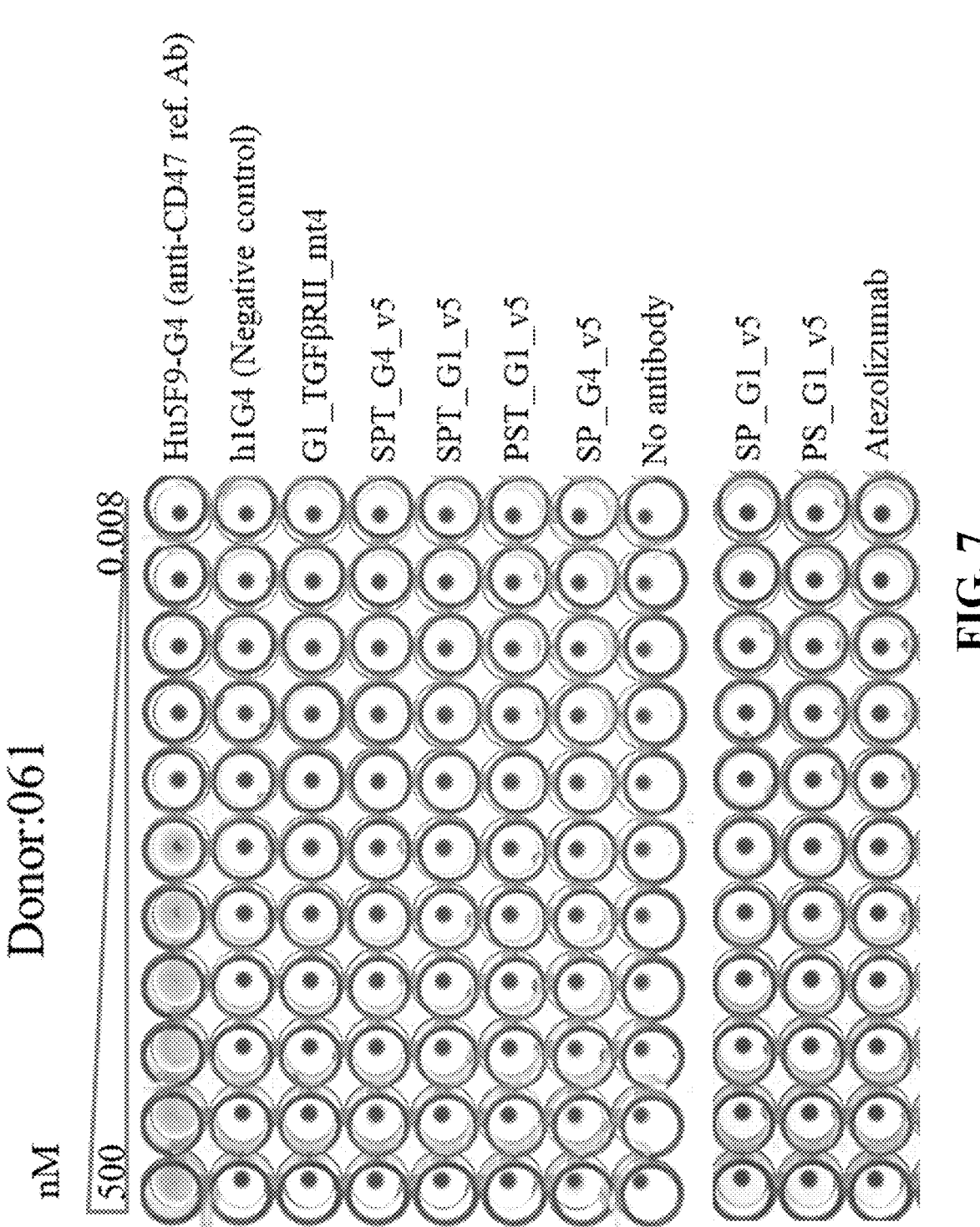
FIG. 7 shows RBC hemagglutination activity induced by HCB301_v5 proteins.

An image of the plate was captured on the next day after overnight incubation, as shown in FIG. 7. The image indicates that only Hu5F9-G4 induced HA activity at high concentrations, whereas none of the six HCB301_v5 proteins induced HA activity throughout the concentration range indicated above.

Example 8. Determination of the Whole Cell Binding Ability to Platelets and Induction of the Subsequent Platelet Phagocytosis by Mouse Macrophages To determine the binding ability of HCB301_v5 proteins to platelets, $5 \times 10^5$ human platelets were incubated with serially diluted HCB301_v5 proteins at indicated concentrations (0.07 pM, 0.4 pM, 2.6 pM, 15.4 pM, 92.5 pM, 0.6 nM, 3.3 nM, and 20.0 nM) in FACS buffer (PBS supplemented with 4% FBS) at 4° C. for 30 minutes. After the incubation, the platelets were washed twice with FACS buffer, and then incubated with R-Phycoerythrin-AffiniPure Goat Anti-Human IgG (Jackson ImmunoResearch, Cat #: 109-115-098) at 4° C. for 30 minutes. The samples were analyzed using a CytoFLEX flow cytometer (Beckman Coulter Inc., CA, USA). Hu5F9-G4 was used as a positive control. h1G4 was used as a negative control.

To determine the macrophage-mediated phagocytosis induced by HCB301_v5 proteins on platelets, phagocytosis assays were performed as follows. Platelets were labeled with 5 nM CellTrace™ CFSE (Thermo, Cat #: C34554) at 37° C. for 10 minutes, and then washed by complete DMEM medium. $5 \times 10^5$ cells/well CFSE-labeled platelets cells (target cells) were incubated with the HCB301_v5 proteins that were serially diluted at indicated concentrations (0.5 pM, 5.0 pM, 50.0 pM, 0.5 nM, 5.0 nM, 50.0 nM, and 500.0 nM) in a low-binding 96-well U-shaped bottom plate at 37° C. for 30 minutes. Afterwards, $5 \times 10^4$ Raw264.7 mouse microphages were added to each well and the plate was incubated at 37° C. for 2 hours. The Raw264.7 cells were stained with PE-Cyanine 7 conjugated F4/80 antibody (eBioscience, Cat #: 25-4801-82). The phagocytosis ability of the HCB301_v5 proteins was evaluated by calculating the percentage of CFSE+ F4/80+ from macrophages (indicating macrophages phagocytosed CFSE-labeled Jurkat cells) over the total F4/80 signals from macrophages by a CytoFlex flow cytometer (Beckman Coulter Inc.). Hu5F9-G4 was used as a positive control. h1G4 was used as a negative control.

Figure 8A:
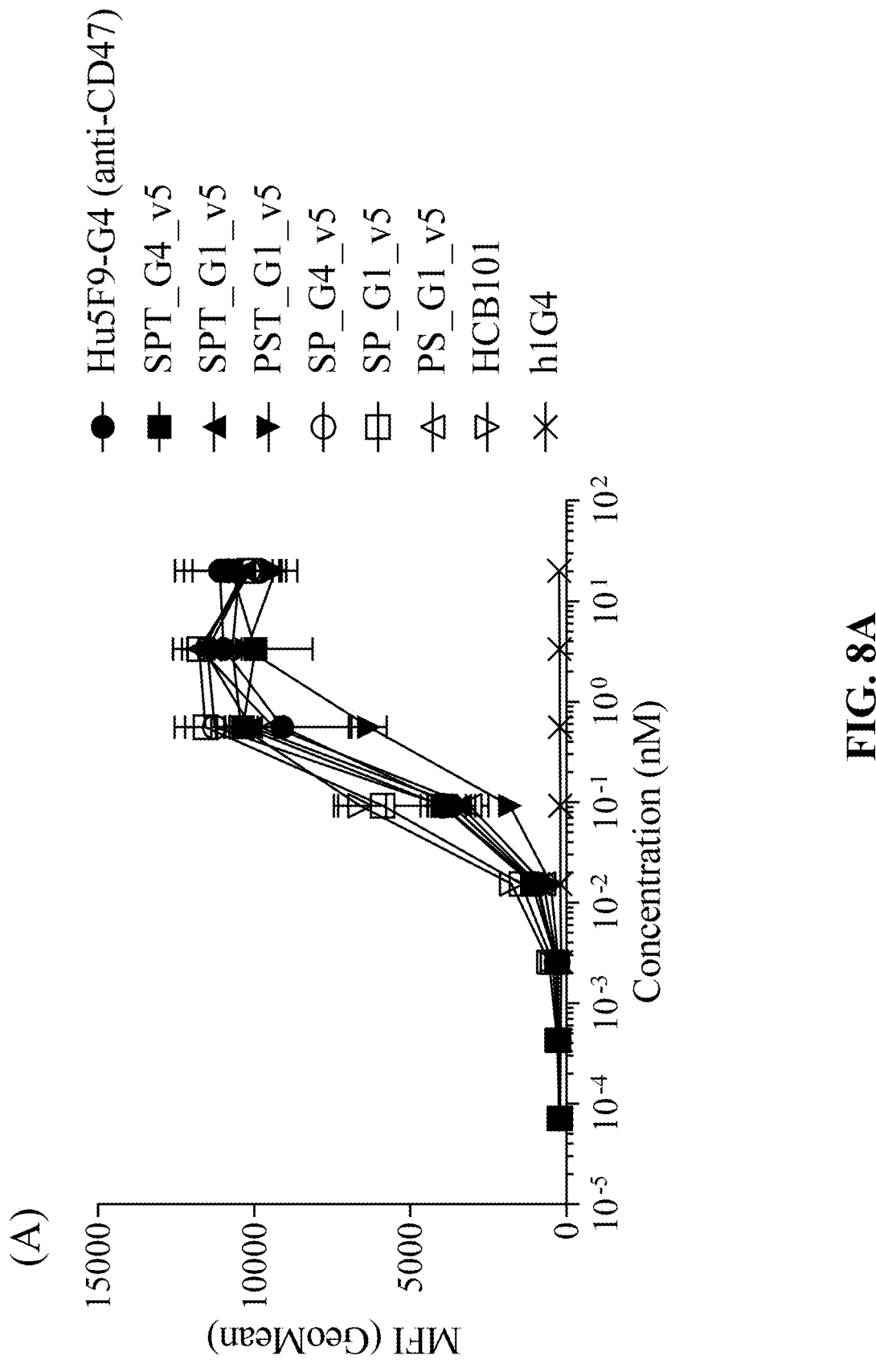
FIG. 8A shows platelet binding results of HCB301 v5 proteins.
Figure 8B:
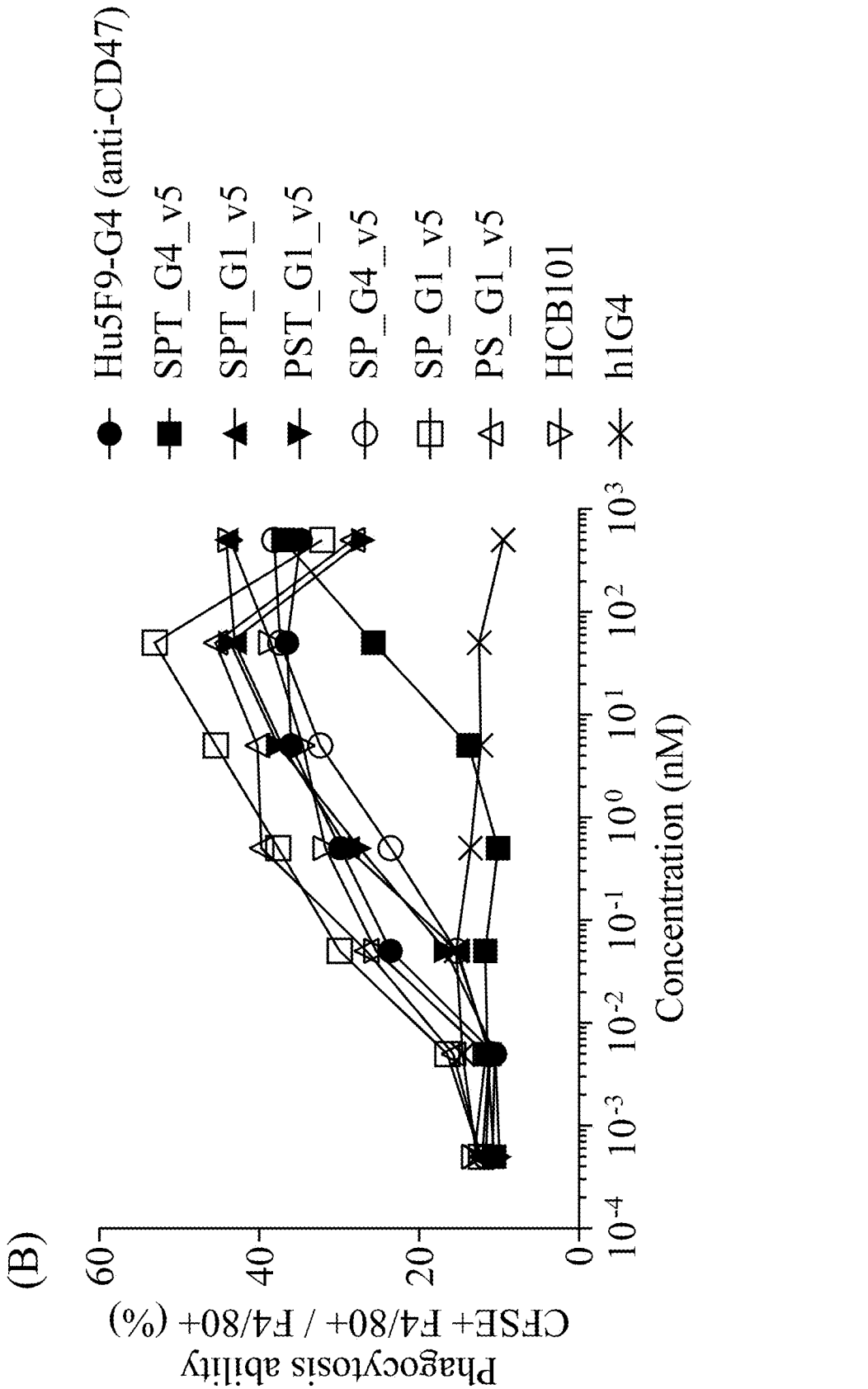
FIG. 8B shows the results of macrophage-mediated phagocytosis on platelet induced by HCB301_v5 proteins.

As shown in FIG. 8A, all six HCB301_v5 proteins, like the positive control Hu5F9-G4, exhibited a strong binding ability to platelets. Noteworthily, FIG. 8B shows that SPT_G4_v5 was less likely to trigger platelet phagocytosis by mouse macrophage Raw264.7 at lower concentrations. By contrast, the other five HCB301_v5 proteins and the positive control Hu5F9-G4, upon binding to platelet, induced evident phagocytosis.

Example 9. Determination of the Whole Cell Binding Ability to RBCs and Induction of the Subsequent RBC Phagocytosis by Human Macrophages To determine the binding ability of SPT_G4_v5 proteins to RBCs, $5 \times 10^5$ human RBCs were incubated with serially diluted SPT_G4_v5 proteins at indicated concentrations (0.3 pM, 1.3 pM, 6.4 pM, 32.0 pM, 160.0 pM, 0.8 nM, 4.0 nM, 20 nM, 100.0 nM, and 500.0 nM) in FACS buffer (PBS supplemented with 4% FBS) at 4° C. for 30 minutes. After the incubation, the RBCs were washed twice with FACS buffer, and then incubated with R-Phycoerythrin-AffiniPure Goat Anti-Human IgG (Jackson ImmunoResearch, Cat #: 109-115-098) at 4° C. for 30 minutes. The samples were analyzed using a CytoFLEX flow cytometer (Beckman Coulter Inc., CA, USA). Hu5F9-G4 was used as a positive control. Anti-PD-L1 VHH (2H4) used as a negative control.

To determine the macrophage-mediated phagocytosis induced by SPT_G4_v5 protein on RBCs by human MDM cells, phagocytosis assay was performed as follows. RBCs were labeled with 5 nM CellTrace™ CFSE (Thermo, Cat #: C34554) at 37° C. for 10 minutes, and them washed by complete RPMI-1640 medium. $5 \times 10^5$ cells/well CFSE-labeled RBC (target cells) were incubated with the SPT_G4_v5 protein that were serially diluted at indicated concentrations (2.0 pM, 20.0 pM, 0.2 nM, 2.0 nM, and 20.0 nM) in a low-binding 96-well U-shaped bottom plate at 37° C. for 30 minutes. Afterwards, $5 \times 10^4$ human MDM cells were added to each well and the plate was incubated at 37° C. for 2 hours. The human MDM cells were stained with PE-Cyanine 7 conjugated CD14 antibody (eBioscience, Cat #: 25-0149-42). The phagocytosis ability of the SPT_G4_v5 proteins was evaluated by calculating the percentage of CFSE+ CD14+ from macrophages (indicating macrophages phagocytosed CFSE-labeled RBCs) over the total CD14 signals from macrophages by a CytoFlex flow cytometer (Beckman Coulter Inc.). Hu5F9-G4 was used as a positive control. h1G4 was used as a negative control.

Figure 9A:
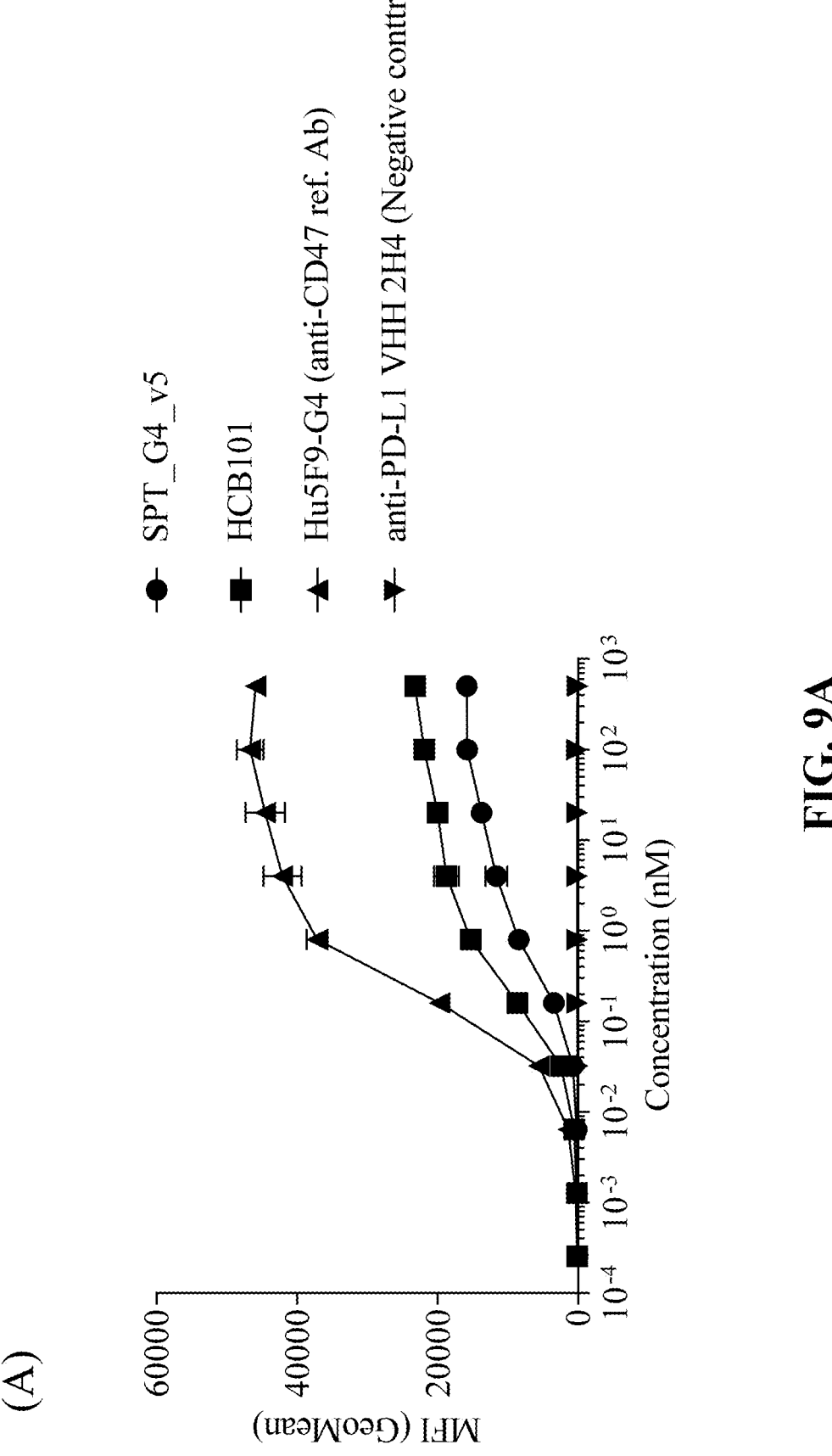
FIG. 9A shows RBC binding results of the HCB301 v5 protein SPT_G4_v5. Hu5F9-G4 was used as a positive control. Anti-PD-L1 VHH (2H4) was used as a negative control.
Figure 9B:
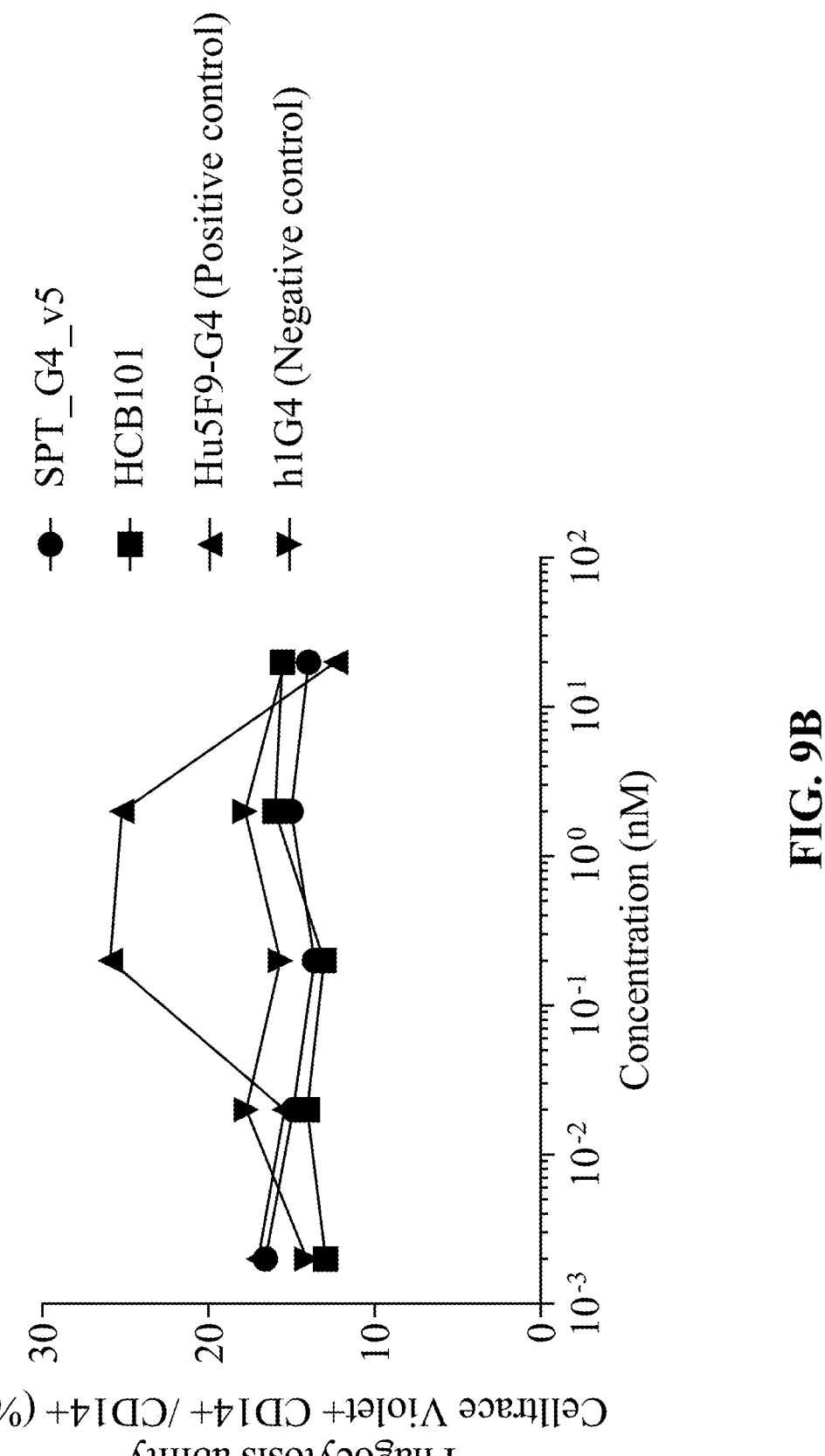
FIG. 9B shows the results of macrophage-mediated phagocytosis on RBC induced by the HCB301_v5 protein SPT_G4_v5. Hu5F9-G4 was used as a positive control. H1G4 was used as a negative control.

As shown in FIGS. 9A-9B, the positive control Hu5F9-G4 exhibited a strong binding ability to human RBCs (FIG. 9A), and this led to phagocytosis of human RBCs by human MDM cells (FIG. 9B). By contrast, SPT_G4_v5 exhibited a low binding affinity to human RBCs, and this binding did not lead to phagocytosis.

Example 10. Determination of the Blocking Effect on the Interaction Between SIRPα and CD47

To determine the SIRPα ligand blocking ability of HCB301 v5 proteins, flow cytometry-based assays were performed using CD47 tf CHO-S cells as the target cells. Specifically, $3 \times 10^4$ cells/well of CD47 tf CHO-S cells were incubated with the HCB301_v5 proteins were serially diluted at indicated concentrations (0.2 pM, 1.9 pM, 15.2 pM, 122.1 pM, 976.6 pM, 7.8 nM, 62.5 nM, and 500 nM) in FACS buffer (PBS supplemented with 4% FBS), together with a fixed concentration of biotinylated SIRPα_G4 ("biotin SIRP Fc"; SEQ ID NO: 23) at 4° C. for 30 minutes. After washing, streptavidin-PE (eBioscience, Cat #: EBS12-4317-87) was added at 0.3 μg per well, and PE signals from the cells were analyzed using a CytoFLEX flow cytometer (Beckman Coulter Inc.). Hu5F9-G4 and HCB101 were used as positive controls. Anti-PD-L1 VHH (2H4) was used as a negative control.

Figure 10:
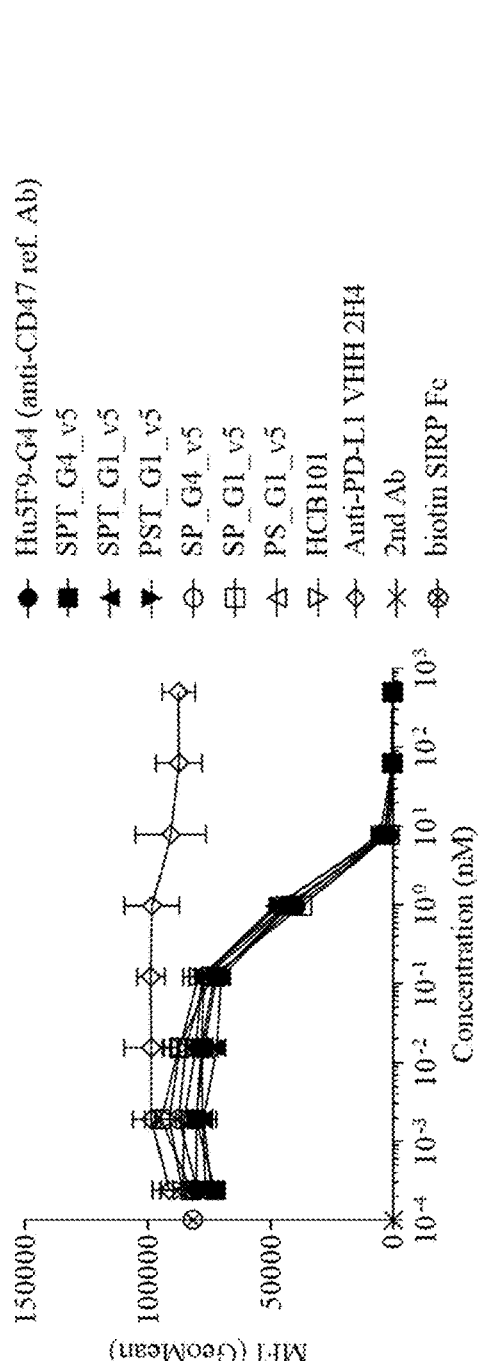
FIG. 10 shows SIRPα/CD47 blocking results of HCB301 v5 proteins on transfected CHO-S cells expressing CD47. "Biotin SIRP Fc" stands for biotinylated SIRPα_G4.

As shown in FIG. 10, all six HCB301_v5 proteins as well as the positive controls, Hu5F9-G4 and HCB101, exhibited a comparable blocking effect on the interaction between SIRPα and CD47. By contrast, the interaction between SIRPα and CD47 was not interfered by the negative control, Anti-PD-L1 VHH (2H4).

Example 11. Induction of Phagocytosis of PD-L1 tf Tumor Cells by Human MDM Cells To determine the macrophage-mediated phagocytosis induced by HCB301_v5 proteins on PD-L1 tf cancer cells by human MDM cells, phagocytosis assay was performed as follows. PD-L1 tf OVA-GFP DLD1 cells were labeled with 5 nM CellTrace™ CFSE (Thermo, Cat #: C34554) at 37° C. for 10 minutes, and then washed by complete RPMI-1640 medium. $6 \times 10^4$ cells/well CFSE-labeled PD-L1 tf OVA-GFP DLD1 cells (target cells) were incubated with the HCB301_v5 proteins that were serially diluted at indicated concentrations (5 pM, 50.0 pM, 0.5 nM, 5.0 nM, 50.0 nM, and 500.0 nM) in a low-binding 96-well U-shaped bottom plate at 37° C. for 30 minutes. Afterwards, $3 \times 10^4$ human MDM cells were added to each well and the plate was incubated at 37° C. for 2 hours. The human MDM cells were stained with PE-Cyanine 7 conjugated CD14 antibody (eBioscience, Cat #: 25-0149-42). The phagocytosis ability of the HCB301_v5 proteins was evaluated by calculating the percentage of CFSE+ CD14+ from macrophages (indicating macrophages phagocytosed CFSE-labeled PD-L1 tf OVA-GFP DLD1 cells) over the total CD14 signals from macrophages by a CytoFlex flow cytometer (Beckman Coulter Inc.). Hu5F9-G4 and HCB101 were used as positive controls. h1G4 was used as a negative control.

Figure 11:
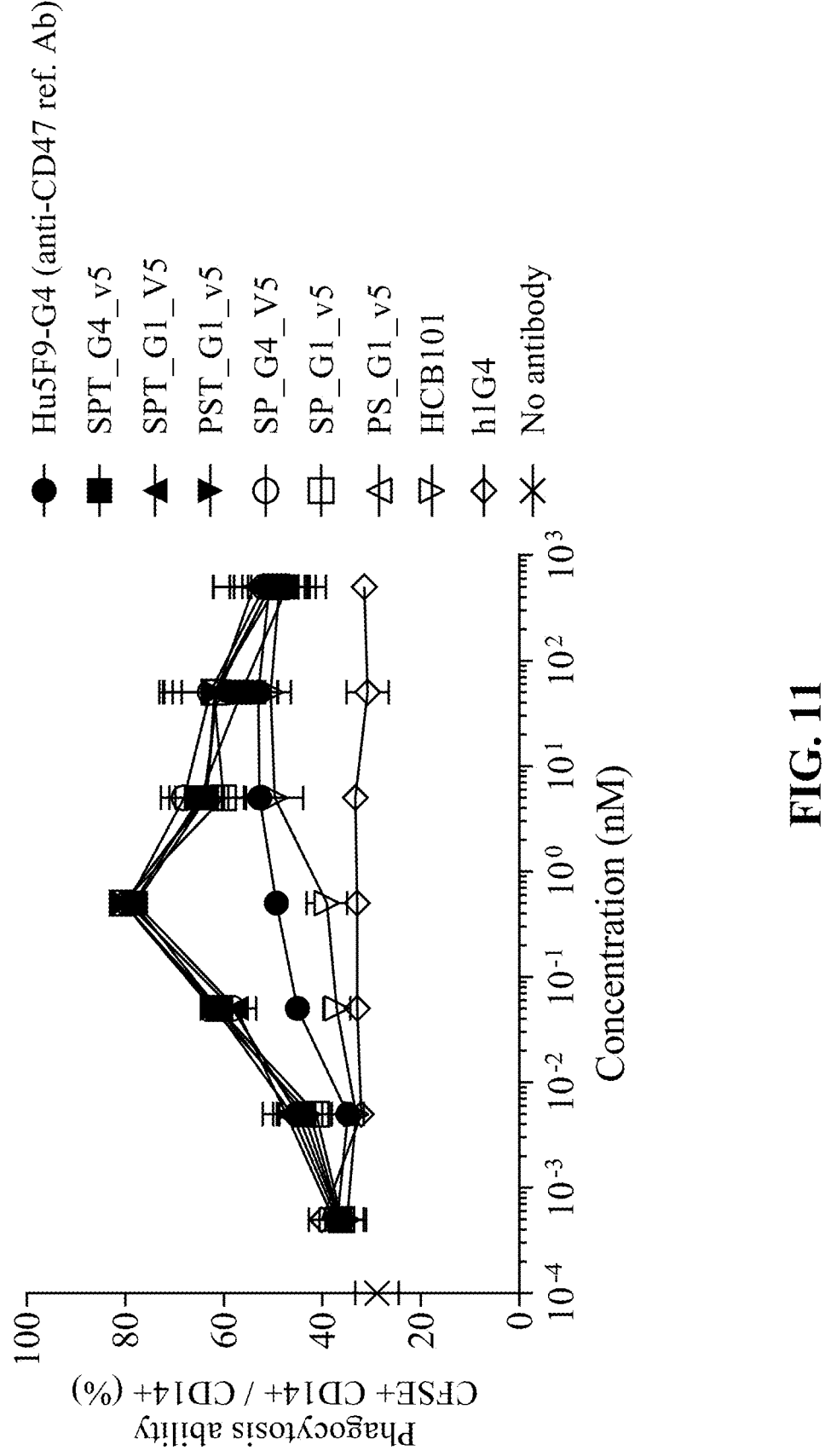
FIG. 11 shows the results of macrophage-mediated phagocytosis on PD-L1-expressing OVA-GFP DLD1 cells.

As shown in FIG. 11, all six HCB301_v5 proteins triggered stronger phagocytosis activity against PD-L1 tf OVA-GFP DLD1 cells by human MDM cells as compared to positive control Hu5F9-G4 and HCB101. By contrast, the negative control h1G4 did not induce phagocytosis at the tested concentrations.

Example 12. Determination of the Blocking Effect on the Interaction Between PD-1 and PD-L1

The blocking effect of HCB301_v5 proteins to the interaction between PD-1 and PD-L1 tf CHO-S cells was determined as follows. $3 \times 10^4$ cells/well of PD-L1 tf CHO-S cells were incubated with the HCB301_v5 proteins that were serially diluted at indicated concentrations (0.2 pM, 1.9 pM, 15.2 pM, 122.1 pM, 976.6 pM, 7.8 nM, 62.5 nM, and 500 nM) in FACS buffer (PBS supplemented with 4% FBS), together with a fixed concentration of biotinylated PD1_G4 ("Biotin PD1 Fc"; SEQ ID NO: 34) at 4° C. for 30 minutes. After washing, streptavidin-PE (eBioscience, Cat #: EBS12-4317-87) was added at 0.3 μg per well, and PE signals from the cells were analyzed using a CytoFLEX flow cytometer (Beckman Coulter Inc.). Atezolizumab (an anti-PD-L1 antibody) and anti-PD-L1 VHH (2H4) were used as positive controls. HCB101 was used as a negative control.

As shown in FIG. 12, all six HCB301_v5 proteins as well as the positive control, Atezolizumab (an anti-PD-L1 antibody) and anti-PD-L1 VHH (2H4), exhibited similar blocking effect on the interaction between PD-1 and PD-L1. By contrast, the interaction between PD-1 and PD-L1 was not interfered by the negative control, HCB101.

Example 13. Inhibition of TGFβ-Induced Smad2 Reporter Activity

The ability of HCB301_v5 proteins to inhibit TGFβ1, TGFβ2, or TGFβ3-induced smad2 reporter activity was determined as follows. The HCB301_v5 proteins were serially diluted (5-fold) to final concentrations of 6.4 pM, 32.0 pM, 160.0 pM, 0.8 nM, 4.0 nM, 20.0 nM, 100.0 nM, and 500.0 nM. G4_TGFBRII_mt4 was used as a positive control and anti-PD-L1 VHH (2H4) was used as a negative control. $4 \times 10^3$ tf HEK293T cells expressing a smad2 reporter was incubated with the diluted HCB301 v5 proteins, together with 20 ng/ml TGFβ1, TGFβ2, and TGFβ3, respectively. After a 24-hour incubation at 37° C. in a 5% $CO_2$ incubator, luminescence signals were detected by Varioskan™ LUX multimode microplate reader (Thermo).

Figure 13A:
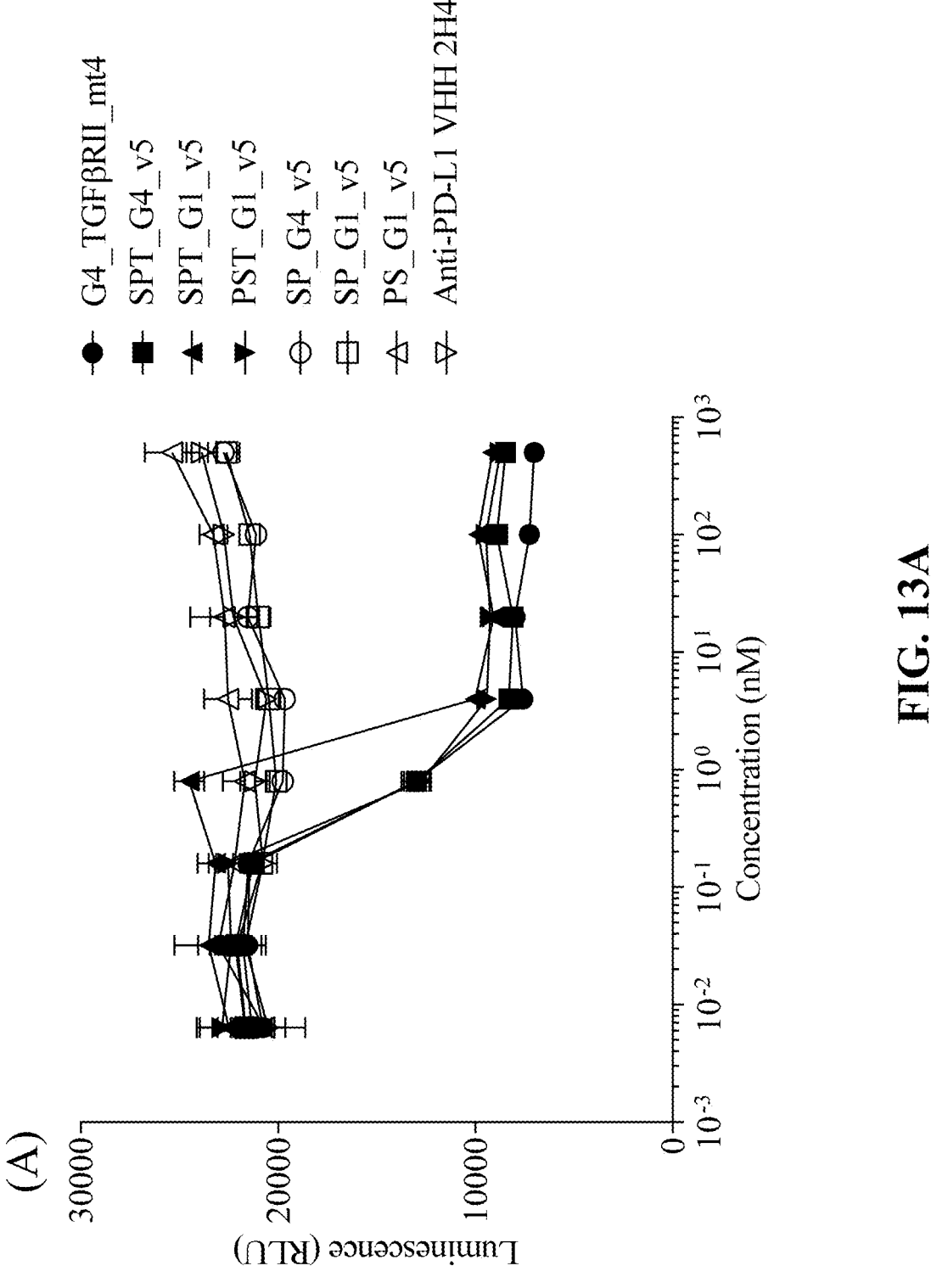
FIG. 13A shows the impact of HCB301 v5 proteins on TGFβI-mediated smad2 reporter activity.
Figure 13B:
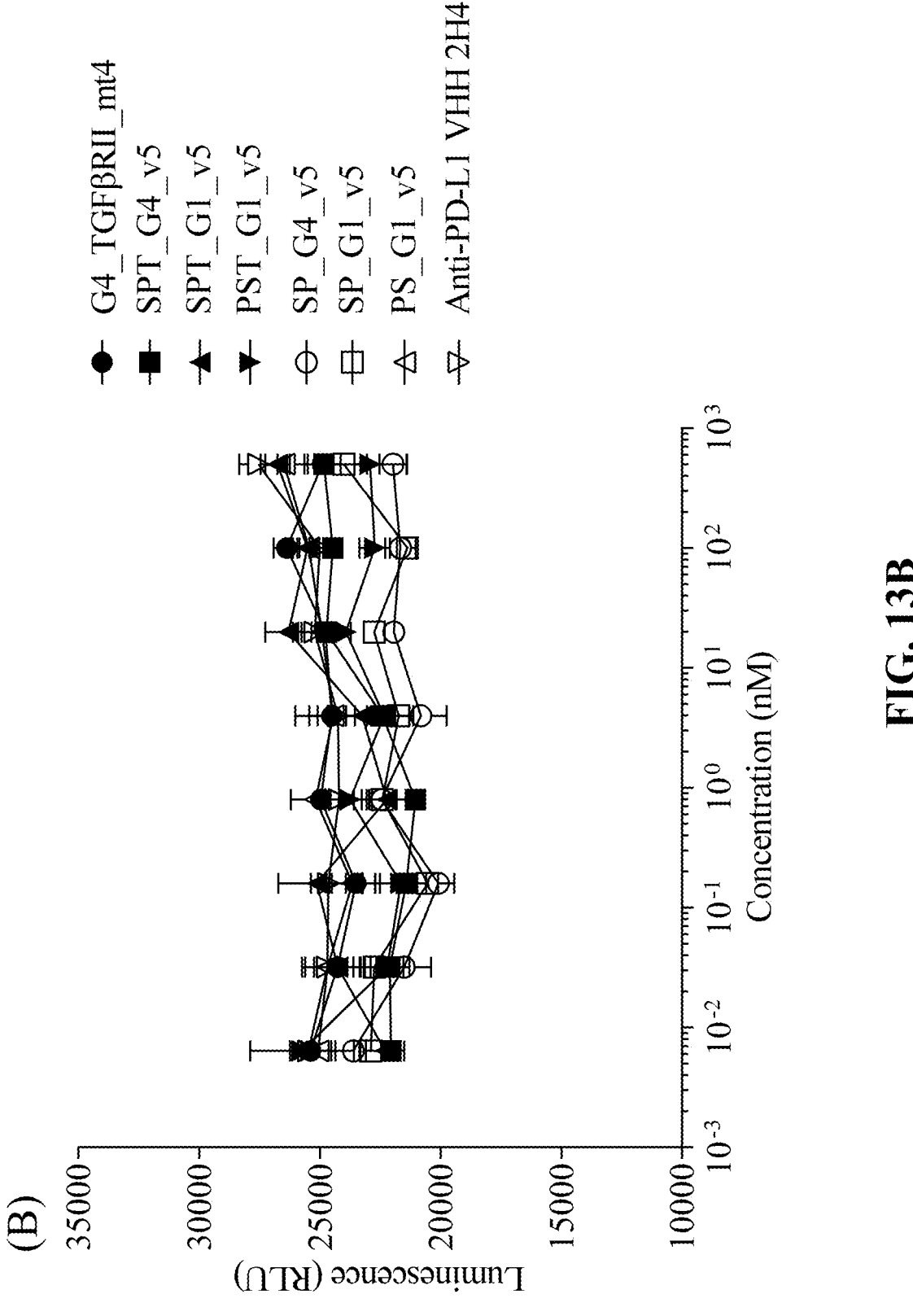
FIG. 13B shows the impact of HCB301 v5 proteins on TGFβ2-mediated smad2 reporter activity.
Figure 13C:
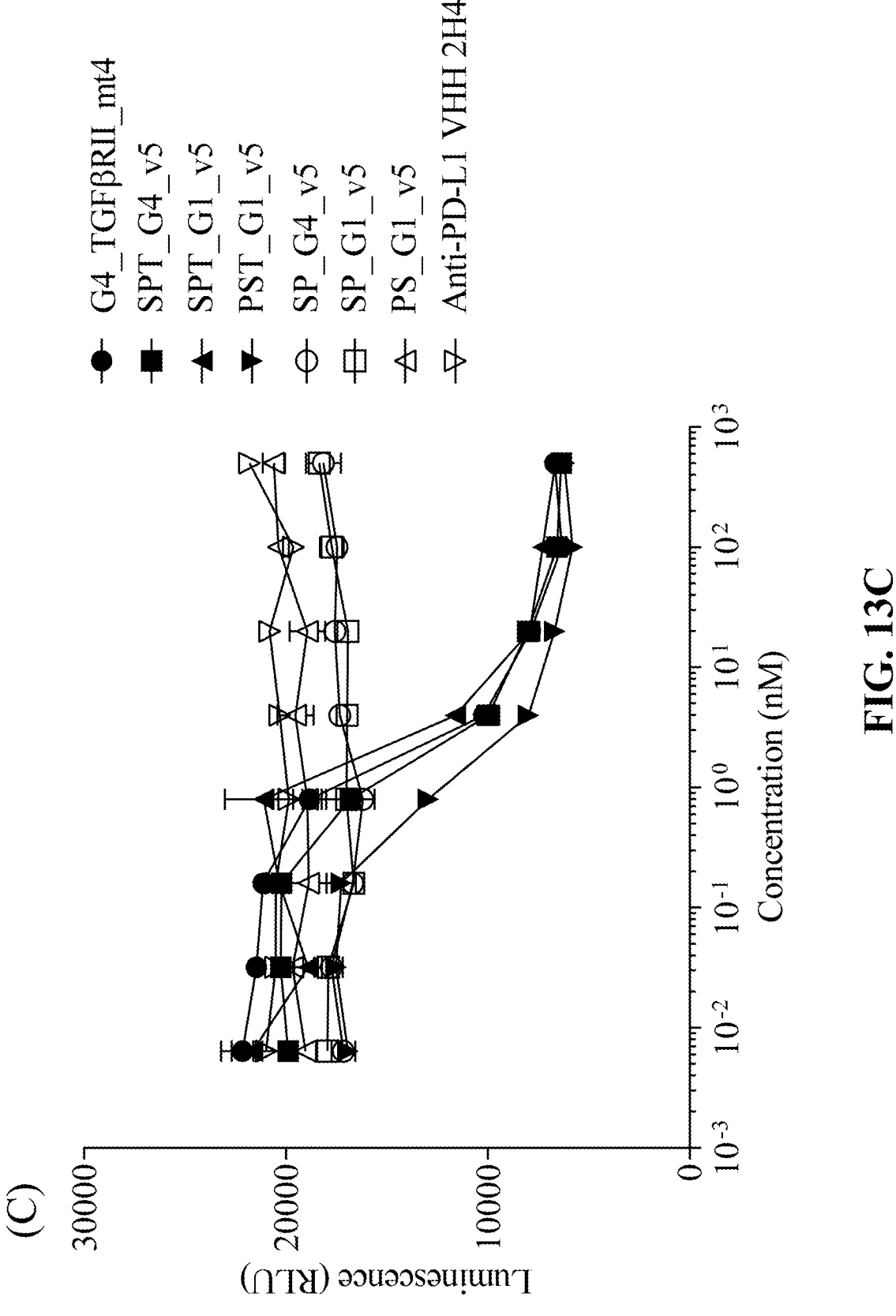
FIG. 13C shows the impact of HCB301 v5 proteins on TGFβ3-mediated smad2 reporter activity.

As shown in FIGS. 13A-13C, the three triple-targeting formats of HCB301_v5 proteins, SPT_G4_v5, SPT_G1_v5 and PST_G1_v5, as well as the positive control G4_TGFBRII_mt4, can inhibit TGFβ1-(FIG. 13A) or TGFβ3-(FIG. 13B) mediated smad2 reporter activity. By contrast, TGFβ2-(FIG. 13B) mediated smad2 reporter activities were not interfered by any of the tested proteins.

Example 14. Evaluation of the Enhancement of T Cell Activation by MLR Assay

Mixed lymphocyte reaction (MLR) assays in the presence of TGFβ1 were performed to determine the enhancement of T cell response by HCB301_v5 proteins. Specifically, $1 \times 10^5$ CD4+ T cells and $1 \times 10^4$ dendritic cells (DCs) were incubated with the HCB301_v5 proteins at 0.1 nM, 1.0 nM, 10.0 nM, or 100.0 nM. Control molecules or combinations thereof were also used for incubation, e.g., PDGFR-Fc, Atezolizumab, anti-PD-L1 VHH (2H4), HCB101, and G4_TGFBRII_mt4. PDGFR-Fc (SEQ ID NO: 35) served as a negative control. Atezolizumab was used as a positive control. TGFβ1-containing condition media from NCl-H650 cells was then added, and co-incubated for 5 days. After the co-incubation, culture supernatant was collected, and IL-2 secretion was determined using Human IL-2 ELISA MAX Deluxe kit (BioLegend, Cat #: 431805).

Figure 14:
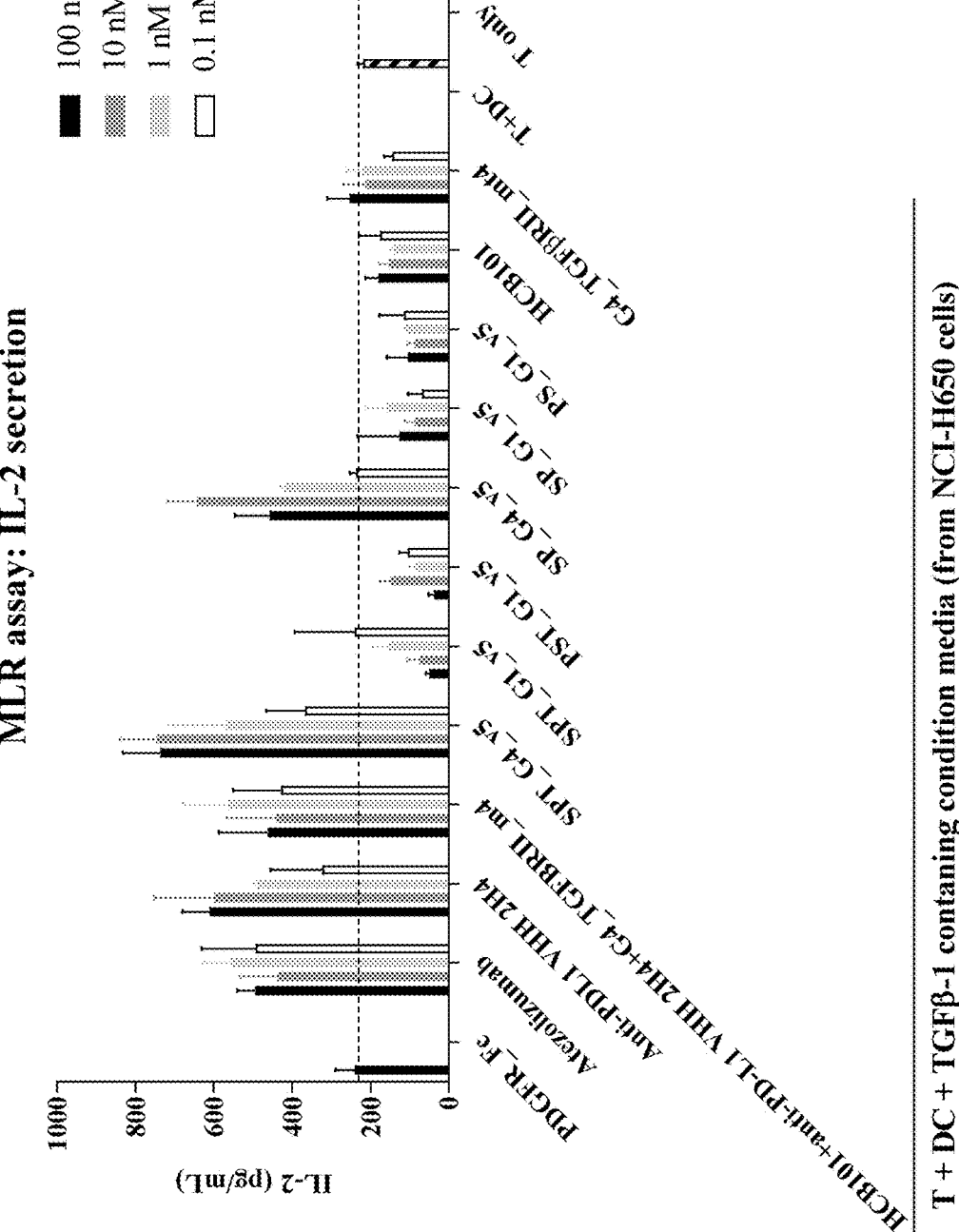
FIG. 14 shows HCB301_v5 protein-induced IL-2 secretion in MLR assays in the presence of TGFβ1 as determined by ELISA.

As shown in FIG. 14, IL-2 secretion, indicating T cell activation, was determined using Human IL-2 ELISA MAX Deluxe kit by MLR assay. The results showed that SPT_G4_v5 and SP_G4_v5, as well as positive control Atezolizumab can promote T cell activation in the presence of TGFβ1 containing condition medium. By contrast, this increased IL-2 secretion was not detected in the negative control PDGFR-Fc and the other four HCB301_v5 proteins.

Example 15. Determination of In Vivo Anti-Tumor Efficacy

The in vivo anti-tumor efficacy of the SPT_G4_v5 was determined using FaDu cells (pharynx carcinoma). Specifically, immunodeficient NPG™ mice were subcutaneously inoculated with co-mixture of $3\times10^6$ FaDu (pharynx carcinoma) and $1\times10^6$ PBMC on Day 0. The mice were then administered by intraperitoneal injection with test articles in the same molarity on Day 5, 8, 12, 15 and 19 after inoculation. The control group mice were administered with an equal volume of 0.9% Sodium Chloride Injection. The tumor volume of mice in each group was measured on Day 5, 8, 12, 15, and 19 after inoculation. The average tumor volume of mice in each group on Day 19 is shown in the table. Tumor growth inhibition (TGI) and the corresponding p value were also determined.

Figure 15A:
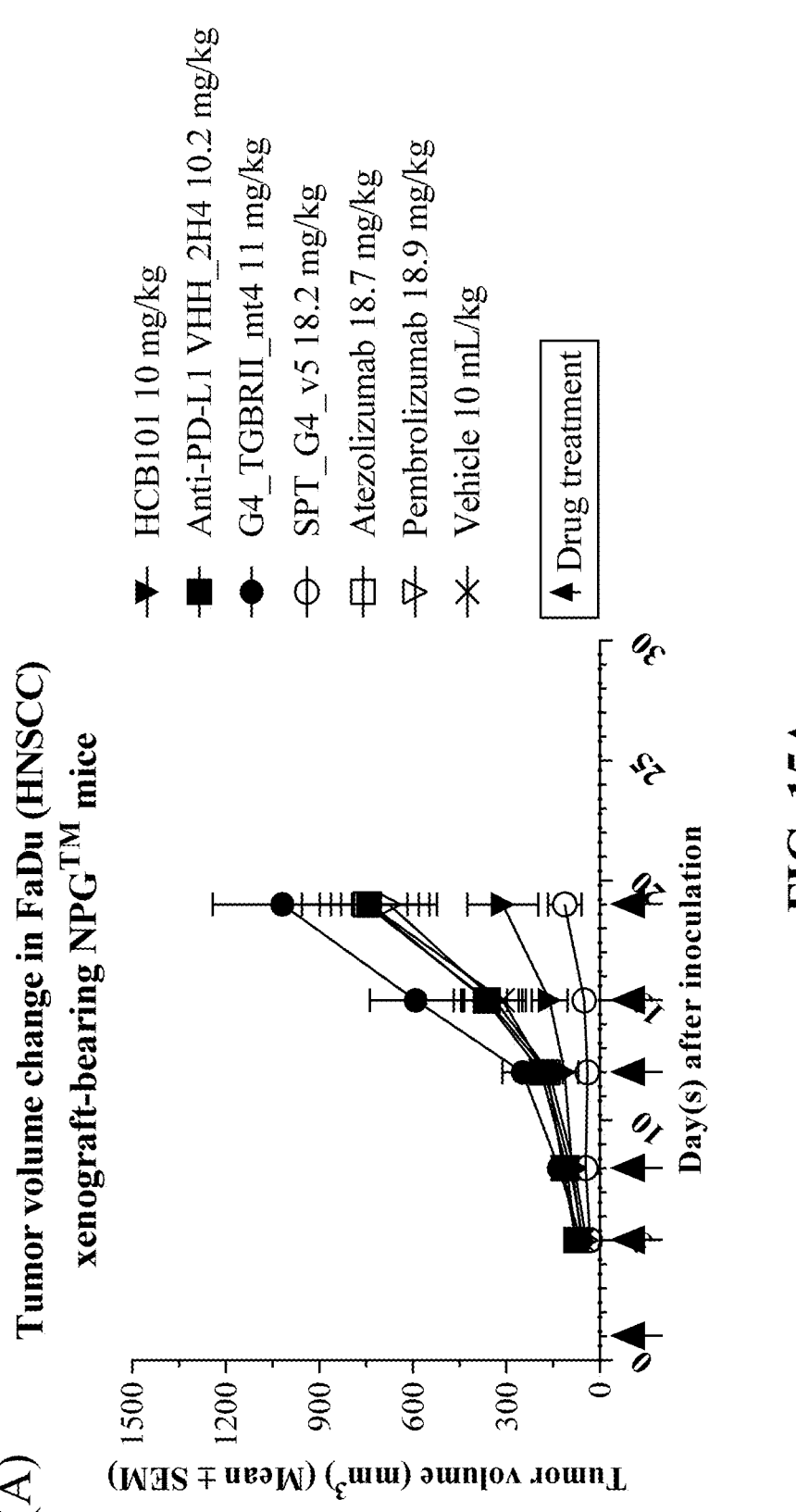
FIG. 15A shows the in vivo anti-tumor efficacy of SPT_G4_v5 by graphing the average tumor volume at multiple time point during 19 days after tumor cell inoculation.
Figure 15B:
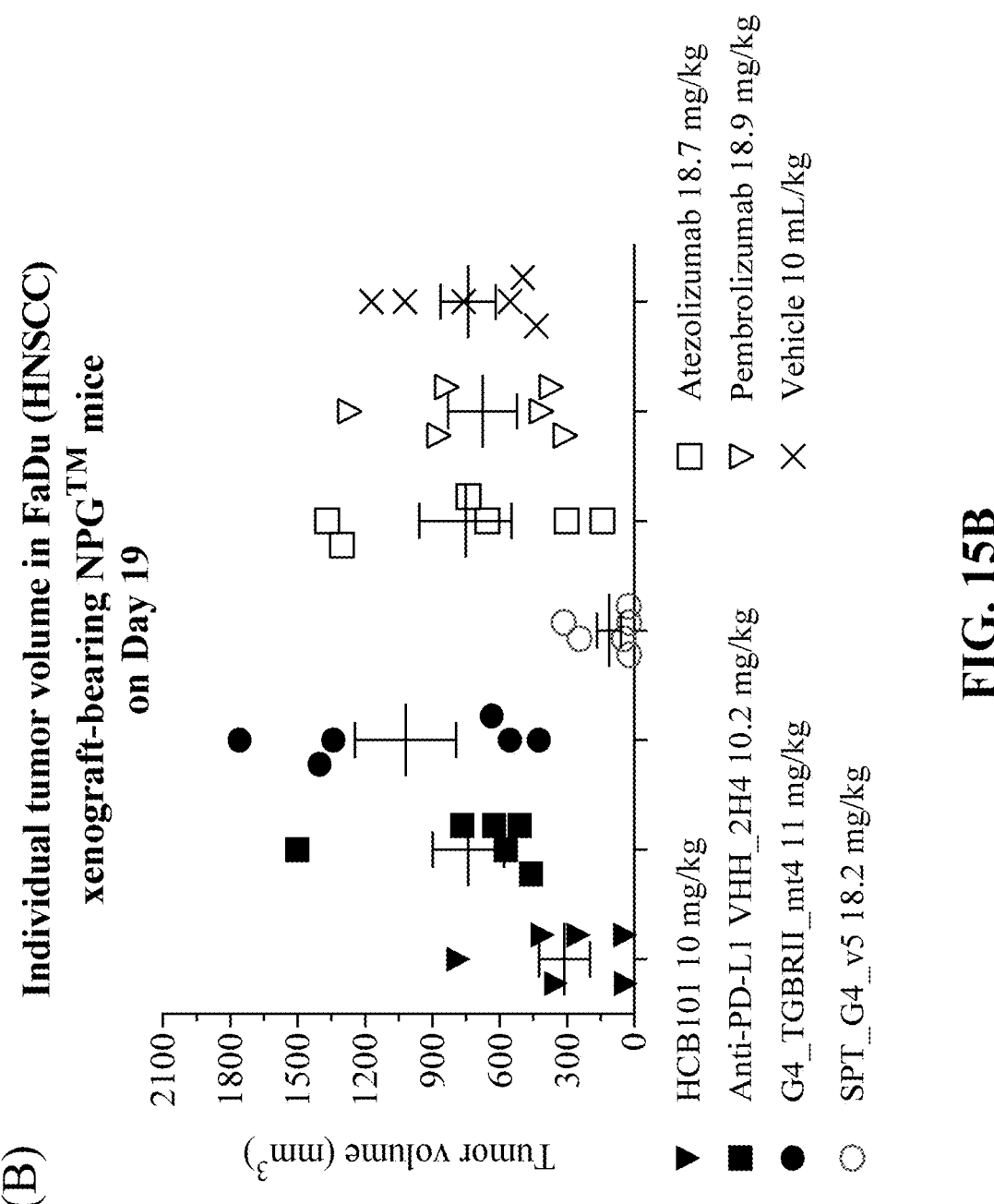
FIG. 15B shows the in vivo anti-tumor efficacy of SPT_G4_v5 by displaying individual tumor volume on Day 19 days after tumor cell inoculation.

As shown in FIGS. 15A-15B, SPT_G4_v5 treatment inhibited tumor growth as compared to HCB101, anti-PD-L1 VHH (2H4), G4_TGFβRII_mt4, Atezolizumab, and pembrolizumab in FaDu (human pharynx carcinoma)/PBMC xenograft-bearing NPG™ mice during the time course of 2.5 weeks following administration. Specifically, the mice treated with SPT_G4_v5 exhibited smaller tumors as compared to other antibody or vehicle-treated mice on Day 19 after administration. The assessment of TGI demonstrated that SPT_G4_v5 possessed a better anti-tumor activity by significantly inhibiting tumor growth by 19 days after administration as shown in the table below.

TABLE 1

| Day 19 after inoculation | Mean ± SEM (mm³) | TGI | P value |
|---|---|---|---|
| HCB101 10 mg/kg | 311.5 ± 113.5 | 58% | 0.3832 |
| Anti-PDL1 VHH_2H4 10.2 mg/kg | 740.5 ± 158.5 | 0% | >0.9999 |
| G4_TGBRII_mt4 11 mg/kg | 1020 ± 224.7 | −38% | >0.9999 |
| SPT_G4_v5 18.2 mg/kg | 113.4 ± 53.79 | 85% | 0.0336* |
| Atezolizumab 18.7 mg/kg | 752.3 ± 205.4 | −2% | >0.9999 |
| Pembrolizumab 18.9 mg/kg | 677.2 ± 153.9 | 9% | >0.9999 |
| Vehicle 10 mL/kg | 740.6 ± 122.6 | | |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A protein complex, comprising
   (a) a first polypeptide comprising from N-terminus to C-terminus: a first CD47-binding domain, a first VHH that binds to PD-L1, a first Fc region, and a first TGFβ-binding domain; and
   (b) a second polypeptide comprising from N-terminus to C-terminus: a second CD47-binding domain, a second VHH that binds to PD-L1, a second Fc region, and a second TGFβ-binding domain,
       wherein the first VHH and the second VHH comprise a sequence that is identical to SEQ ID NO: 8; wherein the first CD47-binding domain and the second CD47-binding domain comprise a sequence that is identical to SEQ ID NO: 7; wherein the first TGFβ-binding domain and the second TGFβ-binding domain comprise a sequence that is identical to SEQ ID NO: 9.

2. The protein complex of claim 1, wherein the first polypeptide and the second polypeptide comprise a sequence that is identical to SEQ ID NO: 1 or 2.

3. A protein conjugate comprising the protein complex of claim 1, covalently bound to a therapeutic agent.

4. A pharmaceutical composition comprising the protein complex of claim 1, and a pharmaceutically acceptable carrier.

5. A nucleic acid comprising a polynucleotide encoding the protein complex of claim 1.

6. A vector comprising the nucleic acid of claim 5.

7. A cell comprising the nucleic acid of claim 5.

8. A method of producing a protein complex, the method comprising
   (a) culturing the cell of claim 7 under conditions sufficient for the cell to produce the protein complex; and
   (b) collecting the protein complex produced by the cell.

9. A method of treating a subject having cancer, the method comprising administering a therapeutically effective amount of a composition comprising the protein complex of claim 1, to the subject.

10. The method of claim 9, wherein the subject has a cancer cell expressing CD47 or PD-L1.

11. The method of claim 9, wherein the cancer is breast cancer, prostate cancer, non-small cell lung cancer, pancreatic cancer, diffuse large B-cell lymphoma, mesothelioma, lung cancer, ovarian cancer, colon cancer, pleural tumor, glioblastoma, esophageal cancer, gastric cancer, synovial sarcoma, thymic carcinoma, endometrial carcinoma, stomach cancer, cholangiocarcinoma, head and neck cancer, blood cancer, or a combination thereof.

12. The method of claim 9, wherein the cancer is a solid tumor.

13. A method of decreasing the rate of tumor growth or killing a tumor cell, the method comprising
   contacting a tumor cell with an effective amount of a composition comprising the protein complex of claim 1.

* * * * *